(12) United States Patent
Kheir et al.

(10) Patent No.: US 11,918,773 B2
(45) Date of Patent: Mar. 5, 2024

(54) APPARATUSES FOR CLEANING CATHETER PORTS

(71) Applicant: Children's Medical Center Corporation, Boston, MA (US)

(72) Inventors: John Kheir, Charlestown, MA (US); Pierre DuPont, Wellesley, MA (US); Asghar Ataollahi, Brookline, MA (US); Sarah Ward Goldberg, Brookline, MA (US); Brian D. Polizzotti, Swampscott, MA (US)

(73) Assignee: Children's Medical Center Corporation, Boston, MA (US)

( * ) Notice: Subject to any disclaimer, the term of this patent is extended or adjusted under 35 U.S.C. 154(b) by 101 days.

(21) Appl. No.: 17/340,516

(22) Filed: Jun. 7, 2021

(65) Prior Publication Data

US 2022/0008710 A1 Jan. 13, 2022

Related U.S. Application Data

(63) Continuation of application No. 16/745,150, filed on Jan. 16, 2020, now Pat. No. 11,027,112, which is a
(Continued)

(51) Int. Cl.
*A61M 39/16* (2006.01)
*A61M 25/00* (2006.01)
(Continued)

(52) U.S. Cl.
CPC ........ *A61M 39/162* (2013.01); *A61M 25/002* (2013.01); *A61M 25/0097* (2013.01);
(Continued)

(58) Field of Classification Search
CPC ............ A61M 25/002; A61M 25/0097; A61M 39/162; A61M 39/1011; A61M 39/20;
(Continued)

(56) References Cited

U.S. PATENT DOCUMENTS 3,446,596 A 5/1969 Salivar et al.
3,860,348 A 1/1975 Doyle
(Continued)

FOREIGN PATENT DOCUMENTS

CN 203989119 U 12/2014
WO WO 2006/099306 A2 9/2006
(Continued)

OTHER PUBLICATIONS

International Search Report and Written Opinion for International Application No. PCT/US2015/051112 dated Jan. 22, 2016.
(Continued)

*Primary Examiner* — Timothy C Cleveland
(74) *Attorney, Agent, or Firm* — Wolf, Greenfield & Sacks, P.C.

(57) ABSTRACT

Methods and apparatus for cleaning a central venous catheter port are disclosed. An apparatus includes a body, a coupling configured to connect the body to the hub, a cleaning cap coupled to the body, and an actuator disposed within the body for rotating and translating the cap relative to the hub. The cleaning cap includes a cap body defining a cavity and a cleaning member disposed within the cavity, the cleaning member having threads that engage with the threads on the hub.

27 Claims, 62 Drawing Sheets

Related U.S. Application Data continuation of application No. 15/512,399, filed as application No. PCT/US2015/051112 on Sep. 19, 2015, now Pat. No. 10,569,075.

(60) Provisional application No. 62/073,154, filed on Oct. 31, 2014, provisional application No. 62/053,049, filed on Sep. 19, 2014.

(51) Int. Cl.
*A61M 39/10* (2006.01)
*A61M 39/20* (2006.01)
*B08B 1/00* (2006.01)
*B08B 1/04* (2006.01)
*B08B 17/06* (2006.01)

(52) U.S. Cl.
CPC ........ *A61M 39/1011* (2013.01); *A61M 39/20* (2013.01); *B08B 1/001* (2013.01); *B08B 1/008* (2013.01); *B08B 1/04* (2013.01); *B08B 17/065* (2013.01); *A61M 2025/0019* (2013.01); *A61M 2039/167* (2013.01); *A61M 2205/0205* (2013.01); *A61M 2205/0238* (2013.01); *A61M 2205/52* (2013.01); *A61M 2205/581* (2013.01); *A61M 2205/582* (2013.01); *A61M 2205/583* (2013.01); *A61M 2205/584* (2013.01); *A61M 2207/00* (2013.01); *A61M 2209/10* (2013.01)

(58) Field of Classification Search
CPC ......... A61M 2205/0205; A61M 2205/023852; A61M 2205/581; A61M 2205/582; A61M 2205/583; A61M 2205/584; A61M 2207/00; A61M 2025/0019; A61M 2039/167; A61M 2209/10; B08B 1/001; B08B 1/008; B08B 1/04; B08B 17/065
See application file for complete search history.

(56) References Cited

U.S. PATENT DOCUMENTS

| | | |
|---|---|---|
| 3,987,930 A | 10/1976 | Fuson |
| 4,232,677 A | 11/1980 | Leibinsohn |
| 4,340,052 A | 7/1982 | Dennehey et al. |
| 4,432,764 A | 2/1984 | Lopez |
| 4,432,766 A | 2/1984 | Bellotti et al. |
| 4,440,207 A | 4/1984 | Genatempo et al. |
| 4,778,447 A | 10/1988 | Velde et al. |
| 5,205,821 A | 4/1993 | Kruger et al. |
| 5,242,425 A | 9/1993 | White et al. |
| 5,471,706 A | 12/1995 | Wallock et al. |
| 5,554,135 A | 9/1996 | Menyhay |
| 5,694,978 A | 12/1997 | Heilmann et al. |
| 5,702,017 A | 12/1997 | Goncalves |
| 5,743,892 A | 4/1998 | Loh et al. |
| 5,792,120 A | 8/1998 | Menyhay |
| 5,894,015 A | 4/1999 | Rechtin |
| 5,951,519 A | 9/1999 | Utterberg |
| 5,954,957 A | 9/1999 | Chin-Loy et al. |
| 6,045,539 A | 4/2000 | Menyhay |
| 6,171,287 B1 | 1/2001 | Lynn et al. |
| 6,523,686 B1 | 2/2003 | Bae |
| 6,932,795 B2 | 8/2005 | Lopez et al. |
| 6,960,191 B2 | 11/2005 | Howlett et al. |
| 7,040,598 B2 | 5/2006 | Raybuck |
| 7,198,611 B2 | 4/2007 | Connell et al. |
| 7,282,186 B2 | 10/2007 | Lake, Jr. et al. |
| 7,316,669 B2 | 1/2008 | Ranalletta |
| D607,325 S | 1/2010 | Rogers et al. |
| 7,682,561 B2 | 3/2010 | Davis et al. |
| 7,762,524 B2 | 7/2010 | Cawthon et al. |
| 7,780,794 B2 | 8/2010 | Rogers et al. |
| 7,834,328 B2 | 11/2010 | Redmond et al. |
| 7,922,701 B2 | 4/2011 | Buchman |
| 7,985,302 B2 | 7/2011 | Rogers et al. |
| 9,963,597 B2 | 5/2018 | Aizenberg et al. |
| 10,569,075 B2 | 2/2020 | DuPont et al. |
| 11,027,112 B2 | 6/2021 | Kheir et al. |
| 2002/0093192 A1 | 7/2002 | Matkovich |
| 2003/0140441 A1 | 7/2003 | Stafford |
| 2003/0153865 A1 | 8/2003 | Connell et al. |
| 2003/0198502 A1 | 10/2003 | Maloney et al. |
| 2004/0039341 A1 | 2/2004 | Ranalletta |
| 2004/0195136 A1 | 10/2004 | Young et al. |
| 2004/0201216 A1 | 10/2004 | Segal et al. |
| 2004/0258560 A1 | 12/2004 | Lake, Jr. et al. |
| 2005/0124970 A1 | 6/2005 | Kunin et al. |
| 2005/0147524 A1 | 7/2005 | Bousquet |
| 2005/0203460 A1 | 9/2005 | Kim |
| 2005/0245883 A1 | 11/2005 | Baldwin |
| 2005/0266714 A1 | 12/2005 | Higgins et al. |
| 2006/0030827 A1 | 2/2006 | Raulerson et al. |
| 2007/0112333 A1 | 5/2007 | Hoang et al. |
| 2007/0202177 A1 | 8/2007 | Hoang |
| 2007/0282280 A1 | 12/2007 | Tennican |
| 2008/0019889 A1 | 1/2008 | Rogers et al. |
| 2008/0021381 A1 | 1/2008 | Lurvey et al. |
| 2008/0038167 A1 | 2/2008 | Lynn |
| 2008/0039803 A1 | 2/2008 | Lynn |
| 2008/0086091 A1 | 4/2008 | Anderson et al. |
| 2008/0107564 A1 | 5/2008 | Sternberg et al. |
| 2008/0132880 A1 | 6/2008 | Buchman |
| 2008/0147047 A1 | 6/2008 | Davis et al. |
| 2008/0177250 A1 | 7/2008 | Howlett et al. |
| 2008/0235888 A1 | 10/2008 | Vaillancourt et al. |
| 2009/0008393 A1 | 1/2009 | Howlett et al. |
| 2009/0028750 A1 | 1/2009 | Ryan |
| 2009/0041619 A1 | 2/2009 | Cady et al. |
| 2009/0062766 A1 | 3/2009 | Howlett et al. |
| 2009/0137969 A1 | 5/2009 | Colantonio et al. |
| 2009/0175759 A1 | 7/2009 | Davis et al. |
| 2009/0205151 A1 | 8/2009 | Fisher et al. |
| 2009/0257910 A1 | 10/2009 | Segal |
| 2009/0297400 A1 | 12/2009 | Cady et al. |
| 2010/0049170 A1 | 2/2010 | Solomon et al. |
| 2010/0064456 A1 | 3/2010 | Ferlic |
| 2010/0200017 A1 | 8/2010 | Kerr et al. |
| 2010/0242993 A1 | 9/2010 | Hoang et al. |
| 2010/0292673 A1 | 11/2010 | Korogi |
| 2010/0306938 A1 | 12/2010 | Rogers et al. |
| 2010/0313366 A1 | 12/2010 | Rogers et al. |
| 2011/0044850 A1 | 2/2011 | Solomon et al. |
| 2011/0085936 A1 | 4/2011 | Haytman et al. |
| 2011/0106019 A1 | 5/2011 | Bagwell et al. |
| 2011/0154591 A1 | 6/2011 | Ernster |
| 2011/0213341 A1 | 9/2011 | Solomon et al. |
| 2011/0217212 A1 | 9/2011 | Solomon et al. |
| 2011/0232020 A1 | 9/2011 | Rogers et al. |
| 2011/0265834 A1 | 11/2011 | Tennican |
| 2011/0284024 A1 | 11/2011 | Trebella et al. |
| 2011/0314619 A1 | 12/2011 | Schweikert |
| 2012/0016318 A1 | 1/2012 | Hoang et al. |
| 2012/0042466 A1 | 2/2012 | Colantonio et al. |
| 2012/0296284 A1 | 11/2012 | Anderson et al. |
| 2013/0023828 A1 | 1/2013 | Anderson et al. |
| 2013/0197485 A1 | 8/2013 | Gardner et al. |
| 2013/0323120 A1 | 12/2013 | Ma |
| 2014/0053871 A1 | 2/2014 | Ma et al. |
| 2014/0264074 A1 | 9/2014 | Victor et al. |
| 2014/0334974 A1 | 11/2014 | Rasooly et al. |
| 2017/0043126 A1 | 2/2017 | Jones et al. |
| 2017/0050012 A1 | 2/2017 | Alpert |
| 2017/0274198 A1 | 9/2017 | DuPont et al. |
| 2020/0289811 A1 | 9/2020 | Kheir et al. |

FOREIGN PATENT DOCUMENTS

| | | |
|---|---|---|
| WO | WO 2008/089196 A2 | 7/2008 |
| WO | WO 2008/100950 A2 | 8/2008 |
| WO | WO 2010/002808 A1 | 1/2010 |
| WO | WO 2010/141508 A1 | 12/2010 |
| WO | WO 2011/053924 A1 | 5/2011 |

(56) References Cited

FOREIGN PATENT DOCUMENTS

| WO | WO 2011/066565 A1 | 6/2011 |
|---|---|---|
| WO | WO 2011/066586 A1 | 6/2011 |
| WO | WO 2011/120017 A1 | 9/2011 |
| WO | WO 2013/066285 A1 | 5/2013 |

OTHER PUBLICATIONS

International Preliminary Report on Patentability for International Application No. PCT/US2015/051112 dated Mar. 30, 2017.
Partial Supplementary European Search Report for European Application No. 15842984.5, dated May 4, 2018.
Extended European Search Report for European Application No. 15842984.5, dated Aug. 10, 2018.
[No Author Listed] 3M.TM. Curos.TM. Disinfecting Cap for Needleless Connectors. Last Accessed on Jun. 19, 2017 from http://www.3m.com/3M/en_US/company-us5b4/all-3m-products/.about./3M-Curos-Di-sinfecting-Cap-for-Needleless-Connectors?N=5002385+3292659417&rt=rud. 2pages.
[No Author Listed] Guide to the Elimination of Catheter-Related Bloodstream Infections. An APIC Guide. 2009;1-58.
[No Author Listed] ICU Medical. Swap Cap: Disinfecting Cap for Needlefree Connectors. Last Accessed on Jun. 19, 2017 from http://www.icumed.com/products/infusion-therapy/disinfecting-caps/swabcap- .aspx. 1 page.
[No Author Listed] National Nosocomial Infections Surveillance System. National Nosocomial Infections Surveillance (NNIS) System Report, data summary from Jan. 1992 through Jun. 2004, issued Oct. 2004. Am J Infect Control. Dec. 2004;32(8):470-85.
Casey et al., A prospective clinical trial to evaluate the microbial barrier of a needleless connector. Journal of Hospital Infection. 2007;(65):212-8.
Halton et al., Economic evaluation and catheter-related bloodstream infections. Emerging Infectious Diseases. Jun. 2007;13(6):815-23.
Harbarth et al., The preventable proportion of nosocomial infections: an overview of published reports. Journal of Hospital Infection. 2003;(54):258-66.
Menyhay et al., Preventing central venous catheter-associated bloodstream infections: development of an antiseptic barrier cap for needleless connectors. Am J Infec5b4t Control. 2008;36(10):1-5.
Mermel, Prevention of intravascular catheter-related infections. Ann Intern Med. Mar. 7, 2000;132(5):391-402.
O'Grady et al., Guidelines for the Prevention of Intravascular Catheter-related Infections. Clinical Infectious Diseases: An Official Publication of the Infectious Diseases Society of America. 2011;52(9):e162-e193.
Soothill et al., A fall in bloodstream infections followed a change to 2% chlorhexidine in 70% isopropanol for catheter connection antisepsis: a pediatric single center before/after study on a hemopoietic stem cell transplant ward. American Journalof Infection Control. 2009;(37):626-30.
PCT/US2015/051112, Jan. 22, 2016, International Search Report and Written Opinion.
PCT/US2015/051112, Mar. 30, 2017, International Preliminary Report on Patentability.
EP15842984.5, May 4, 2018, Partial Supplementary European Search Report.
EP15842984.5, Aug. 10, 2018, Extended European Search Report.

|  | POLYMER | FOAM TYPE | Q VALUE |
|---|---|---|---|
| 7B | MEMORY FOAM | OPEN CELL | 660 |
| 9 | MELAMINE | OPEN CELL (145μm) | 724 |
| 2A | POLYETHER | OPEN CELL | 2885 |
| 10B | LINEAR POLYETHYLENE | CLOSED CELL | 154 |
| 1A | POLYESTER | OPEN CELL | 2002 |
| 3 | POLYETHER/POLYESTER | OPEN CELL | 1308 |
| 4 | POLYETHER | OPEN CELL | 2540 |
| 7A | MEMORY FOAM | OPEN CELL | 791 |
| 10A | LINEAR POLYETHYLENE | CLOSED CELL | 549 |
| 12D | CROSSLINKED POLYETHYLENE | CLOSED CELL | 120 |
| 12C | CROSSLINKED POLYETHYLENE | CLOSED CELL | 262 |
| 12B | CROSSLINKED POLYETHYLENE | CLOSED CELL | 64 |
| 12A | CROSSLINKED POLYETHYLENE | CLOSED CELL | 188 |
| 6 | POLYURETHANE | OPEN CELL | 1870 |
| 2B | POLYETHER | OPEN CELL | 1777 |
| 1B | POLYESTER | OPEN CELL | 562 |
| 5 | POLYETHER | OPEN CELL | 2106 |
| 8 | CAST URETHANE | MICRO CELL | 376 |
| 11A | CROSSLINKED POLYETHYLENE | CLOSED CELL | 229 |
| 16 | POLYVINYL CHLORIDE | CLOSED CELL | 84 |
| 17A | VINYL NITRIDE | CLOSED CELL | 150 |
| 17B | EPDM | CLOSED CELL | 59 |

FIG. 56

APPARATUSES FOR CLEANING CATHETER PORTS

CROSS-REFERENCE TO RELATED APPLICATIONS

This application claims the benefit under 35 U.S.C. § 120 and is a continuation of U.S. application Ser. No. 16/745,150, entitled "APPARATUSES FOR CLEANING CATHETER PORTS" and filed Jan. 16, 2020, which claims the benefit under 35 U.S.C. § 120 and is a continuation of U.S. application Ser. No. 15/512,399, entitled "APPARATUSES FOR CLEANING CATHETER PORTS" and filed Mar. 17, 2017, which is a national stage filing under 35 U.S.C. § 371 of International Application No. PCT/US2015/051112, entitled APPARATUSES FOR CLEANING CATHETER PORTS and filed Sep. 19, 2015. International Application No. PCT/US2015/051112 claims the benefit under 35 U.S.C. § 119(e) to U.S. provisional application Ser. No. 62/053,049, entitled APPARATUSES FOR CLEANING CATHETER PORTS and filed Sep. 19, 2014, and to U.S. provisional application Ser. No. 62/073,154, entitled APPARATUSES FOR CLEANING CATHETER PORTS and filed Oct. 31, 2014. The disclosures of each of the applications listed above are incorporated by reference herein in their entireties.

FIELD

The disclosed embodiments are generally directed to apparatuses for cleaning a catheter port.

BACKGROUND

Catheters such as central venous catheters ("CVCs") are placed into large veins of the human body (e.g., the jugular vein, the axillary vein, or the femoral vein). Needleless CVC connectors are used for injecting medications, administering an intravenous ("IV") infusion, and collecting blood samples, as they eliminate the potential for a bedside providers to prick themselves with a needle. Catheter-related bloodstream infections ("CLABSIs") are a serious healthcare problem, and needleless catheter ("NC") hubs are thought to be a primary mechanism of infection transmission. Cleaning the NC has been shown to be an important step in the reduction in CLABSI incidence.

SUMMARY OF INVENTION

According to one embodiment, an apparatus for cleaning a hub of a catheter is disclosed. The apparatus includes a body, a coupling configured to connect the body to the hub, a cleaning cap coupled to the body, and an actuator disposed within the body for rotating and translating the cap relative to the hub.

According to another embodiment, a cleaning cap for cleaning a needleless hub of a catheter is disclosed. The cap includes a cap body defining a cavity, and a cleaning member disposed within the cavity, the cleaning member having cleaning threads that engage with external threads of the hub.

According to another embodiment, an apparatus for cleaning a hub of a catheter is disposed. The apparatus includes a body, a coupling arranged to connect the body to the hub, the coupling having an opening for receiving the hub, a cleaning cap coupled to the body, and an actuator disposed within the body for rotating and translating the cap relative to the hub. The hub is snapped into the opening. When the hub is snapped into the opening, the hub does not rotate or translate relative to the coupling.

According to yet another embodiment, a cleaning solution for disinfecting surfaces contaminated with biological material is disposed. The solution includes a mixture of isopropyl alcohol, chlorhexidine gluconate and hydrogen peroxide.

According to still another embodiment, a cleaning cap constructed and arranged for use with cleaning a hub of a catheter is disclosed. The cleaning cap contains at least one of a disinfecting substance and an antiseptic fluid.

According to another embodiment, charging station for use with a device for cleaning a catheter hub is disclosed. The charging station includes a housing and a port disposed in the housing for receiving the device. The charging station is arranged to load an unused cap into a cap holder of the device.

According to another embodiment, a method of cleaning a hub of a catheter with an automated hub cleaning device is disclosed. The automated hub cleaning device includes a holder to engage the hub, a cleaning cap to clean the hub and a motor to move the cap and the holder. The method includes engaging the automated hub cleaning device with the hub, entering a hub cleaning mode whereby the automated hub cleaning device automatically moves the holder with an engaged hub relative to the cleaning cap to engage the hub with the cleaning cap and thereafter moving the cleaning cap relative to the hub to clean the hub, entering a hub drying mode whereby the automated hub cleaning device automatically disengages the cleaning cap from the hub and the hub remains engaged with the holder for a predetermined drying time, and entering a hub presentation mode whereby the automated hub cleaning device automatically moves the hub to a position whereby the hub can be removed from the holder.

According to still another embodiment, a method of modifying a standard catheter hub is disclosed. The method includes at least one of chemically changing a surface of the hub, chemically coating the surface of the hub with a super slippery thin films and physically changing the morphology of the surface of the hub.

It should be appreciated that the foregoing concepts, and additional concepts discussed below, may be arranged in any suitable combination, as the present disclosure is not limited in this respect.

The foregoing and other aspects, embodiments, and features of the present teachings can be more fully understood from the following description in conjunction with the accompanying drawings.

BRIEF DESCRIPTION OF DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings:

FIG. 56 is a chart showing various foam types according to various embodiments;

DETAILED DESCRIPTION OF INVENTION

Figure 1A:
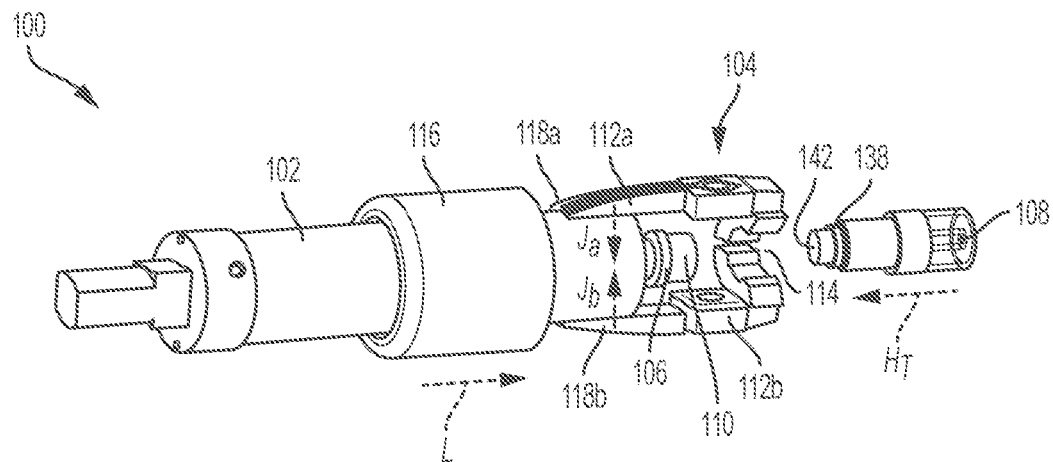
FIG. 1A is a perspective view of a cleaning device disengaged from a catheter hub according to one embodiment.

Central line associated bloodstream infections ("CLABSIs") are a serious healthcare problem in the United States, having a major clinical and economic effect on critically ill patients. Needleless central venous catheter ("CVC") connectors (also known as "NCs") are the interface by which equipment containing fluid to be injected into the bloodstream (e.g. syringes for bolusing medications or flushes, or tubing connecting such a syringe or bag using a pump) is connected to CVC ports. Alternatively, blood can be withdrawn from a patient through a CVC utilizing a NC—this process includes three (3) syringe changes (one to remove a waste amount of blood, a second to collect the sample, and a final one to flush fluid back into the CVC), and presents a significant risk for catheter contamination. Although these steps are commonplace in the use of CVCs, they are a primary mechanism by which microorganisms contaminate CVCs and cause CLABSIs.

Traditionally, CVC hubs are sterilized according to specific guidelines published by the Centers for Disease Control and Prevention ("CDC"). Such guidelines require that the visible areas of the cap and hub be swabbed with an antiseptic wipe, that the hub be disinfected by rubbing and scrubbing with a second antiseptic wipe (e.g., by generating friction by scrubbing the antiseptic wipe in a twisting motion over the threads and tip of the hub), and that the hub be allowed to dry. As will be appreciated, CVC hubs may not have threads in some types, and, thus, scrubbing of the side surface and tip surface may be necessary. Although this approach may reduce the number of catheter-related bloodstream infections, there may be discrepancies between the CDC guidelines and actual practice due to inconsistent forces and duration used in manual swabbing, process fatigue (e.g., non-compliance with recommended practice due to competing factors, such as workload and emergent patient conditions), and frank human error (e.g., contamination after sterilization). Various devices have been developed to improve manual cleansing of NCs. One example is a scrubbing cap with a rigid plastic body and a filler having antiseptic-impregnated foam fingers. This cap is manually twisted while maintaining a contact pressure with the hub. Another example is a cap which allows for passive disinfecting while the hub is capped. Motorized devices also have been developed, which allow for powered rotation of a cleaning head or scrub brush with respect to the hub. Ultraviolet light has been described as a bactericidal mechanism, but in isolation, such a technique does not allow for the mechanical removal of debris and blood from the NC, an important benefit of mechanical decontamination of NCs.

According to one aspect, an apparatus for cleaning a CVC port such as a needleless catheter hub is disclosed. For purposes herein, cleaning may include scrubbing, disinfecting, decontaminating, cleansing, swabbing, and/or sterilizing. The device also may be used on any 'female' luer connector, including the hub of the CVC itself, for instances in which the NC is being replaced (e.g., for routine tubing and NC changes or for inability to withdraw blood through an in situ NC). In some embodiments, the apparatus is a hand-held device that has a body, an attachment mechanism for connecting the body to the hub, a cleaning cap, and an assembly within the body for rotating and translating the cap relative to the hub. In some embodiments, the assembly is configured to move the cap linearly back and forth and also to rotate the cap clockwise and/or counterclockwise to clean the sides and tip of the hub. In these embodiments, the apparatus standardizes the cleaning of the device (e.g., swabbing and scrubbing) by consistently and efficiently performing a cleaning protocol. For example, in some embodiments, the device may be locked onto the hub until the cleaning protocol is complete, standardizing the force and duration of cleaning, as well as the volume of chlorhexidine and alcohol used to clean; this ensures perfect compliance with recommended practice and removes variability in practice. As will be appreciated, in some embodiments, this may allow a clinician to attach the device to the hub, activate the device for cleaning, and walk away and tend to another patient while the hub is being cleaned. It should be appreciated that a clinician may be a doctor, a nurse, a technician, a medical assistant or other medical professional responsible for administering and cleaning NC hubs. In some embodiments, the device may have a visual or audible indication to alert the clinician that the cleaning protocol has been completed, thus allowing the apparatus to be unlocked and removed from the hub. The apparatus also may include a fan or compressed, sterile gas to dry the hub after being cleaned. In some embodiments, fans, compressed air, filtered air or heat (e.g., light) may be used to dry a cleaning solution (e.g., chlorhexidine) from the NC following scrubbing. In other embodiments, a vacuum may be applied to the sealed cleaning compartment to allow for an accelerated evaporation without exposure to the surrounding air. Light also may be used to slightly heat the cap and cause evaporation. As will be appreciated, expediting the drying process may shorten the overall time for cleaning and may improve the usability of the device (total cleansing time, at times up to 60 seconds using manual cleansing, is a major barrier to compliance with this practice). In some embodiments, the device includes a charging station. In these embodiments, the apparatus may minimize or even eliminate potential re-contamination of the hub.

According to another aspect, a cleaning cap for cleaning a NC is disclosed. In some embodiments, the cap includes a body and an internal cleaning member having a shape that is configured to complement the shape of the hub. For example, the cleaning member may have cleaning threads that correspond to the threads on the hub. In such embodiments, the cap may be rotated so that the cleaning threads engage with the hub threads. In some embodiments, the cleaning member is also configured to flex outwardly and away from the hub so that the cleaning member with its cleaning threads can slide over and around the hub threads. In some embodiments, the cleaning member may be compressed axially and radially, which may facilitate cleaning of the hub tip and hub threads. For example, in some embodiments, during the cleaning procedure, sufficient friction between the hub surface and the cleaning member is maintained by both lateral compliance of the cap and axial actuation force. Such compliance between the cap and the hub may allow for thorough cleaning of both sides of the hub threads and of the hub tip. NCs contain a compressible plunger. The space between the plunger and the remaining head of the NC (a distance of about 100 microns) makes it difficult to reach using manual cleansing or currently available devices. The specific design of the cleaning cap may contain a small extrusion (see, e.g., the cleaning pin 350 of FIG. 7A) which slightly depresses the plunger and cleans the aforementioned space.

In another embodiment, the handheld device may be placed partially or completely into a charging station. In some embodiments, this charging station may sterilize the device using continuous exposure to ultraviolet light, exposure to heat or sonication, or by immersing it within a sterilizing fluid.

As shown in FIG. 1A, in one embodiment, a cleaning device 100 includes a body 102, an attachment mechanism 104, and a cap holder 106. As previously described, the attachment mechanism 104 may be used to attach a CVC port such as a needleless hub 108 to the body 102 of the device 100. The cap holder 106 may be configured to hold a cleaning cap 110, which, as will be described, may be translated and rotated to clean the hub 108.

Figure 5A:
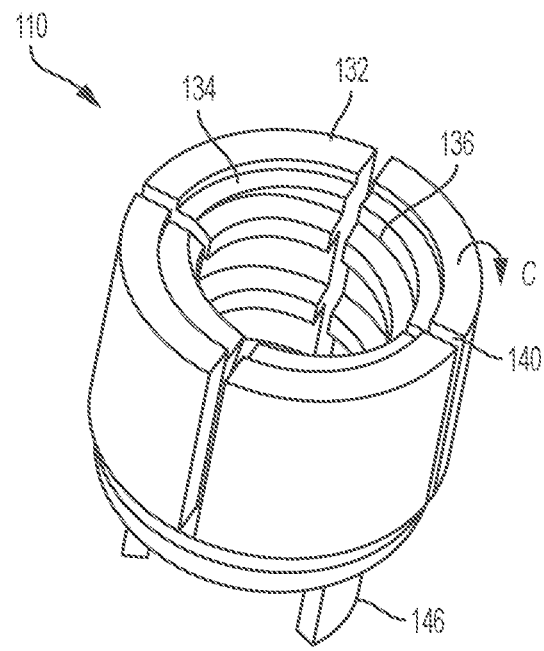
FIG. 5A is a perspective view of a cleaning cap for use with a cleaning device according to one embodiment.
Figure 5B:
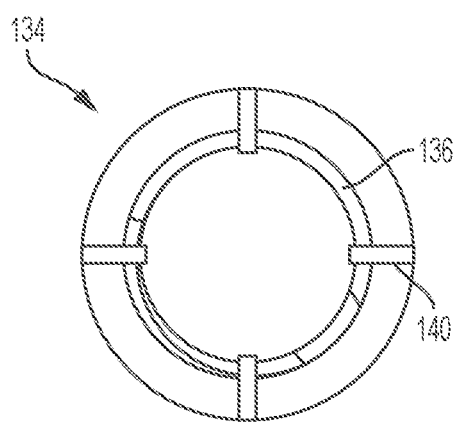
FIG. 5B is a top view of the cleaning cap of FIG. 5A.

As illustrated in FIG. 1A, the cap holder 106 is configured to hold the cap 110 during the cleaning protocol. In such an embodiment, a shape of the bottom of the cap 110 corresponds to the shape of an opening defined by the cap holder 106 such that the cap 110 may be held by or otherwise engage with the cap holder 106. In some embodiments, the cap 110 and the cap holder 106 have a snap fit engagement. As shown in FIG. 5A, in one embodiment, the cap 110 may have actuation pins 146 that are received by the cap holder 106. As will be appreciated, the cap 110 may be removably attachable to the cap holder 106, such that a new cap 110 may be inserted into the cap holder 106 prior to each cleaning.

In some embodiments, the cap 110 is manually loaded into the cap holder 106 by the clinician. In other embodiments, the cap may be a part of a multi-pack cartridge 500 (see FIG. 10) and may be automatically loaded into the cap holder 106 upon engagement between the device 100 and the cartridge (e.g., by inserting the device 100 into or against the cartridge). As will be appreciated, the multi-pack cartridge 500 may be sterile and may load the cap 110 into the cap holder 106 while maintaining sterility. The cartridge 500 may be configured as a stand-alone unit or also may be integrated into another portion of the device 100 (e.g., into a charging station). The device 100 also may be configured to install a new cleaning cap before the cleaning protocol (e.g., before an injection). As will be appreciated, the cap 110 may be disposable.

In some embodiments, the cap 110 is manually removed from the cap holder 106 after the cleaning protocol is complete and after the hub 108 has been removed from the device 100. In other embodiments, the device 100 may include an ejector (not shown), which is configured to eject the cap 110 from the cap holder 106. In some embodiments, a clinician pushes an ejection button (not shown) on the device to activate the ejector and eject the cap 110 from the cap holder 106. In other embodiments, the ejector is configured to be activated automatically upon completion of the cleaning protocol, for example, or upon detachment of the hub 108 from the device 100. In such an embodiment, the ejected cap is collected from the device 100 by the clinician and is then disposed.

As shown in FIG. 1A, in some embodiments, the attachment mechanism 104 includes jaws 112a, 112b, which define an opening 114 into which the hub 108 is insertable and held during use. Although two jaws are shown in this figure, in other embodiments the attachment mechanism may include one jaw or more than two jaws for securing the hub 108 to the device 100. The attachment mechanism also may include elements other than the illustrated jaws for securing the hub 108 to the device 100. In some embodiments, the device 100 and the attachment mechanism 104 are designed to prevent contamination of the hub 108 during the cleaning process (e.g., as might occur through handling or by placing the unit on a patient or bed or by splashing fluids).

As will be appreciated, the attachment mechanism 104 may be adjustable and configured to enable attachment of hubs 108 from different manufacturers. For example, when the jaws 112a, 112b are in an opened position, the opening 114 may be sized to accommodate CVC hubs of different sizes. In such an embodiment, the attachment mechanism 104 is also configured so that the jaws 112a, 112b may be closed to clamp or lock the different hubs 108 to the device 100. In some embodiments, the attachment mechanism 104 may be disposable or may have a specific life time.

In some embodiments, the NC may be customized to include grooves or even a square/rectangular segment to prevent slippage of the NC within the device during the scrubbing process. This would be a customized NC for the device and may or may not be required for use.

Figure 1B:
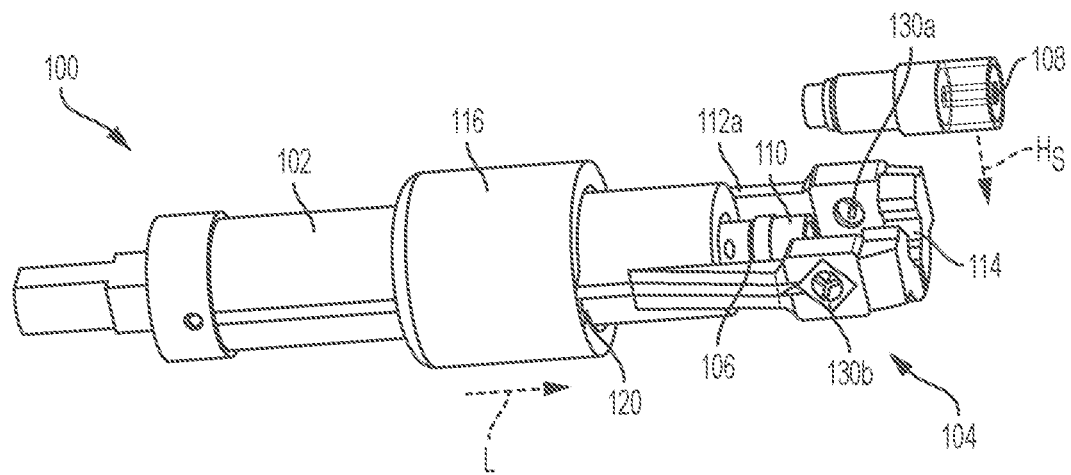
FIG. 1B is a perspective view of the cleaning device of FIG. 1A.

As shown in FIGS. 1A and 1B, embodiments in which the attachment mechanism 104 is in an opened position, the device 100 is configured to receive the hub 108 from various directions. For example, as shown in FIG. 1A, the hub may be inserted into the opening 114 from a forward end of the device (e.g., axially), as shown by the arrow labeled $H_T$. As shown in FIG. 1B, the hub 108 also may be inserted into the opening 114 from a side of the device, as shown by the arrow labeled $H_S$.

In some embodiments, the device 100 includes a hub locking mechanism, which cooperates with the attachment mechanism 104 to clamp or lock the hub 108 to the device and to remain locked during the cleaning protocol. In one embodiment, as shown in FIGS. 1A and 1B, the hub locking mechanism includes a sliding lock 116, which is positioned around an exterior surface of the body 102. In these embodiments, the lock 116 moves backwards and forwards to move the jaws 112a, 112b into opened and closed positions, respectively. As shown in FIGS. 1A and 1B, when the lock 116 is in a retracted position, the jaws 112a, 112b are in the opened or unlocked position.

Figure 2:
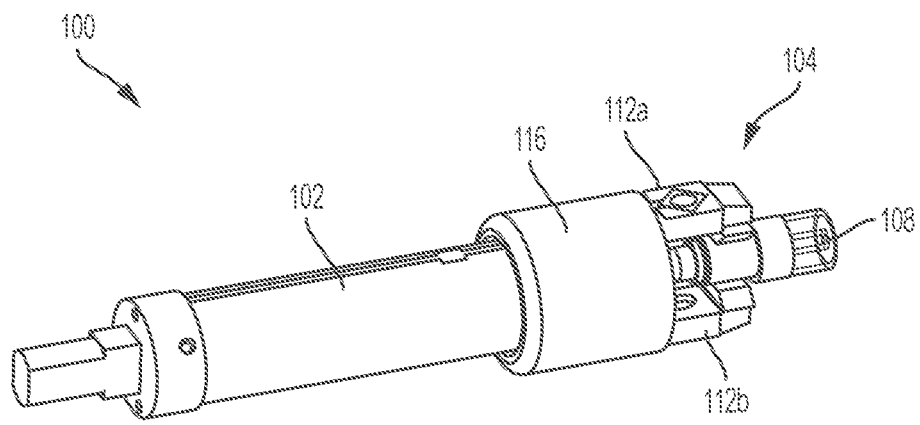
FIG. 2 is a perspective view of the cleaning device of FIG. 1A with the device engaged with the hub.

To clamp or lock the jaws 112a, 112b around the hub 108, the lock 116 may be moved in a forward direction, as shown by the arrow labeled L. During forward travel, the lock 116 contacts a distal end 118a, 118b of each jaw 112a, 112b, causing the jaws to move closer to one another (see, e.g., the arrows labeled $J_a$ and $J_b$), and then moves on top of the jaws 112a, 112b. FIG. 2 illustrates an example in which the lock 116 has captured the jaws 112a, 112b, with the jaws 112a, 112b in the locked position. As shown in FIG. 1B, in some embodiments, the lock 116 includes grooves or tracks 120 into which the jaws are inserted when the lock 116 captures the jaws 112a, 112b, preventing both rotational movement during scrubbing and axial movement during NC connection.

In some embodiments, the device 100 is configured such that the jaws 112a, 112b remained locked and clamped during the entire cleaning protocol. As will be appreciated, the jaws 112a, 112b may be biased in the opened position such that retraction of the lock 116 (e.g., in a direction opposite the arrow labeled L) causes the jaws 112a, 112b to move away from each other (e.g., in directions opposite the arrows labeled $J_a$ and $J_b$) and return to the opened position.

Figure 3:
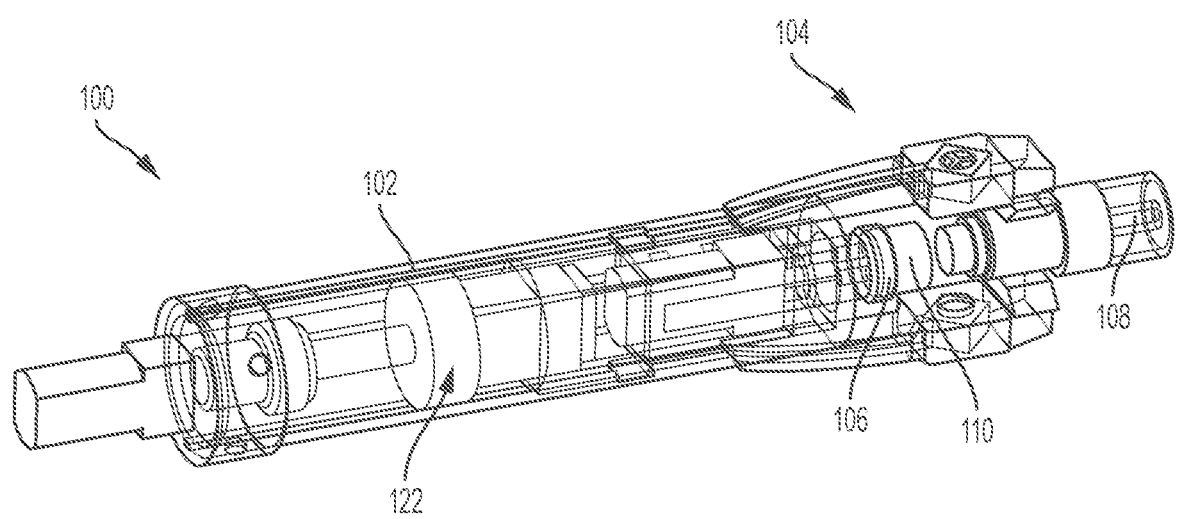
FIG. 3 is a perspective phantom view of a cleaning device according to one embodiment.
Figure 4A:
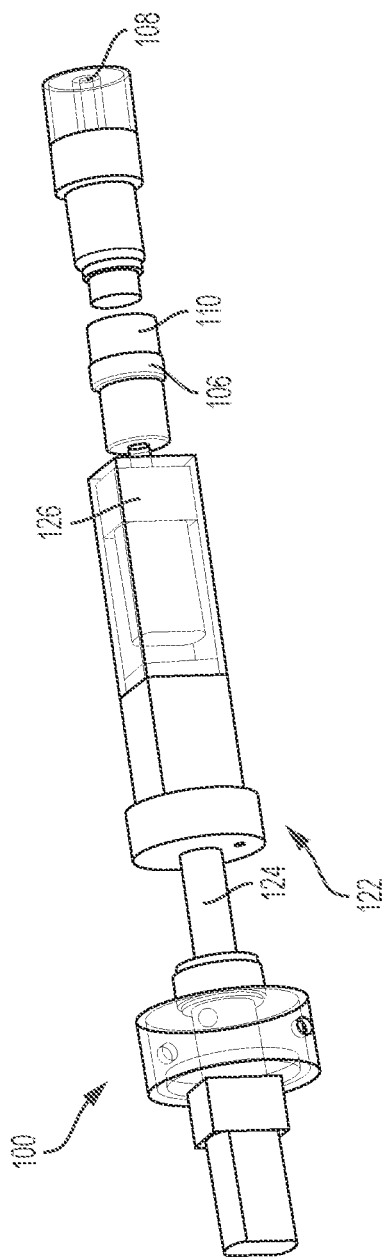
FIG. 4A is a perspective view of a portion of the cleaning device of FIG. 3 disengaged from a hub.
Figure 4B:
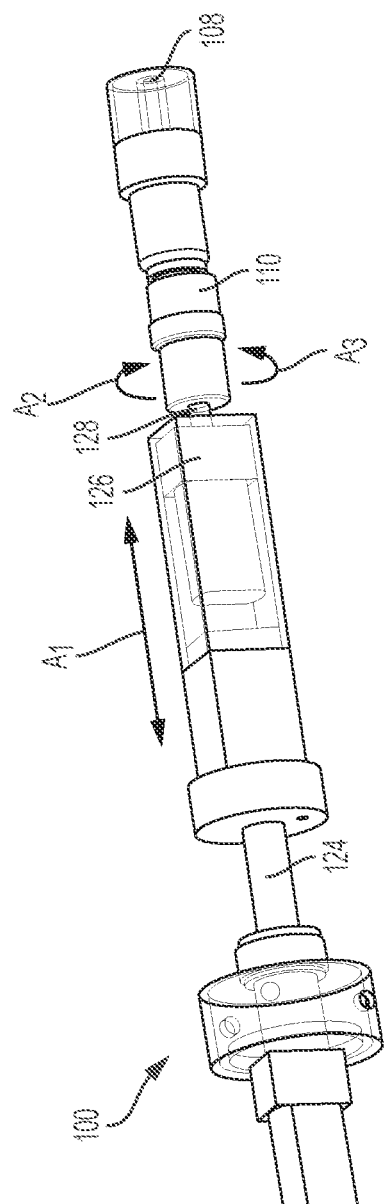
FIG. 4B is a perspective view of the cleaning device of FIG. 3 engaged with a hub.

As previously described, the device 100 is configured so that the cleaning cap 110 may be translated and rotated with respect to the hub 108 to clean the hub 108. FIGS. 3 and 4 illustrated examples of an assembly 122 that may be used to rotate and translate the cleaning cap 110. In some embodiments, as shown in FIG. 3, the assembly 122 is housed within the body 102 of the device 100. As shown in FIG. 4A, in one embodiment, the assembly 122 has a first actuator 124, such as a linear actuator, which is configured to translate the cap 110 with respect to the hub 108. As shown in FIG. 4B, an embodiment in which the cap 110 is advanced and engaged with the hub 108, the first actuator 124 moves back and forth, as shown by the arrow labeled $A_1$, which moves the cap 110 backwards and forwards. In another embodiment, as shown in FIG. 4A, the assembly 122 has a second actuator 126, such as a geared or motored actuator, which is configured to rotate the cap 110 with respect to the hub 108. As shown by the arrows labeled $A_2$ and $A_3$ in FIG. 4B, the second actuator 126 may rotate the cap 110 clockwise and counterclockwise, respectively, or may vibrate the cap. As should be appreciated, although linear and gear or motored actuators are shown in these embodiments for translating and rotating the cap, respectively, other types of actuators may be used in other embodiments. In some embodiments, the assembly may include only the second actuator 126, with the translation actuation being performed manually.

In some embodiments, the device 100 includes a blower such as a fan for blowing air onto the hub 108 to expedite the drying of (e.g., the evaporation of) the cleaning solution used to clean the hub 108. For purposes herein, a cleaning solution may include a disinfecting substance, an antiseptic liquid or another substance suitable for cleaning the hub. As shown in FIG. 1B, in one embodiment, fans 130a, 130b are located on each of the jaws 112a, 112b. As will be appreciated, the device 100 also may have only one fan or may have more than two fans in other embodiments. In some embodiments, the fans 130a, 130b are configured to circulate ambient air. In some embodiments, filters may be provided to purify the ambient air prior to blowing the air onto the hub 108. In other embodiments, to minimize contamination, the device 100 includes pressurized gas capsules (not shown) filled with air or carbon dioxide, for example. In these embodiments, the gas in the pressurized capsules is blown onto the hub 108 to dry the hub 108. As will be appreciated, the pressurized gas capsules (not shown) may be removably attachable to the device 100 such that new capsules (not shown) may be inserted once the prior capsules are empty.

Although fans 130*a*, 130*b* are shown in FIG. 1A for drying the hub 108 after cleaning (e.g., scrubbing) by the cleaning cap 110, it should be appreciated that other drying elements may be used in place of or in addition to the fans 130*a*, 130*b*. For example, in some embodiments, the device 100 includes a heater for drying the cleaning solution. The device also may include a vacuum that is applied to a sealed cleaning compartment to produce accelerated evaporation without exposure to the surrounding air. For example, in one embodiment, the lock 116 may be configured to create a seal around a base of the hub 108 such that negative pressure can develop around the hub 108. In such an embodiment, the vacuum may be applied by using fans integrated in the device as well as by using a tube attached to a vacuum line available in the patient's hospital room.

In another embodiment, the hub 108 may be dried by using a light to heat the cap 110 slightly and cause evaporation. For example, in one embodiment, specially designed pigments may be incorporated into the cleaning solution (e.g., an antiseptic solution), the pigments being able to absorb specific wavelengths to speed up the drying time.

As described above, the device 100 includes a cleaning cap 110 that is translated and rotated with respect to the hub 108 to clean the hub. As also previously described, the cap 110 is configured to have compliance between the cap and the hub 108. In some embodiments, the shape of the cap corresponds to the shape of the hub. As shown in FIG. 5A, in one embodiment, the cap 110 includes a cap body 132 and an internal cleaning member 134. In some embodiments, the cap body 132 is a rigid body, although the cap body 132 may have other suitable configurations.

Figure 5C:
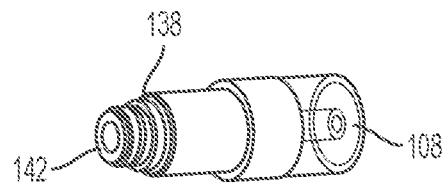
FIG. 5C is a perspective view of an exemplary catheter hub according to one embodiment.
Figure 5D:
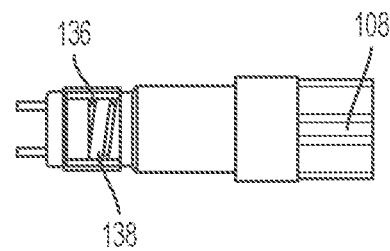
FIG. 5D is a side view of the cleaning cap of FIG. 5A shown in partial cutaway engaged with the hub of FIG. 5C according to one embodiment.

In some embodiments, the cleaning member 134 includes threads 136, or other helical member which correspond to the threads 138 on the hub 108 (see FIG. 5C). For example, the geometry or shape of the cap threads 136 may match the geometry or shape of the hub threads 138. As shown in FIG. 5D, as the cap 110 is rotated, the cap threads 136 engage with the hub threads 138 for cleaning. In some embodiments, axial and lateral compression of the cleaning member creates friction and ensures proper cleaning of the side surfaces and threads. The cap 110 may be rotated until the cap 110 is completely threaded onto the hub 108.

In some embodiments, the cap 110 is configured such that the cap threads 136 may snap or jump over the hub threads 138 during the bidirectional linear and rotary motion of the cap 110. In some embodiments, the cap 110 itself is configured to flex outwardly (e.g., radially) and away from the hub, as shown by the arrow labeled C in FIG. 5A, to allow the cap and thus cleaning member to move over the hub threads 138. In some embodiments, the cap 110 (e.g., the cap body 132 and cleaning member 134) has circumferential gaps 140, which produce this radial compliance. In other embodiments, the radial compliance is accomplished by having a cleaning member 134 that is elastic and itself compliant and allows compression and expansion as the cap threads jump over the hub threads. In some embodiments, the cleaning member 134 includes a foam material, while in other embodiments the cleaning member 134 may include a fabric material or another suitable material. In some embodiments, the cleaning member 134 is soaked or saturated with a cleaning solution (e.g., a disinfecting substance or an antiseptic liquid).

Figure 5E:
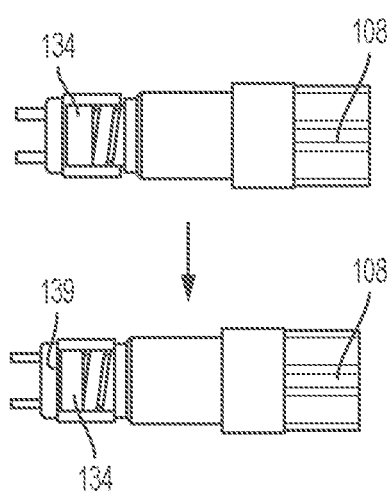
FIG. 5E are side views of the cleaning cap of FIG. 5A shown in partial cutaway engaged with the hub of FIG. 5C according to another embodiment.

In some embodiments, the cap is also configured to clean the hub tip 142 (see FIG. 5C). In such embodiments, the cap 110 is configured so that the shape of the cap corresponds with the shape of the hub tip 142. As shown in FIG. 5E at bottom, in some embodiments, when the cap 110 is translated in a forward direction (e.g., when the cap 110 is threaded on the hub or when the cap threads 136 jump over the hub threads 138), the cleaning member 134 at a bottom 139 of the cap 110 may be compressed. This compression may allow for scrubbing of the hub tip 142. Compression of the cleaning member also may release the stored antiseptic liquid from the cleaning member 134.

Figure 6A:
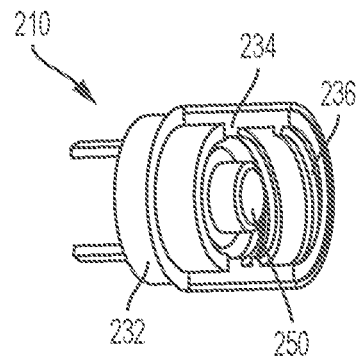
FIG. 6A is a perspective view of a cleaning cap shown in partial cutaway according to another embodiment.
Figure 6B:
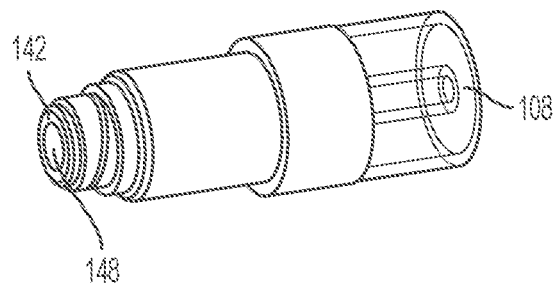
FIG. 6B is a perspective view of a catheter hub.
Figure 6C:
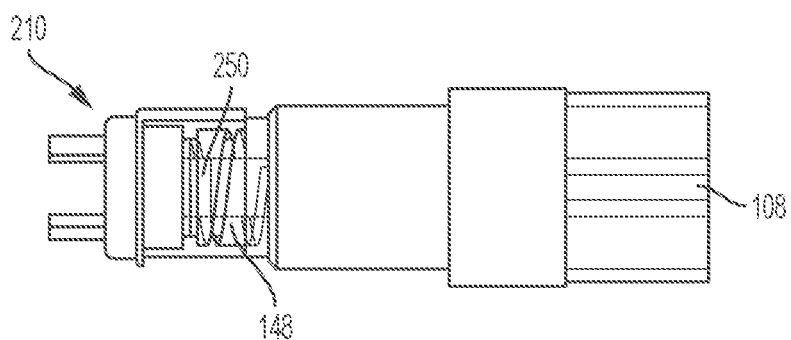
FIG. 6C is a side view of the cleaning cap of FIG. 6A shown in phantom engaged with the hub of FIG. 6B.

FIG. 6A illustrates another example of the cleaning cap 210, which may be configured for additional cleaning of the hub tip 142, namely cleaning of the valve 148 located at the hub tip 142 (see FIG. 6B). As shown in FIG. 6A, the cleaning member 234 may include an intra-valve cleaning pin 250, which engages with the valve 148 on the hub tip 142 when the cap 210 is translated in the forward direction. As illustrated in FIG. 6C, for example, the valve 148 may be pushed inwardly by the cleaning pin 250 when the hub 108 is engaged with the cap 210.

Although a cylindrical cleaning pin 250 is shown in this embodiment, in other embodiments, the pin 250 may have other geometries. For example, in another embodiment, the pin 250 may have a hexagonal cross section. As will be further appreciated, the cap 210 may have other structures for cleaning the valve 148 of the hub tip 142. For example, a raised ring (e.g., a ring similar in dimension to the threads 236 on the cleaning member 234) could be used to rotate in a groove surrounding the valve 148 of the hub tip 142.

Figure 7A:
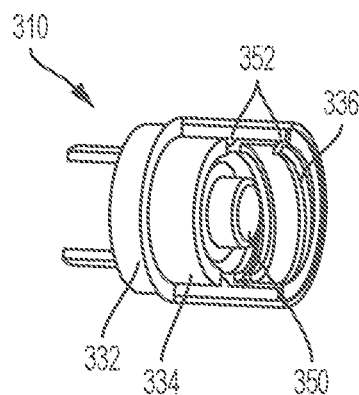
FIG. 7A is a perspective view of a cleaning cap shown in partial cutaway according to still another embodiment.
Figure 7B:
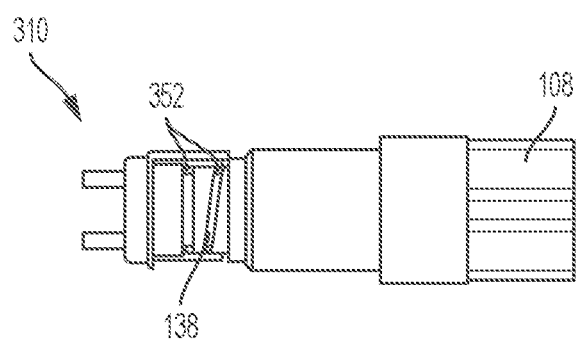
FIG. 7B is a side view of the cleaning cap of FIG. 7A shown in partial cutaway engaged with a hub.

FIGS. 7A and 7B illustrate a cleaning cap 310 according to another embodiment. Similar to the cleaning caps previously described, the cleaning cap 310 shown in FIG. 7A may include a cap body 332 and a cleaning member 334. The cleaning member also may include threads 336 for engaging with the hub threads 138 and a cleaning pin 350 for engaging with the valve 148 of the hub tip 142. In the embodiment shown in FIG. 7A, the cleaning cap 310 also has threads 352 formed in the cap body 332. In some embodiment, as shown in FIG. 7B, the cap body threads 352 ensure safe locking of the cap 310 to the hub threads 138 during scrubbing. In such an embodiment, the location of the cap body threads 352 corresponds with the location of the threads 336 in the cleaning member 334.

Figure 8:
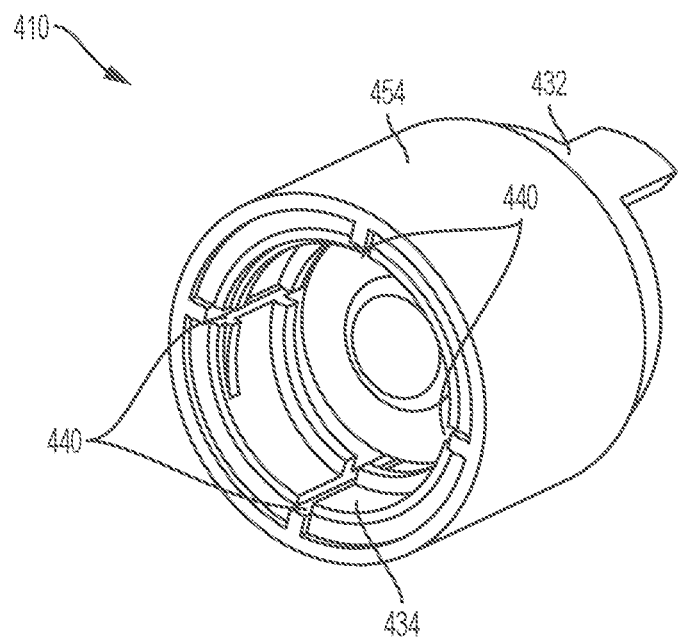
FIG. 8 is a perspective view of a cleaning cap according to another embodiment.

FIG. 8 illustrates still another example of a cleaning cap 410 used to clean the hub 108. In some embodiments, as shown in FIG. 8, the cap includes an elastic body 454 that covers the circumferential gaps 440 around the cap 410 (e.g., the circumferential gaps 440 in the cap body 432 and in the cleaning member 434). As previously described, the cap body 432 may be a rigid structure. In some embodiments, the elastic body 454 may improve compliance as well as protects the antiseptic liquid during packaging. In some embodiments, in addition to assuring compliance of the cap 410, the circumferential gaps 440 also act as antiseptic release pathways to ensure thorough distribution of the cleaning solution around the threaded region. In some embodiments, when the hub tip (not shown) is pushed against the cleaning member 434 at a bottom of the cap 410, the reserved antiseptic liquid can be released and flow around the circumference through the pathway.

As previously described, the device 100 may be configured to run a cleaning protocol to clean the hub 108. In such embodiments, the device may include a controller (or multiple controllers) for controlling the device (e.g., the actuators) and running the cleaning protocol (e.g., the unit programming). In some embodiments, the cleaning protocol includes a target time for scrubbing the hub 108 with the cap 110 (e.g., by translating and rotating the cap 110 with respect to the hub 108) and a target time for drying the hub 108 (e.g., a run time of the fan after scrubbing). The cleaning protocol also may include a target number of revolutions of the cap 110 (e.g., in each or both of the clockwise and counterclockwise directions). In other embodiments, the controller is configured to control the cleaning and drying parameters of the device 100, such as the scrubbing motion and speed or fan run times.

In some embodiments, the device 100 includes a timer (not shown). In some embodiments, the timer is used to time the duration of scrubbing or drying. In some embodiments, the device may be configured to turn off once a target period of time has elapsed (e.g., the time of the cleaning protocol). In some embodiments, this creates consistency in cleaning the hubs and also allows a clinician to attach the device to the hub and walk away while the cleaning protocol is being completed.

Figure 50:
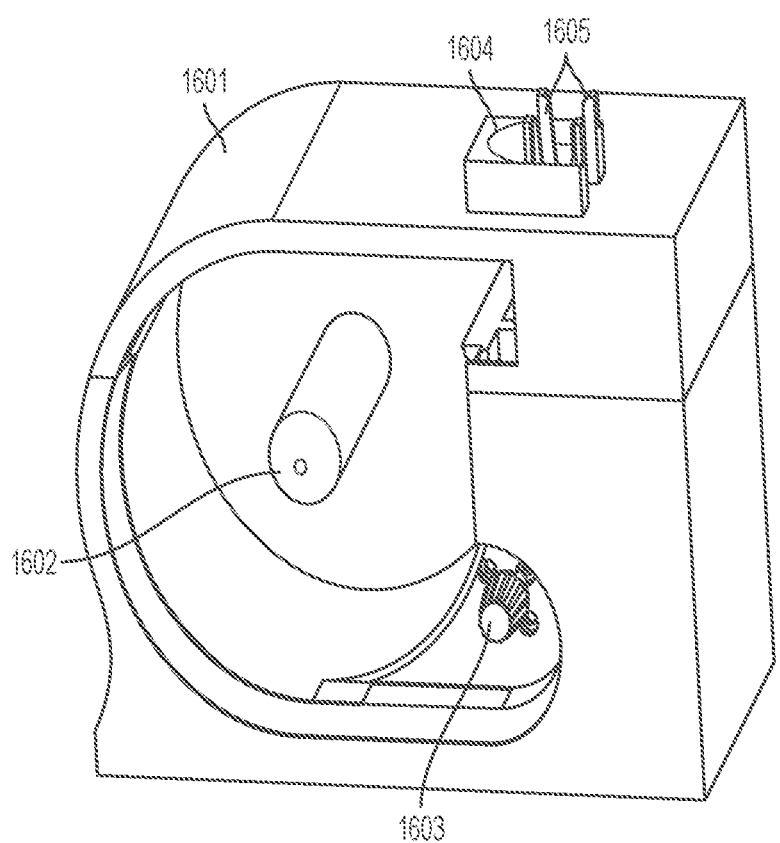
FIG. 50 is a perspective view of a charging station according to one embodiment.

In some embodiments, the device 100 is a cordless rechargeable device. In such an embodiment, the device 100 may include a rechargeable power source (e.g., a rechargeable battery). As will be appreciated, the device 100 may be coupled to a charging station (see, e.g., FIG. 50), for example after the completion of the cleaning protocol, to recharge the power source. In some embodiments, the charging station also may be configured to disinfect the device 100. As will be appreciated, in some embodiments, the device 100 also may plugged into a wall outlet for power (e.g., not rechargeable).

In some embodiments, the device 100 includes wired or wireless data transfer capabilities, which may enable unit programming, tracking of use and integration with ICU data systems. For example, the device 100 may include integrated sensors (not shown), such as an RFID reader, which may record the patient ID and/or nurse ID for each use. In some embodiments, the device 100 also has data storage capabilities. For example, data may be stored on the device until the device is plugged into a computer or is coupled to the charging station. In other embodiments, the data may be transmitted directly (e.g., wirelessly) to a computer after the cleaning protocol has ended. In some embodiments, this wireless confirmation of cleaning may be required to enter data into the medication administration record, ensuring compliance with cleansing practices. Although the embodiments shown and described include cleaning of the hub using a cleaning cap, other cleaning techniques also may be used with the device 100. For example, in some embodiments, the device 100 also may include a UV lamp, a LED light, or a steam generator for additional or alternative cleaning. In other embodiments, the device 100 may include an ultrasonic generator or other vibration source for additional scrubbing as well as contact and penetration of the cleaning solution. In these embodiments, the ultrasonic generator or vibration source may be located at a distal end of the second actuator 126.

In some embodiments, the device 100 includes an indicator (not shown) for alerting the clinician when the cleaning protocol has finished. The indicator also may alert the clinician when there is an error during the use of the device, for example an error caused by a device malfunction or by a user mistake (e.g., an improperly installed cap 106 or hub 108). In some embodiments, the indicator (not shown) may include a visual indication such as the illumination of an LED light on the device or an audible indication such as a beeping or buzzing sound.

In some embodiments, the device 100 includes a cleaning subassembly (not shown), that includes all of the components that contact the hub 108 during the cleaning protocol, and a main body (not shown). In such embodiments, the cleaning subassembly may include the jaws 112 and cap holder. The cleaning subassembly also may include the lock 116. In one embodiment, the main body includes the actuators, electronics and batteries, for example, that drive the cleaning protocol. The cleaning subassembly may be coupled to the main body via various coupling mechanisms (e.g., electrical and/or mechanical). For example, the cleaning subassembly may be coupled to the main body via linear or rotational motion using snap connectors (e.g., notched pins or slides) that may be released either by applying a force or by depressing a button. In some embodiments, the cleaning subassembly is detachable from the main body of the device 100. In such embodiments, a used cleaning subassembly may be removed from the device 100 in between patient visits and replaced with a sterile cleaning subassembly. As will be appreciated, the cleaning subassembly also may be substantially permanently coupled to the main body of the device 100.

According to another embodiment, a method of using the device 100 for cleaning a CVC hub is disclosed. The method includes inserting a hub into an opening defined by the jaws of an attachment mechanism and clamping or locking the jaws to secure the hub to the device. Forward travel of the slide lock 116 moves the jaws into the locked position. As previously described, the locking mechanism may be configured so that the jaws remain locked during the entire cleaning protocol. The method also includes inserting a cleaning cap 110 (e.g., manually or automatically) into the cap holder 106.

Once the cap 110 and hub 108 are attached to the device 100, the clinician may activate the device to clean the hub 108. If an error occurs during cleaning (e.g., the hub or cap are improperly attached or one of the actuators is unable to move the cap), the device may alert the clinician (e.g., visually or audibly) that the cleaning was not completed. Otherwise, the cap 110 is advanced to engage with the hub 108 and the first and second actuators translate and rotate the cap 110 relative to the hub 108. After a target number of revolutions of the cap 110 or after a target duration of time, the cap 110 is retracted and the fans, or other device, dry the cleaning solution applied to the hub. Once the drying has finished (e.g., after a target period of time), the indicator may alert the clinician that the cleaning of the hub 108 has finished.

Upon completion of the cleaning protocol, the device 100 may be unlocked and the hub 108 may be removed. A sterile cap may be then placed on the cleaned hub. The device may also facilitate placement of a sterile cap after cleaning and injection. For example, a two-part cartridge could include a cleaning cap and a sterile storage cap. Once the injection shown in FIG. 9 is complete, the device could automate installation of the sterile cap.

Figure 9A:
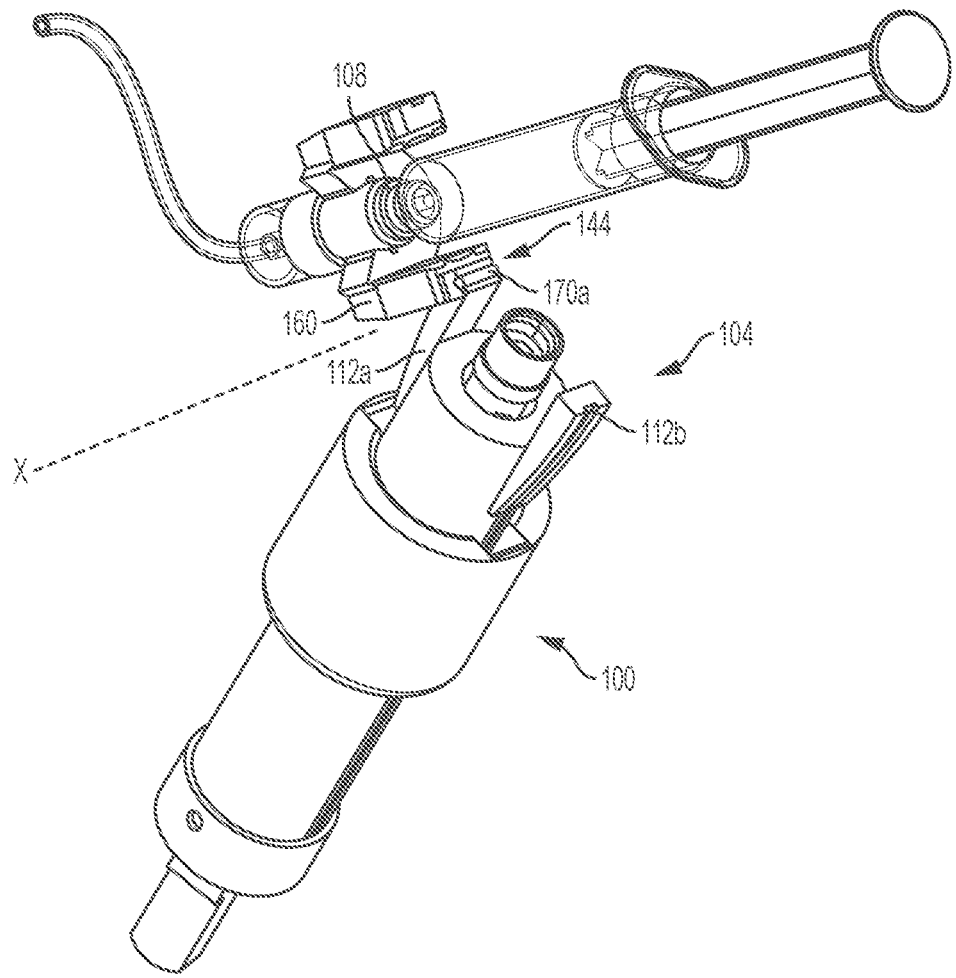
FIG. 9A is a perspective view of a cleaning device according to one embodiment.
Figure 9B:
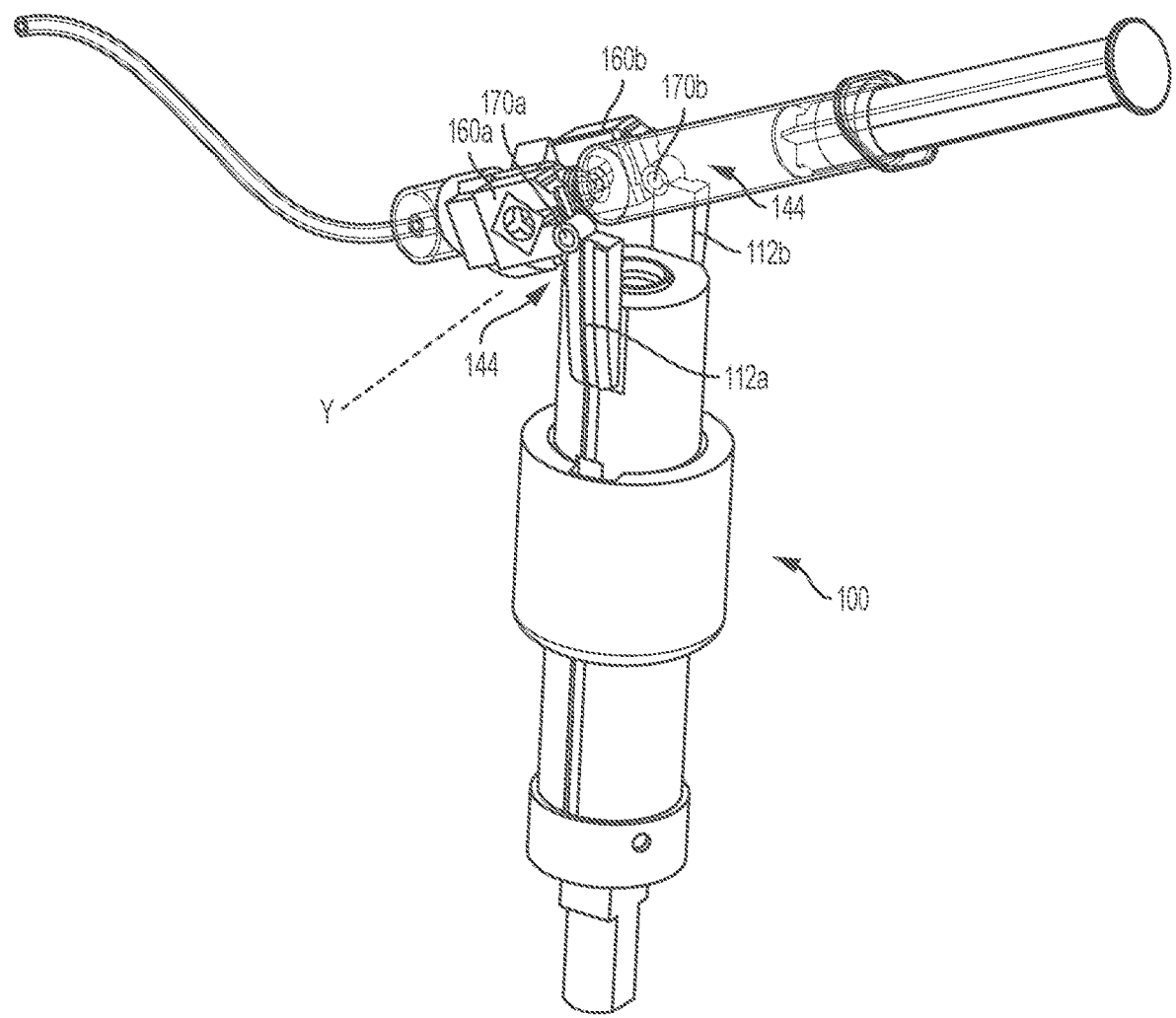
FIG. 9B is a perspective view of a cleaning device according to another embodiment.

In other embodiments, an injection may be administered at the hub. In one embodiment, the device 100 is completely disconnected from the hub prior to the injection. In other embodiments, the device 100 is configured to remain attached to the hub yet be moved to allow the injection. As shown in FIG. 9A, the device 100 may include a joint 144, which facilitates administration of the injection (e.g., by reducing the number of steps) and possibly reduces the chances of contamination. The joint 144 may be a part of the attachment mechanism 104. In one embodiment, the joint 144 is formed on a forward end of one of the jaws 112a, 112b and is coupled to an arm 160 of the hub 108. The joint 144 includes a hinge pin 170a that allows the device 100 to remain attached to the hub 108 while pivoting the device 100 away from the hub 108 and about an axis X, which extends along the hinge pin 170a and passes through the joint 144. Although only one arm 160 is shown hinged to one jaw 112a in FIG. 9A, the hub 108 also may include two arms 160a, 160b that are hinged to the two jaws 112a, 112b, respectively, via a hinge 144 having hinge pins 170a, 170b, as shown in FIG. 9B. In such an embodiment, the arms 112a, 112b rotate about an axis Y extending through the hinge pins 170a, 170b and between the jaws 112a, 112b. As will be appreciated, this pivoting may provide access to the hub for injection, while providing a convenient and sterile method for holding onto the hub.

FIGS. 11-32 illustrate another embodiment of a cleaning device 1001 used to automatically or semi-automatically clean a NC hub. As with other embodiments, the device 1001 includes an attachment mechanism, such as a clamp 1002, to attach and hold the hub (not shown) stationary with respect to the device 1001 while being cleaned (e.g., supporting a hands-free operation), and a cap holder 1005 for holding a cleaning cap 1004. In some embodiments, the cap 1004 is disposable.

Figure 11:
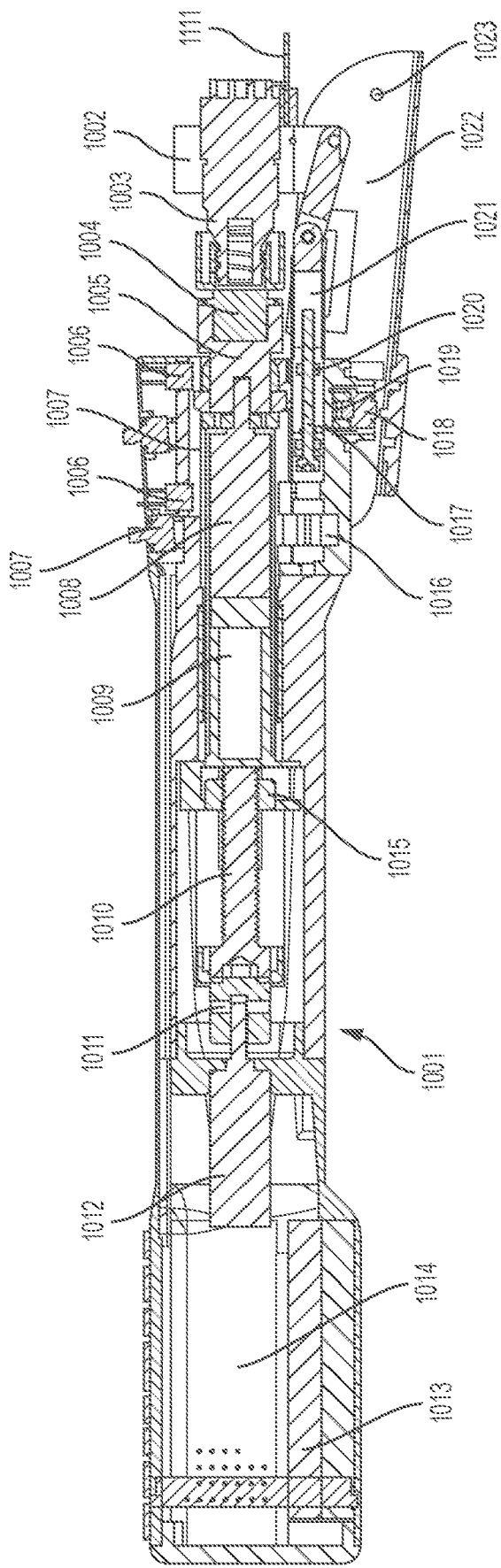
FIGS. 11 and 12 are side views of the cleaning device according to another embodiment.
Figure 13A:
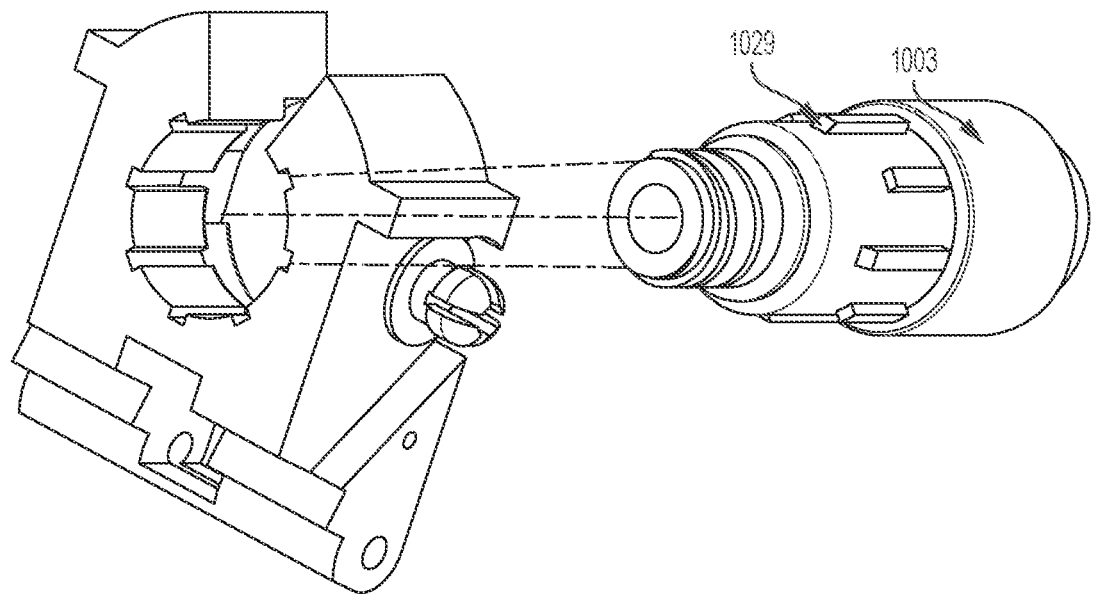
FIG. 13A is an exploded perspective view of a hub and clamp according to one embodiment.
Figure 13B:
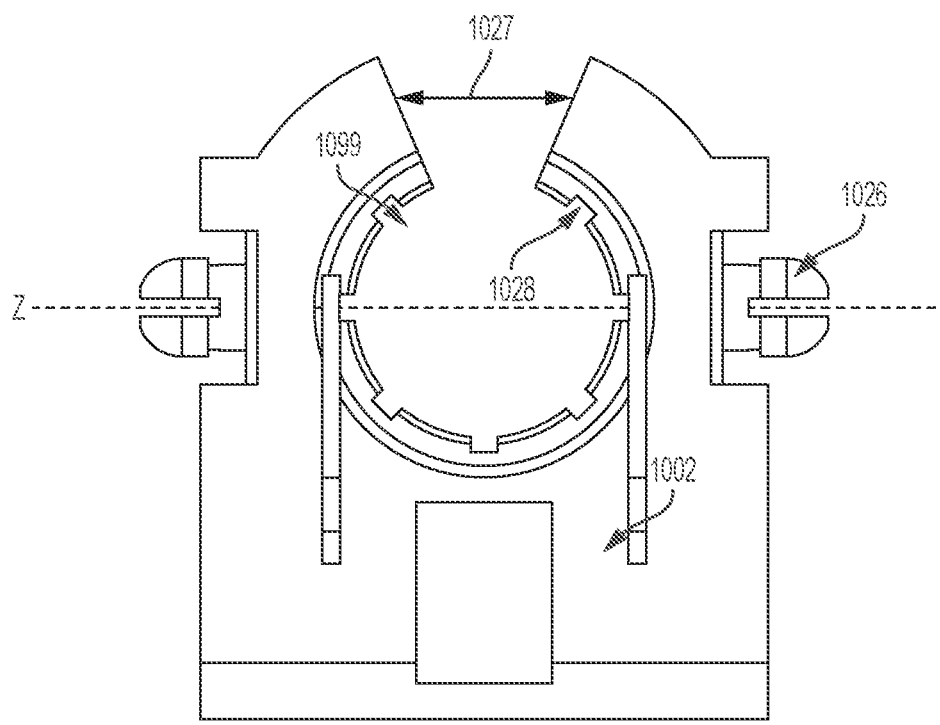
FIG. 13B is a front view of the clamp of FIG. 13A.

As shown in FIG. 11, the attachment mechanism may include a coupling such as clamp (2) to hold the hub to the device. As shown in FIGS. 13A and 13B, the clamp includes an opening 1099, into which the hub 1003 is inserted (e.g., snapped). The hub may be attached to the device by axial insertion. In some embodiments, a cover 1022 (see FIG. 11) may be included in the device to protect the hub from contamination while the device is left on the bed. For example, the device could be left on the bed while performing the cleaning process without the risk of contamination. As shown in FIG. 13B, the clamp 1002 may include a slot or gap 1027 to allow the hub to being removed with an attached tubing or permanent cap without the risk of recontamination.

The clamp 1002 may have a locking/ejecting mechanism which locks the hub in an axial direction to avoid ejection during the applied force while the hub being accessed. The locking/ejecting mechanism also may be designed to ejecting the hub after the cleaning protocol has finished.

Figure 19:
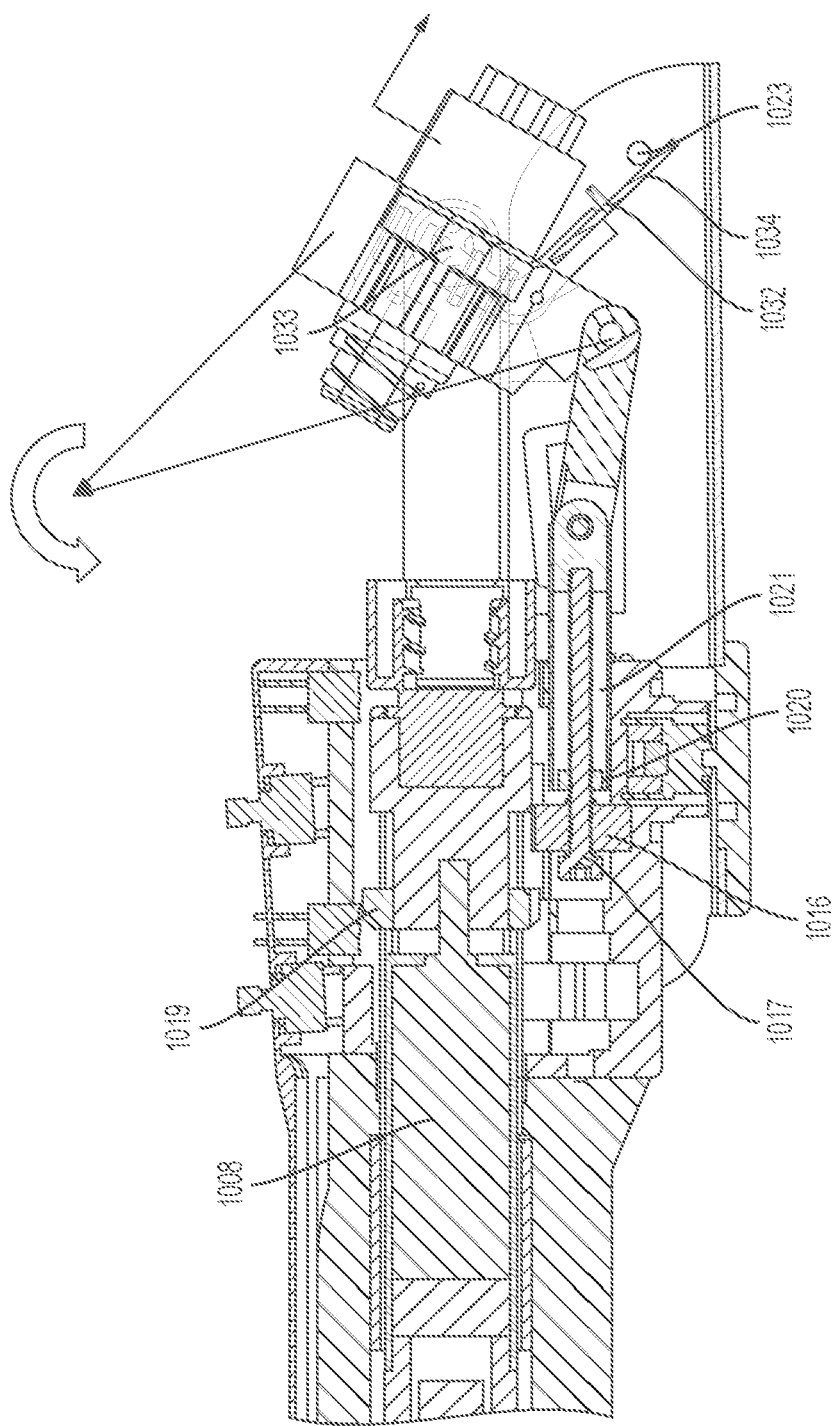
Figure 20:
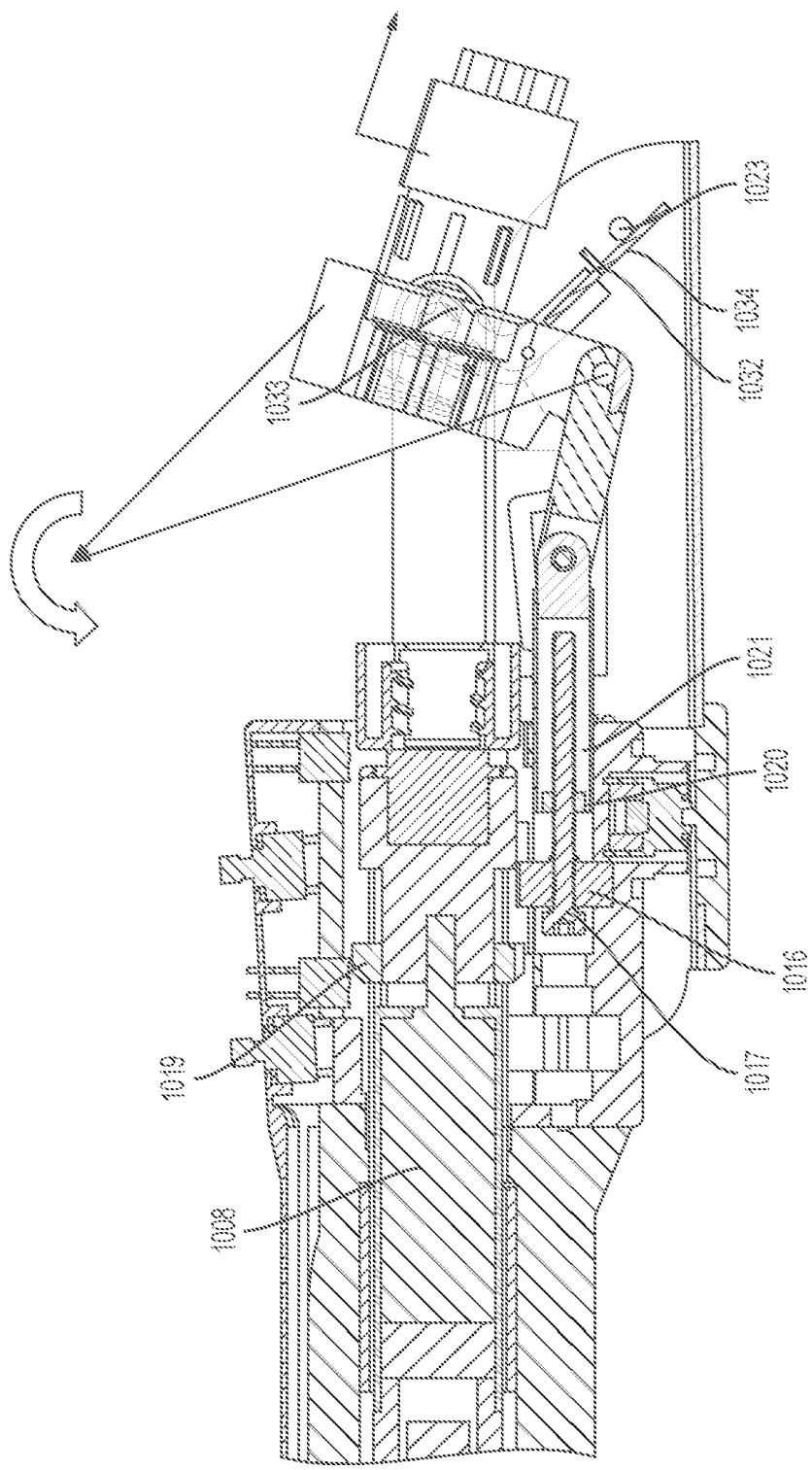
Figure 21:
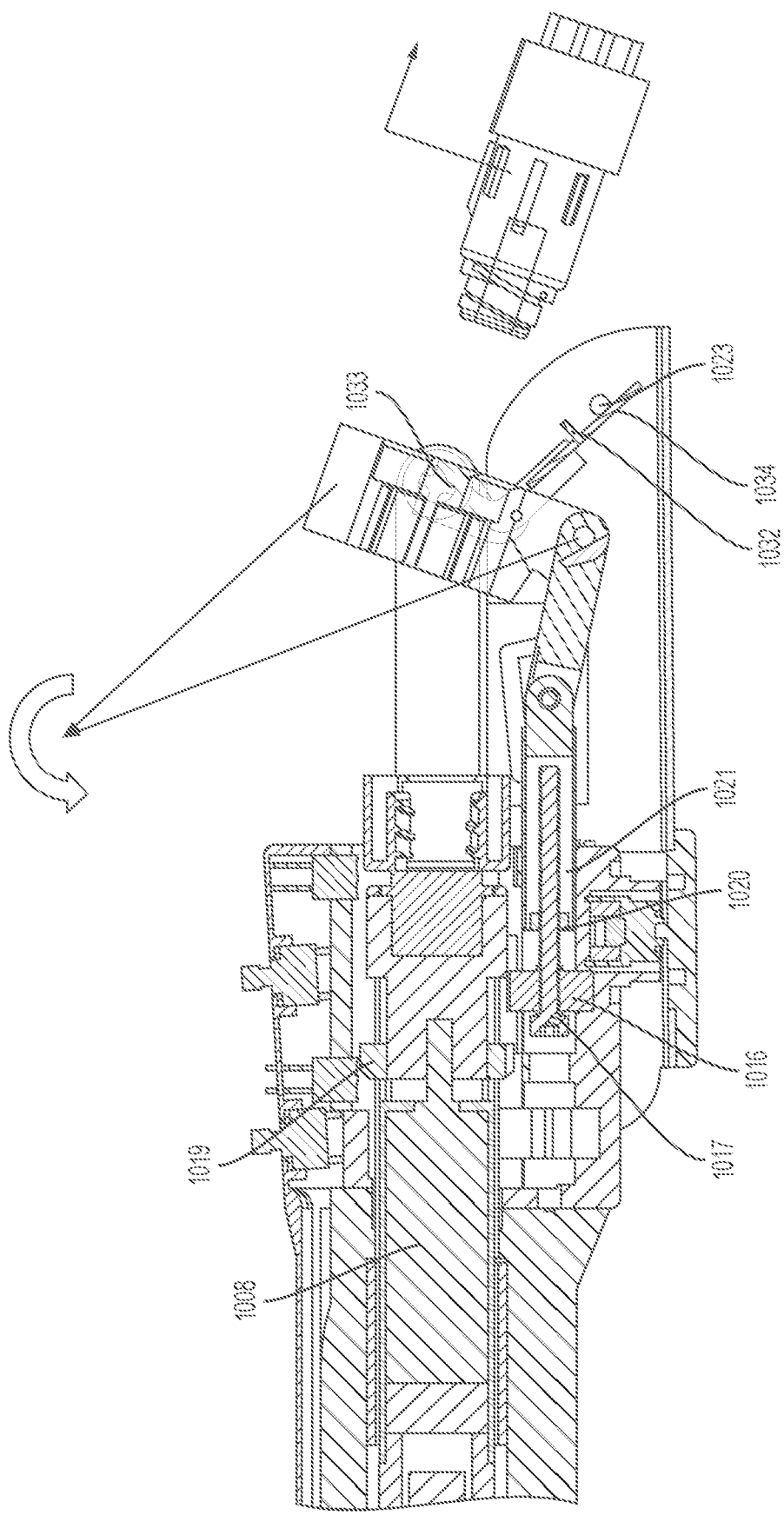
Figure 22:
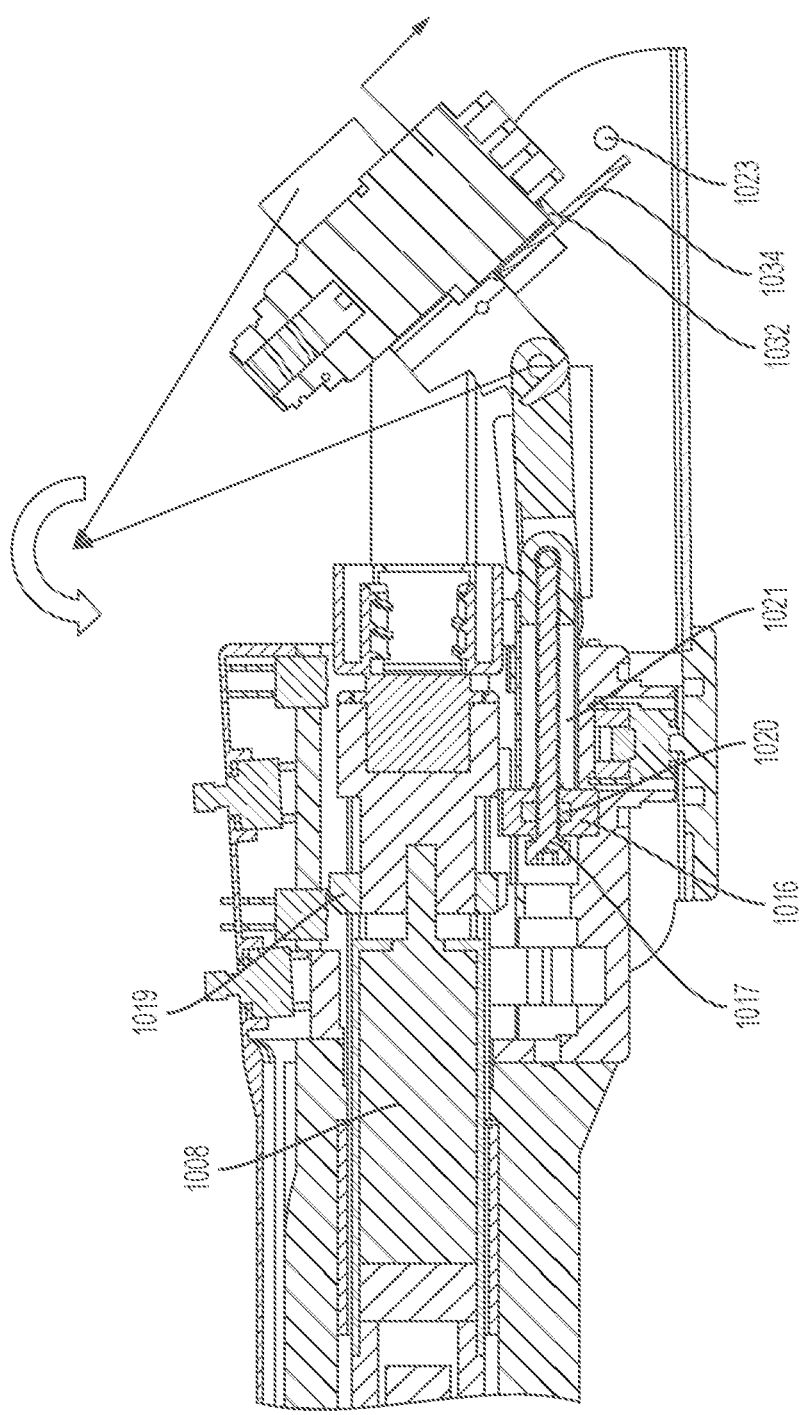
Figure 23:
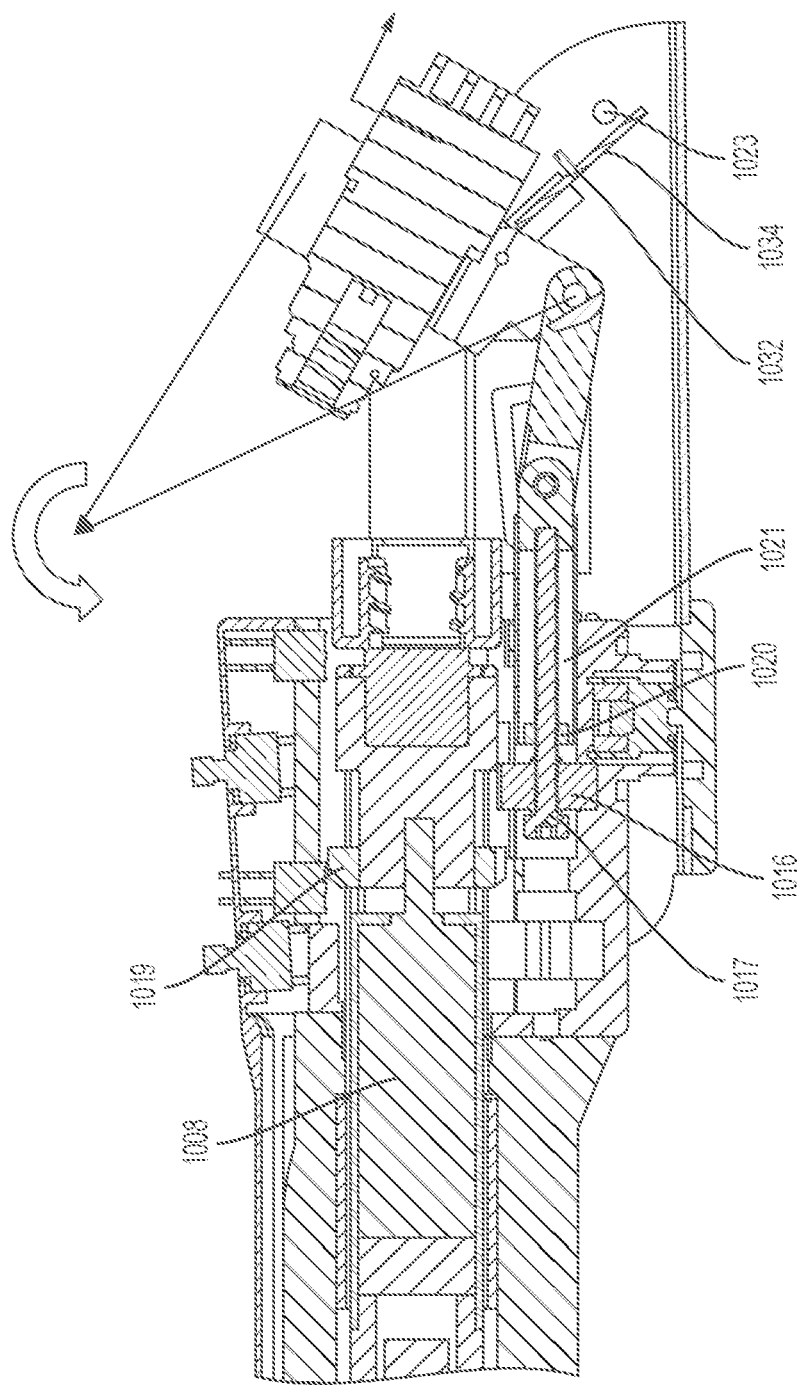
Figure 24:
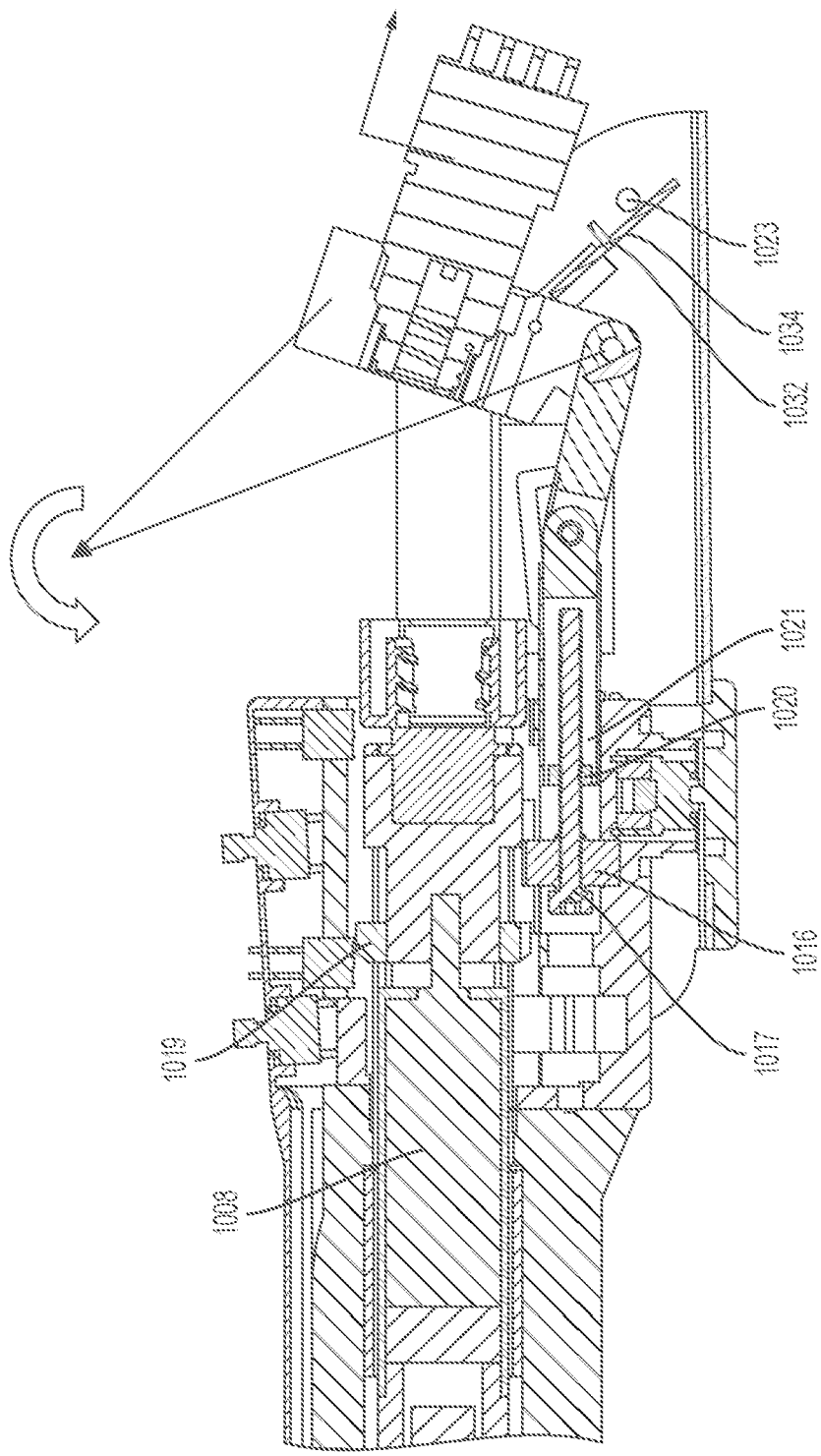
Figure 25:
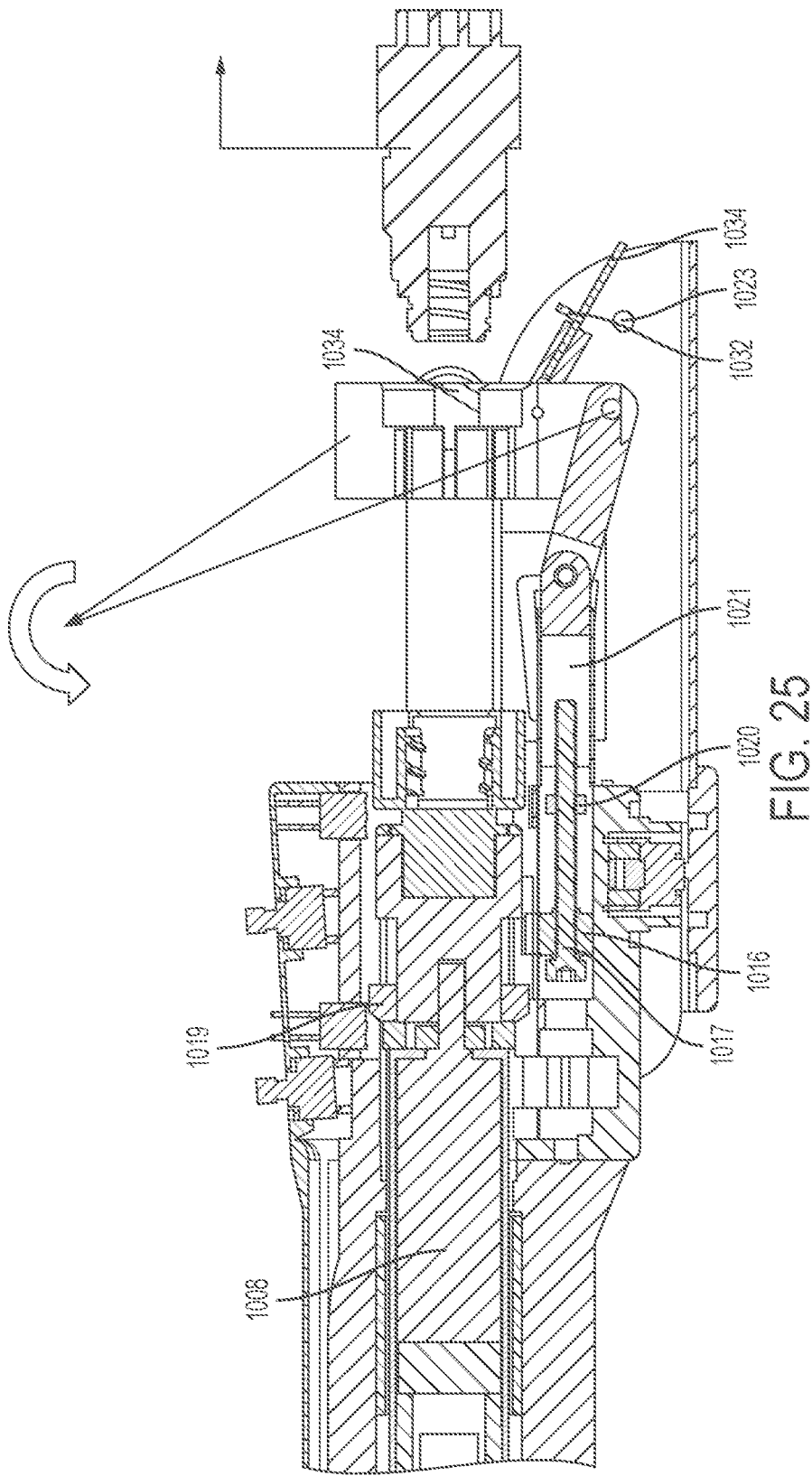
Figure 26:
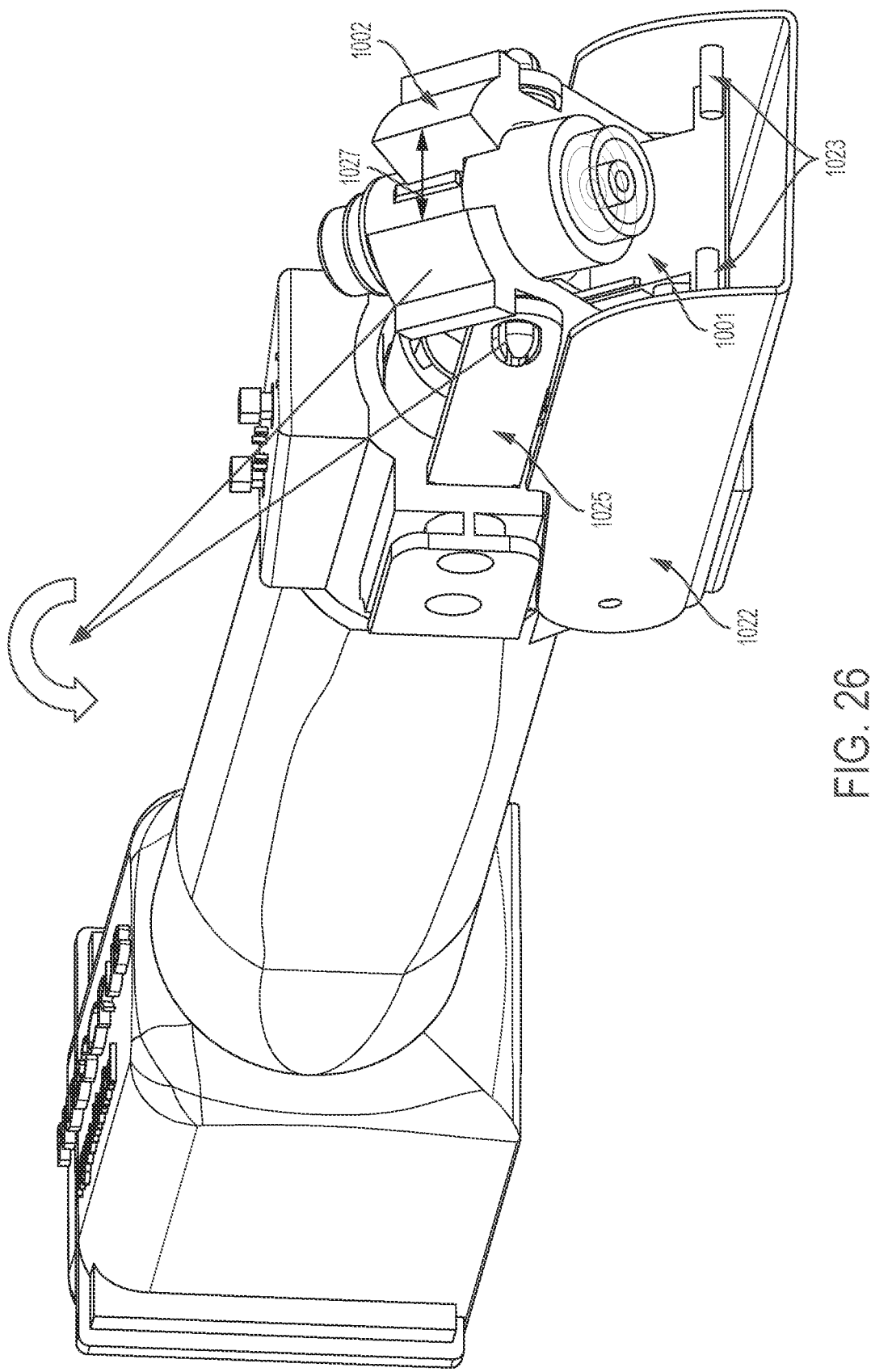
FIGS. 26-29 are perspective views of the cleaning device of FIGS. 14 and 15.
Figure 27:
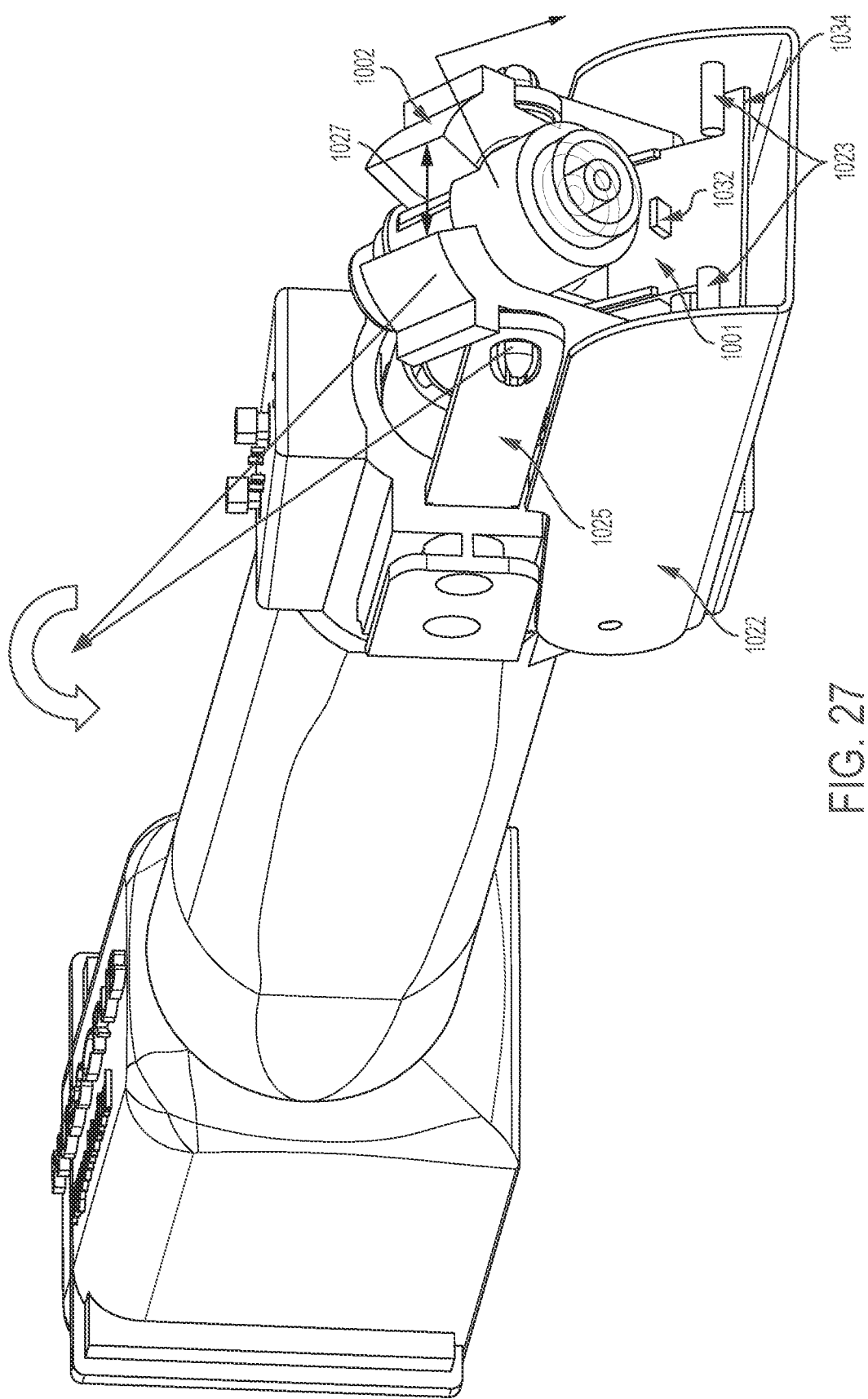
Figure 28:
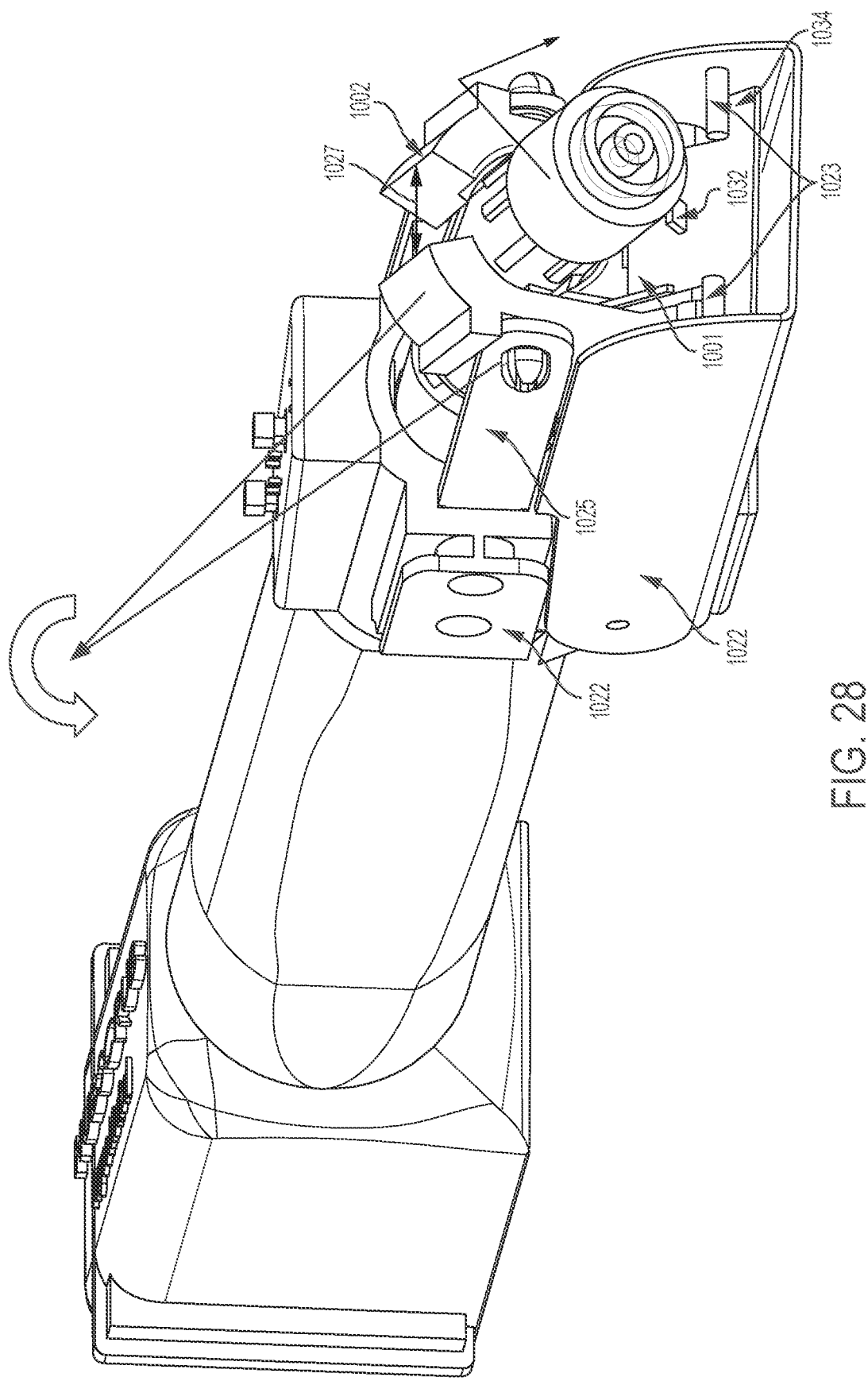
Figure 29:
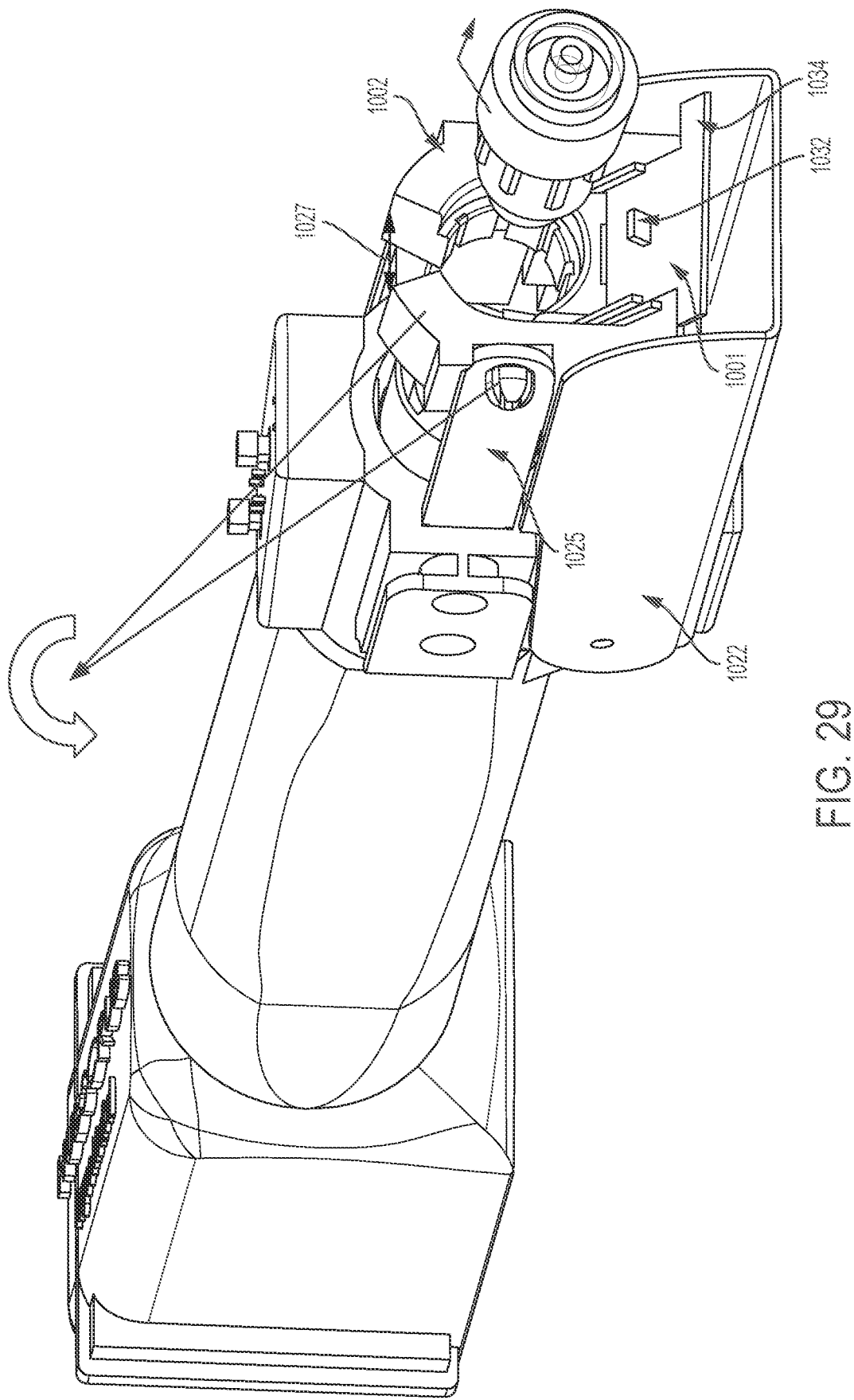
Figure 30:
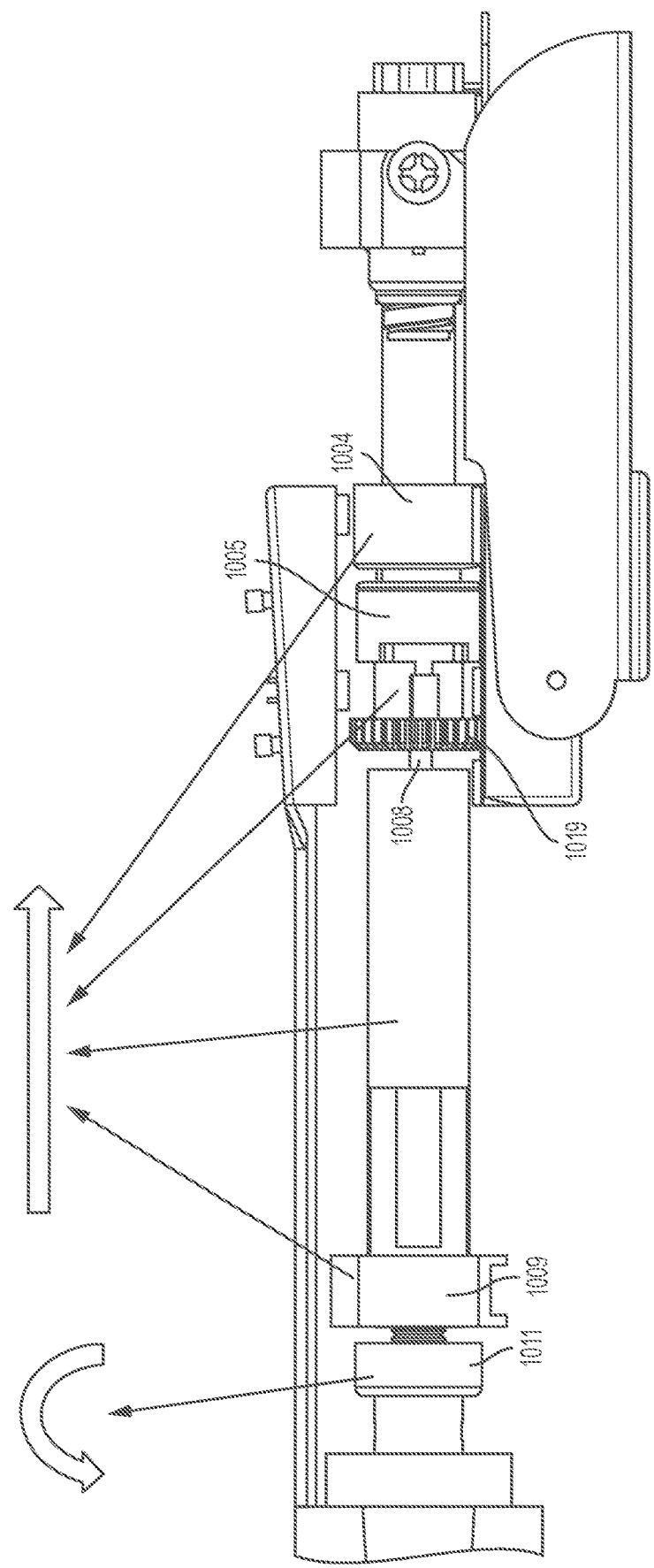
FIGS. 30-32 are side views of a portion of the cleaning device of FIGS. 14 and 15.
Figure 31:
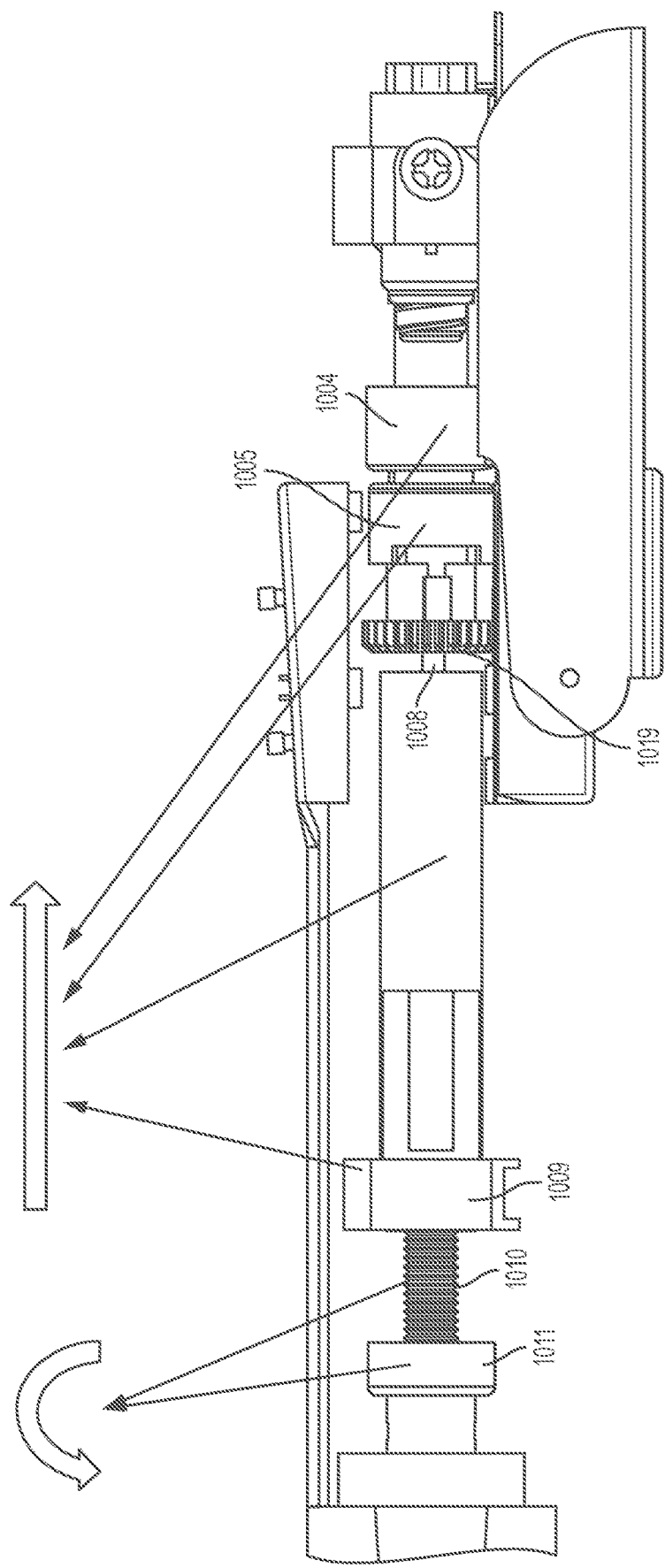
Figure 32:
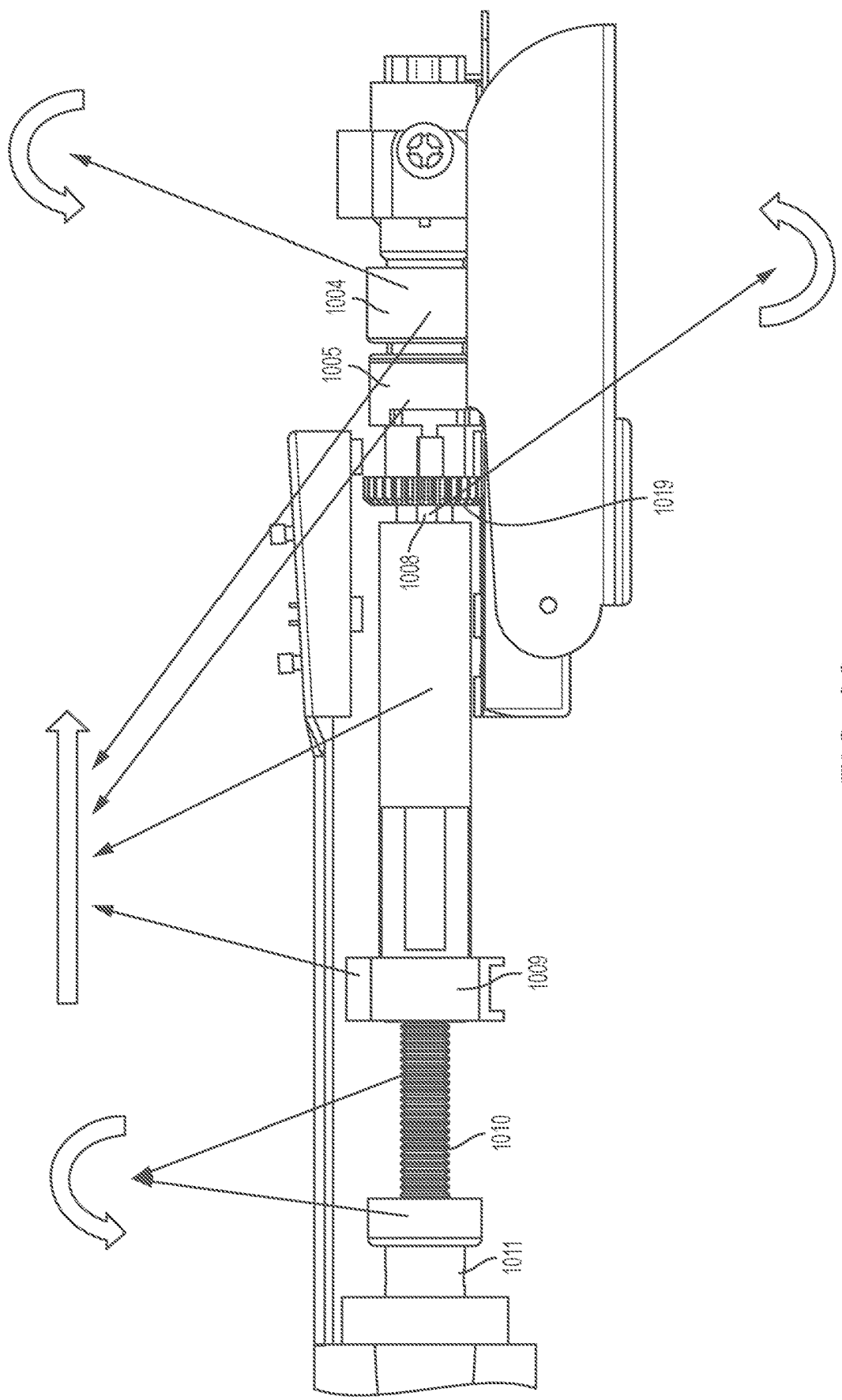
Figure 33:
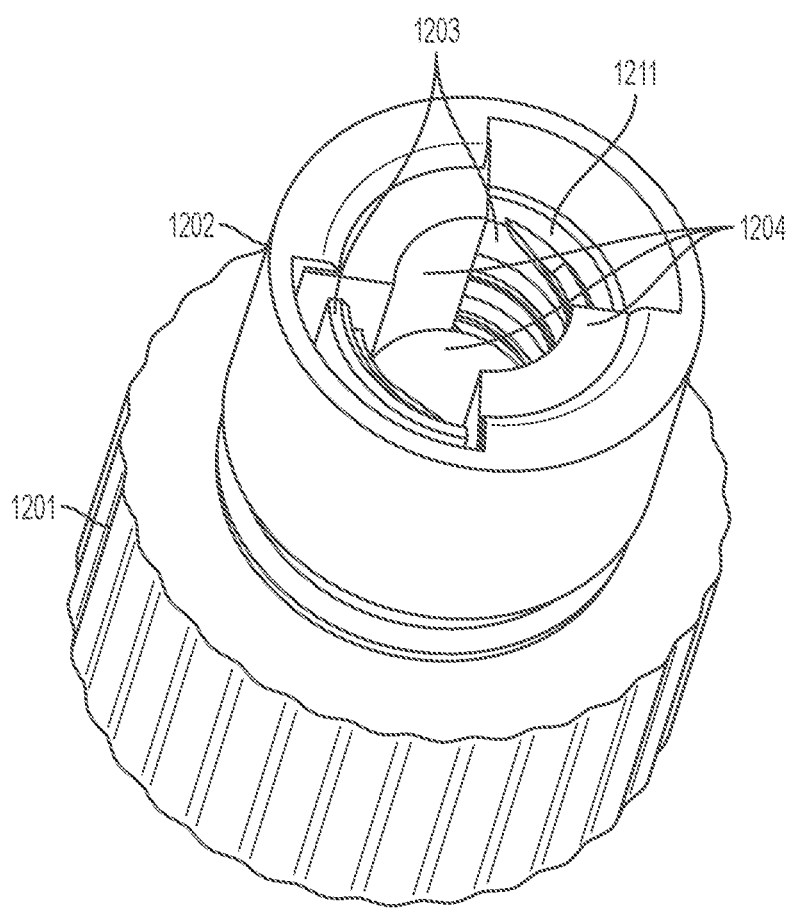
FIG. 33 is a perspective view of the cleaning cap according to one embodiment.
Figure 34:
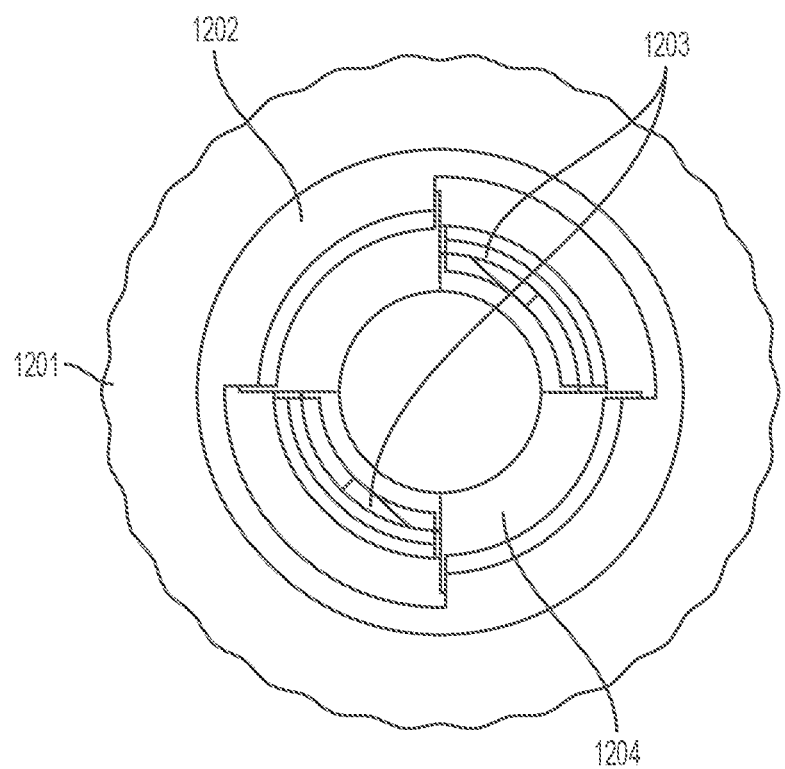
FIG. 34 is a top view of the cleaning cap of FIG. 33.
Figure 35B:
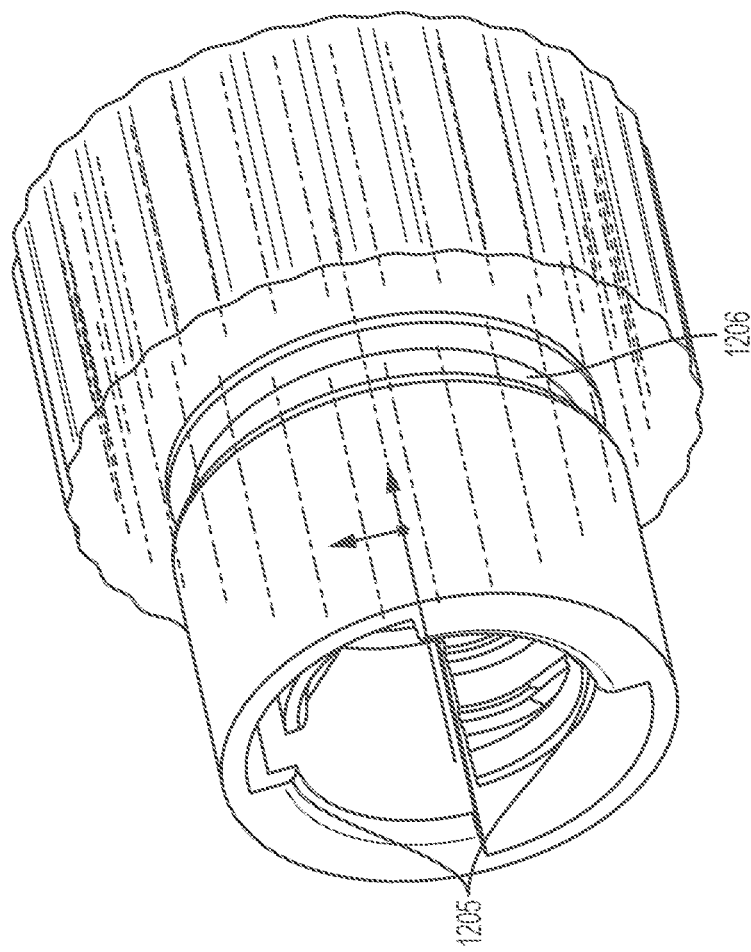
FIGS. 35A-35B are a perspective view of the cleaning cap without a foam/cloth layer.
Figure 35A:
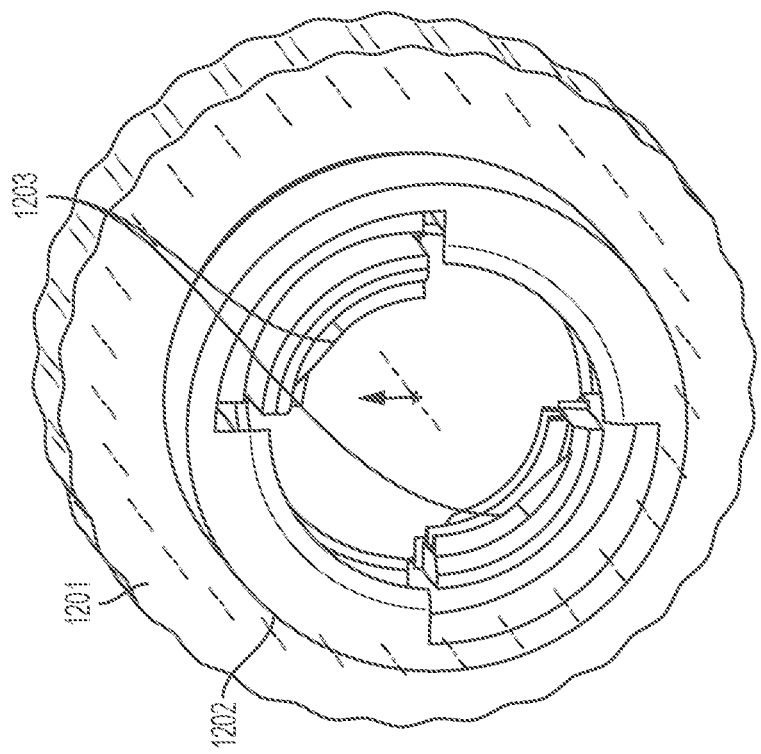

As shown in FIG. 19, when the hub 1003 is inserted in to the opening 1099, an external surface of the hub contacts an edge of the locking arm 1111, causing the locking arm 111 to move in a direction towards the hub 1003. A locking pin 1032 on the locking arm 1111 (see FIG. 17) will then contact the hub 1003 (e.g., on the outer surface of the hub), thus locking the hub to the clamp 1002 and preventing the hub from moving. The locking pin 1032 (or other suitable mechanism) may stop the hub from axial translation. In another embodiment, the device 1001 may include buttons, such as button 1007, that will automatically actuate the locking arm 1111 to move towards the hub 1003 and lock the hub 1003 to the device 1000.

Figure 17:
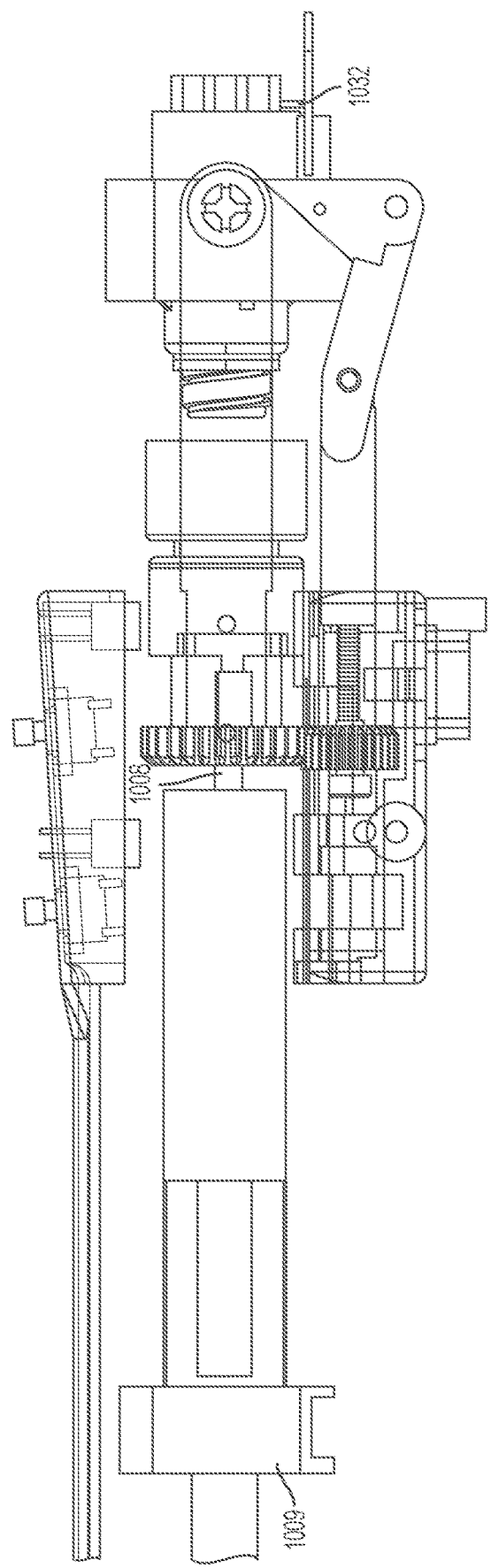
Figure 18:
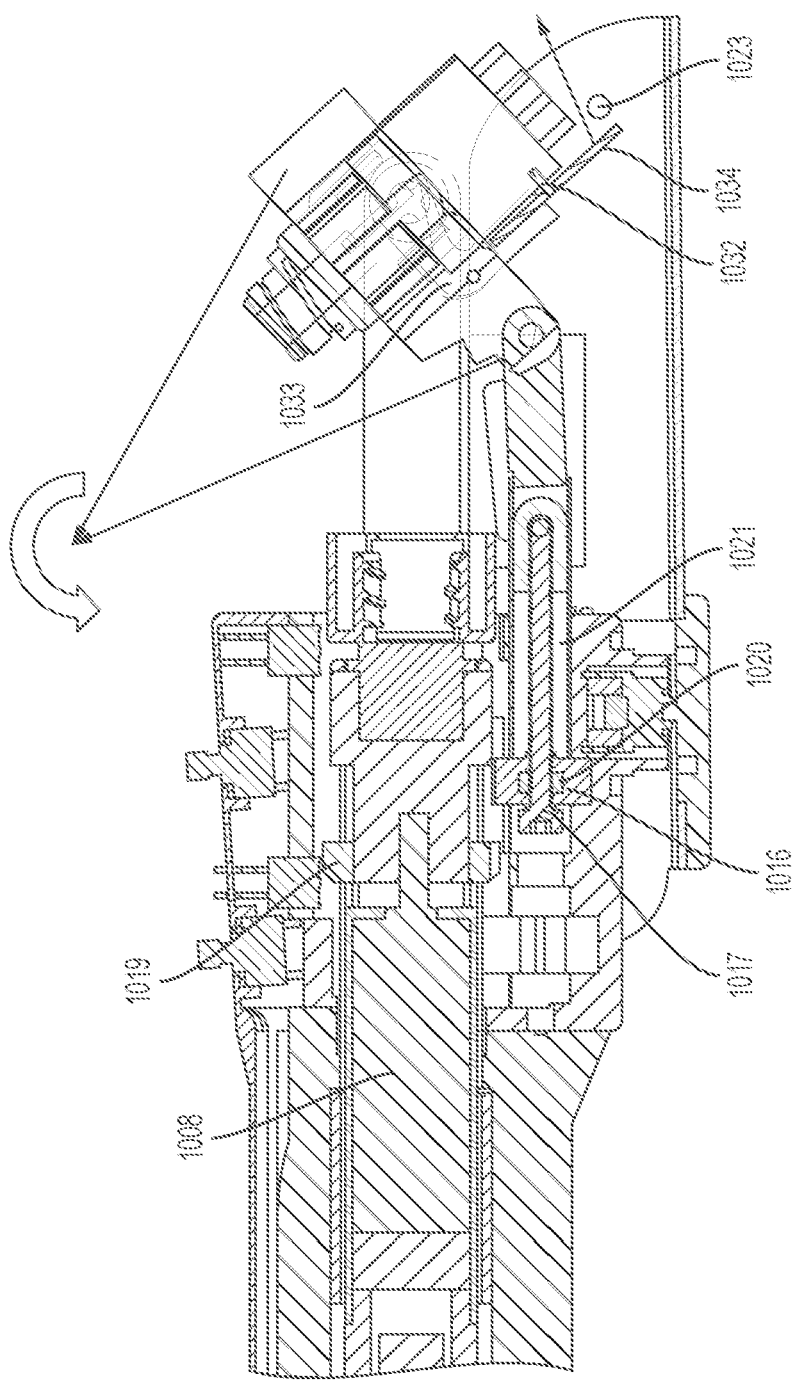

In some embodiments, once the hub 1003 has been cleaned, a clinician may manually eject the hub 1003 from the clamp 1002 by disengaging the locking arm 1111 from the hub 1003 The clinician also may manually eject the hub 1003 after the hub 1003 has first been accessed (e.g., after the hub has been pivoted away from the device to inject a medication into the hub, as will be described). In such embodiments, as illustrated in FIG. 17, the clinician may apply slight force to the locking arm 1111 to move the locking arm 1111 in a direction away from the hub 1003, which disengages the locking pin 1032 from the hub 1003. Once disengaged, the hub 1003 may be removed from the device. As will be appreciated, the clinician may manually eject the hub 1003 both in the pivoted position as shown in FIG. 18, and when the hub 1003 is its original, starting position (e.g., parallel to a longitudinal axis of the device, as shown in FIG. 17).

In another embodiment, the hub 1003 may be automatically ejected from the device 1000 (e.g. via an actuator). In embodiments in which the hub has been accessed for use, the hub 1003 is first pivoted back to its original position. Once in that position, the device may automatically move the locking arm 1111 away from the hub 1003, thus disengaging the locking pin 1032 from the hub 1003. In some embodiments, the locking arm 1111 is disengaged from the hub 1003 via release pins 1023 (see FIG. 27), which contact the locking arm and move the locking arm 1111 in a direction away from the hub 1003. In some embodiments, the automatic ejection process is started by pressing a button 1007 or several buttons 1007 at the same time to move the locking arm 1111 away from the hub 1008.

In another embodiment, movement of the cover 1002 may urge the locking arm 1111 away from the hub, thus disengaging the hub from the device. In such an embodiment, embodiments, the device may include two pins 1023, the pins being positioned so as to carefully avoid the pivoting mechanism. During the pivoting-to-origin process, the pins 1023 are engaged with the wings 1034 on the locking arm 1111 and pushes the hub 1003 out of the clamp 1002 with the force applied by the linear actuation system of the clamp's pivoting mechanism. Extended wings 1034 are released from the pins 1023 after the pivoting-to-origin process is completed. Automatic ejecting also may be performed by an additional mechanism, without an extra actuator and while the hub clamp 1002 is being pivot back to its origin.

In some embodiments, the locking arm 1111 may pivot around an axis. The locking arm 1111 also may be spring pushed. As will be appreciated, the locking/ejecting mechanism may be separate from the hub attachment mechanism. That is the locking/ejecting mechanism may not affect the hub attachment mechanism.

In some embodiments, the clamp 1002 is configured to be disposable after being used for a certain period of time or after completing a certain number of hub cleanings. In some embodiments, the clamp 1002 can be easily removed/installed to the stainless steel extended beams (1025) on both sides of the distal end by snapping the clamp's snap pins into the holes inside the stainless steel beams.

Figure 16:
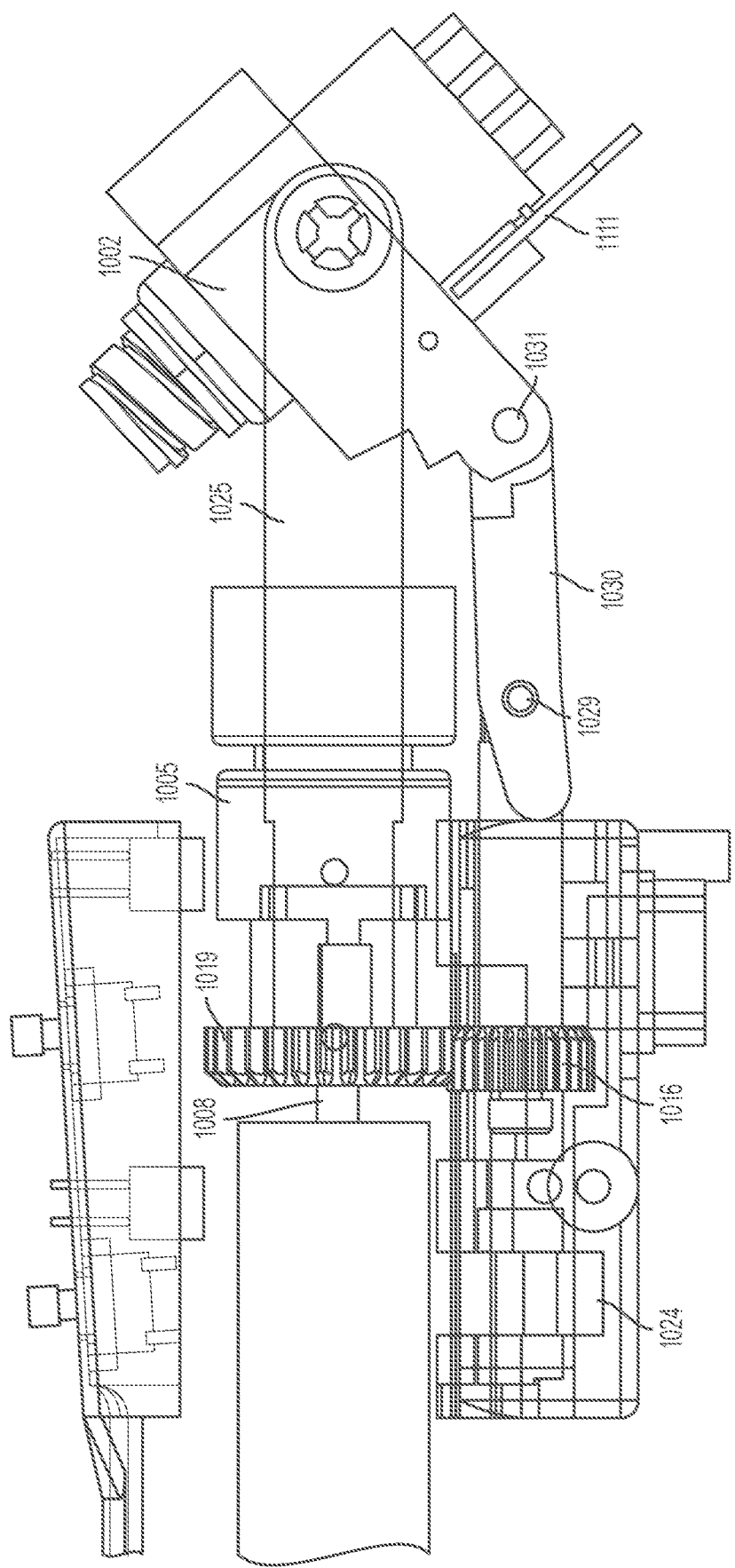
FIGS. 16-25 are side views of a portion of the cleaning device of FIGS. 14 and 15.
Figure 58:
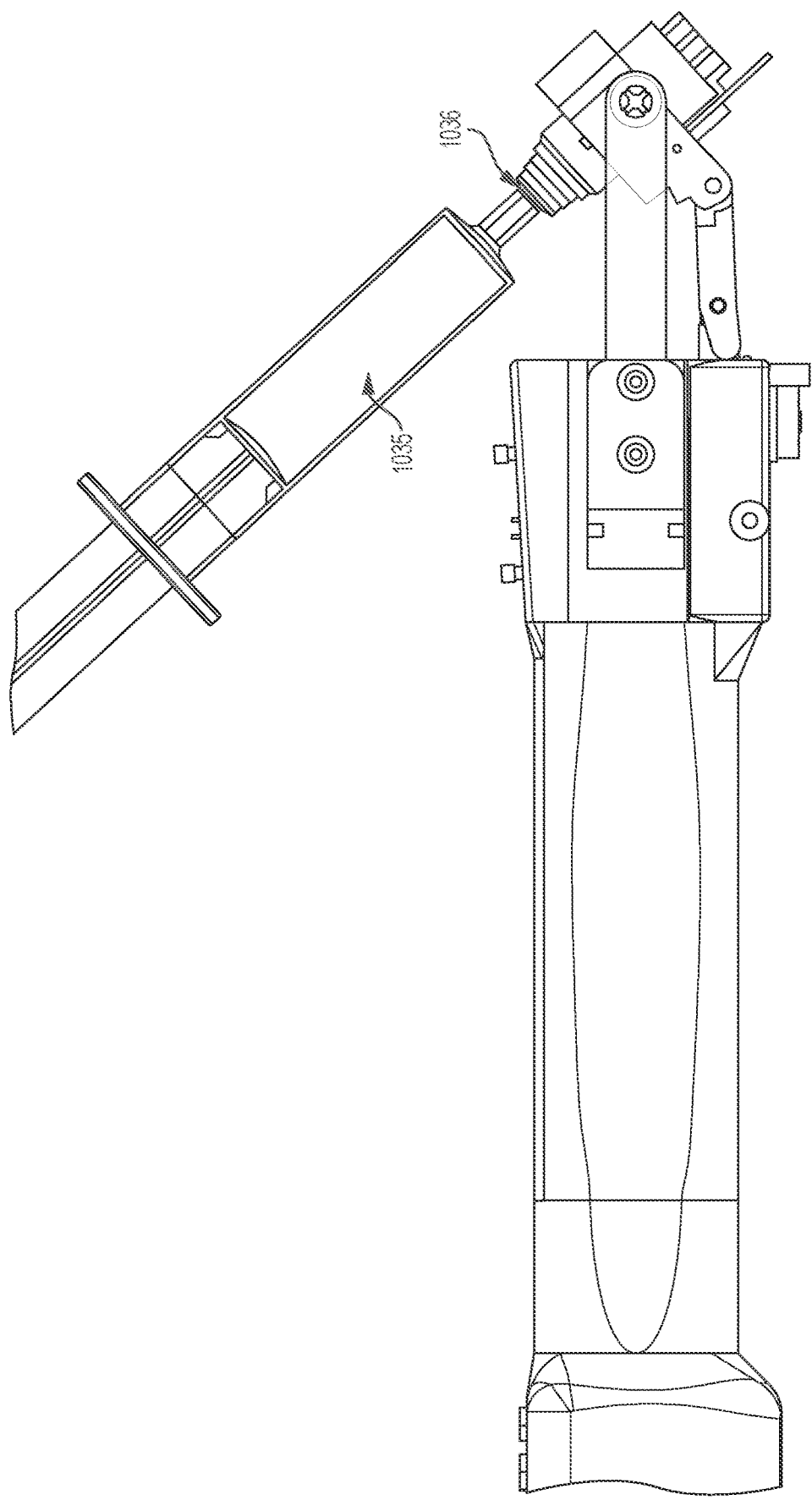
FIG. 58 is a perspective view of a cleaning device according to another embodiment.
Figure 59:
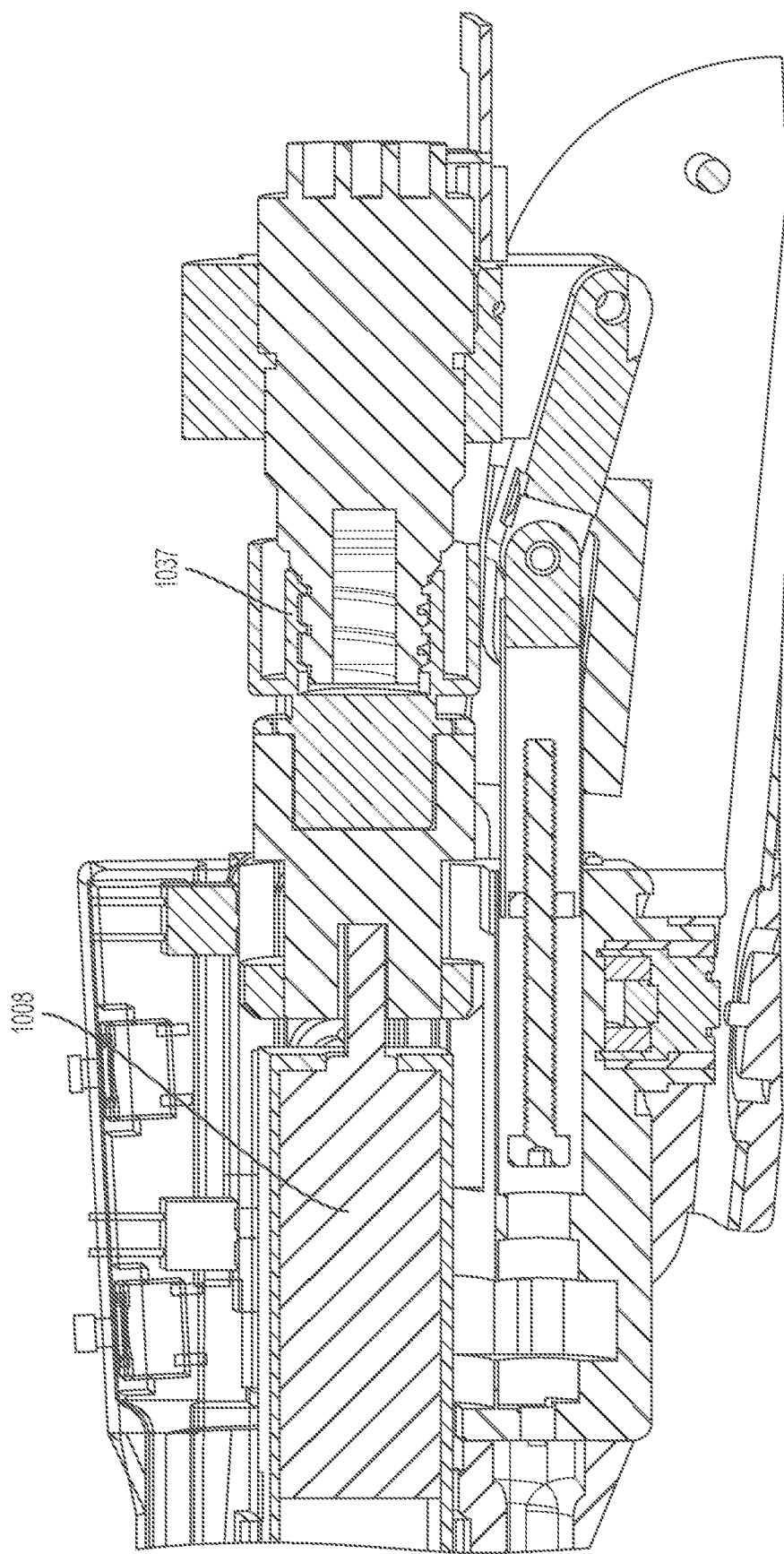
FIGS. 59-60 are side views of a portion of the cleaning device of FIGS. 14 and 15.
Figure 60:
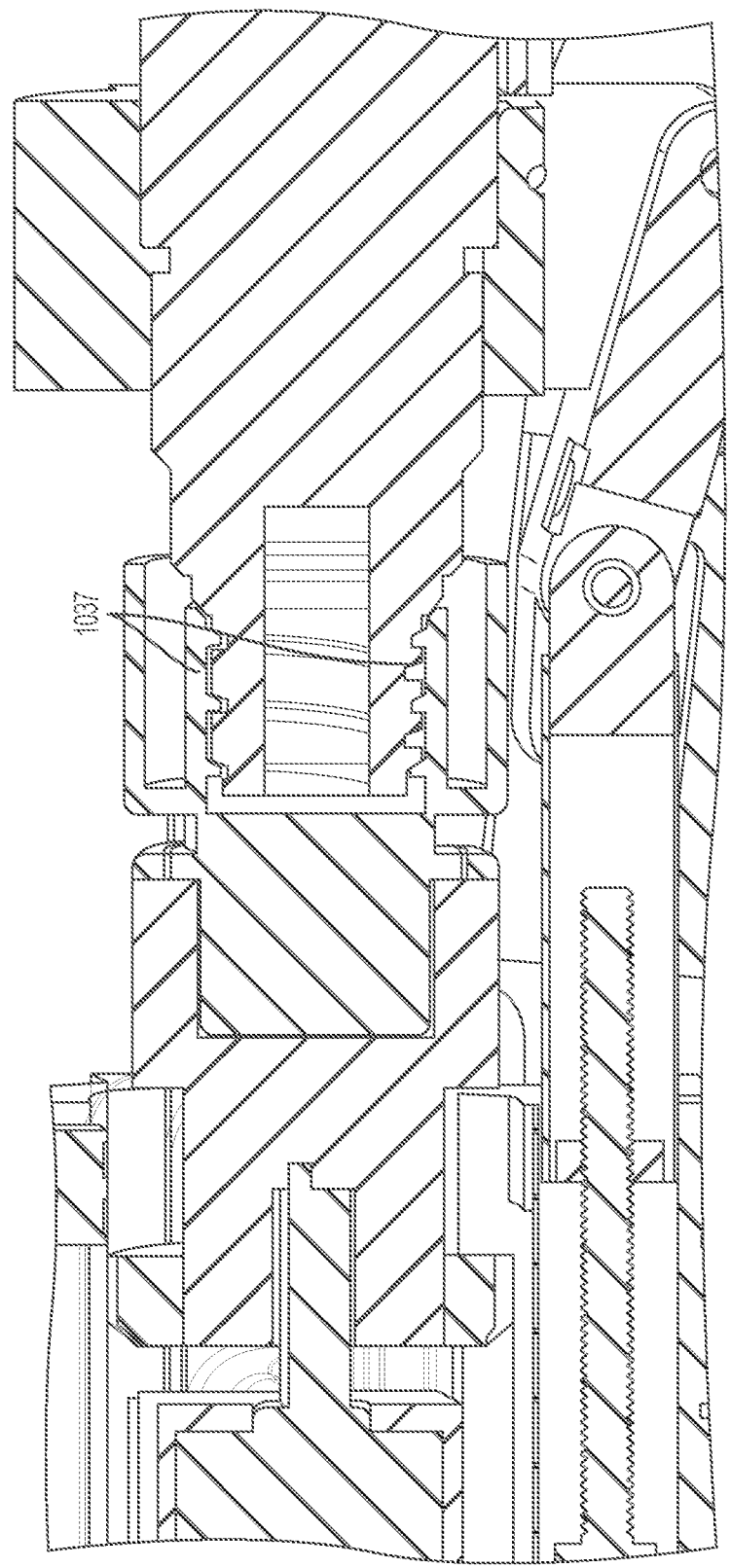

In some embodiments, the device is configured to allow access to the hub 1003 (see, e.g., FIG. 58) without first having to remove the hub from the device (e.g., without first disconnecting the hub from the clamp 1002). In such an embodiment, as shown in FIG. 16, the hub is accessed by pivoting the hub and attached clamp. In other embodiments, the clamp is pivoted after the cleaning process, or after the hub has been accessed, to allow the hub to be disconnected from the device. In such an embodiment, as shown in FIG. 17, the clamp may be pivoted such that the hub is returned to its original position (e.g., parallel to the longitudinal axis of the device). In some embodiments, the clamp can be pivoted manually. Alternately, the clamp may be pivoted automatically (e.g., as actuated after pressing one or more buttons). In these embodiments, the clamp and hub pivot with respect about the pins 1026 (e.g., snap-fit pins) and about the z-axis (see FIG. 13B).

Figure 14:
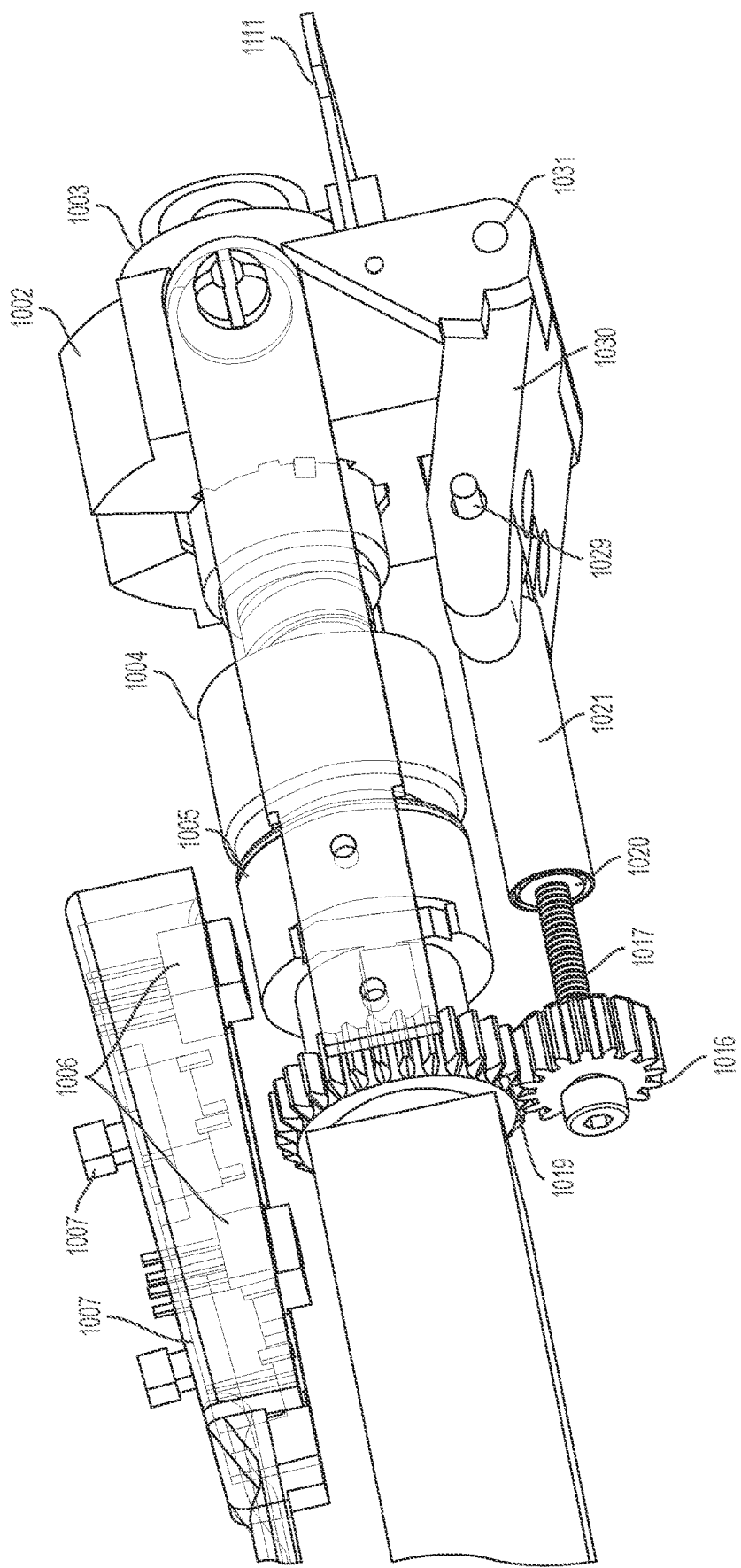
FIGS. 14 and 15 are perspective views of a portion of the cleaning device of one embodiment.
Figure 15:
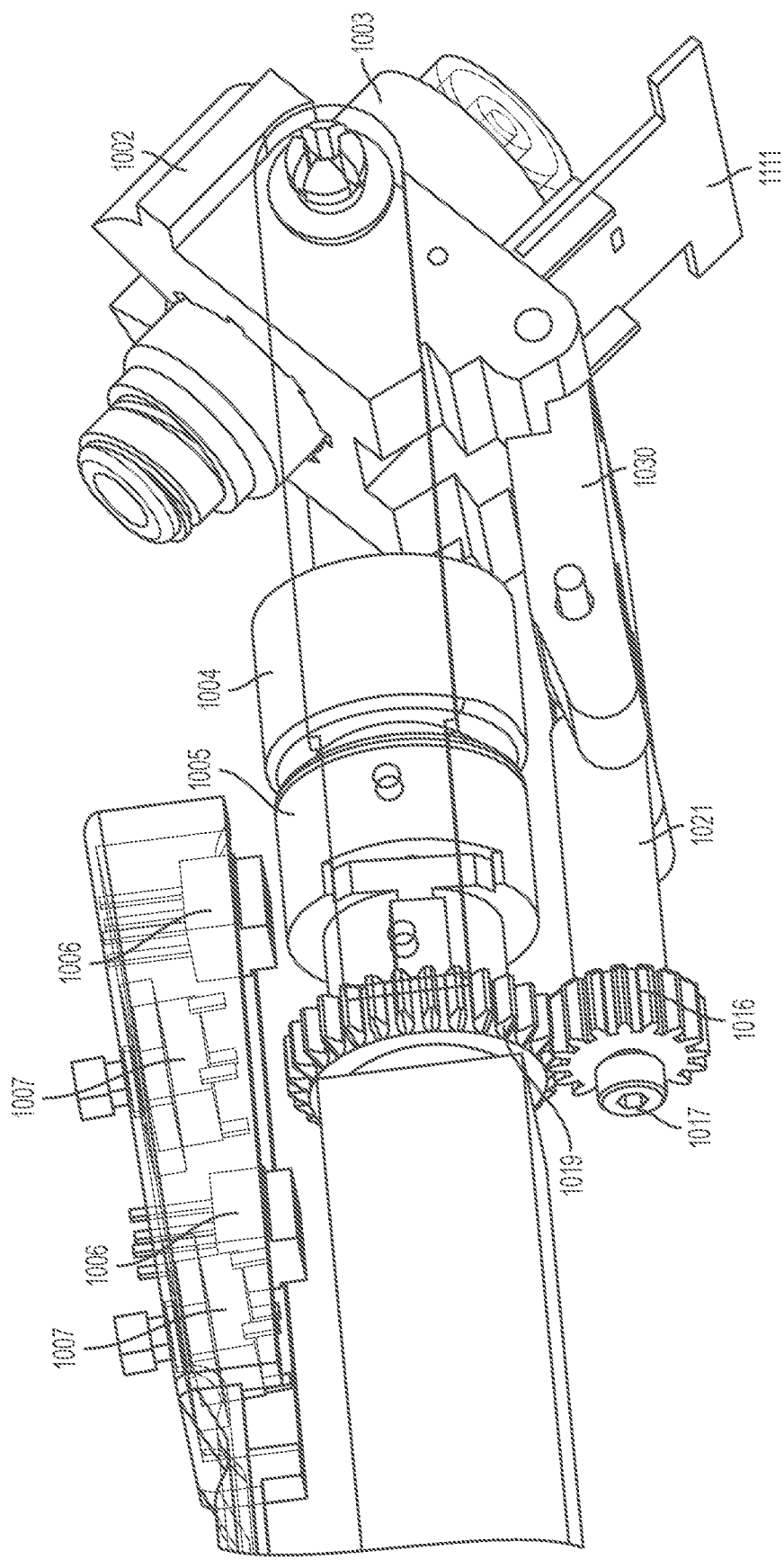

In some embodiments, as illustrated in FIGS. 14 and 15, the pivot mechanism may be connected to and, thus, work in concert the actuation/translation system of the device. For example, as shown in FIG. 14, the clamp 1002 may be connected to the actuation system 1024. That is, on a first end, a screw 1017 and nut 1020 are attached to a rotary actuator 1008 via a set of gears 1016 and 1019, and at a second end the screw 1017 and nut 1020 are attached to the clamp valve hinge pins (1029, 1031). In such an embodiment, the pivoting mechanism (FIG. 6) may be actuated by the same motor 1008 that is used to actuate the cleaning cap (4) (e.g., to rotate and translate the cleaning cap). As will be appreciated, the pivoting mechanism also may be actuated via a separate motor.

In some embodiments, the pivoting actuation is performed while the cap holder and cap are fully retracted into the device and the gear on the linear actuator 1016 is in contact with the cap holder gear 1019, which is actuated by the cap rotary actuation motor 1008. The linear actuation system, includes a linear actuator attached to a lower distal end of the device. In some embodiments, the linear system is mounted to the distal end of the device. In some embodiments, the cap holder gear 1019 disengages the pivoting mechanism's gear while the cap and cap holder are extended out of the device to start the process.

In some embodiments, the clamp is a universal clamp and is designed to fit with commercially available needless hubs. In other embodiments, the clamp 1002 and hub 1003 are uniquely designed to engage with other another. For example, as shown in FIG. in some embodiments, the clamp 1002 includes grooves that are specifically designed to engage with corresponding threads or protrusions on the hub. For example, as shown in FIGS. 13A and 13B, the grooves 1029 may engage with protrusions 1029 on the hub 1003 to lock the hub to the device, thus preventing hub from being twisted during the cleaning protocol.

According to another aspect, the device may be arranged such that the hub may be easily clamped, plugged or snapped into the clamp without the need for locking. In other embodiments, the hub may be designed for being clamped into the clamp (e.g., is clamp friendly). In such embodiments, the cap holder may include a clamp, such as clamp 1501.

Figure 44:
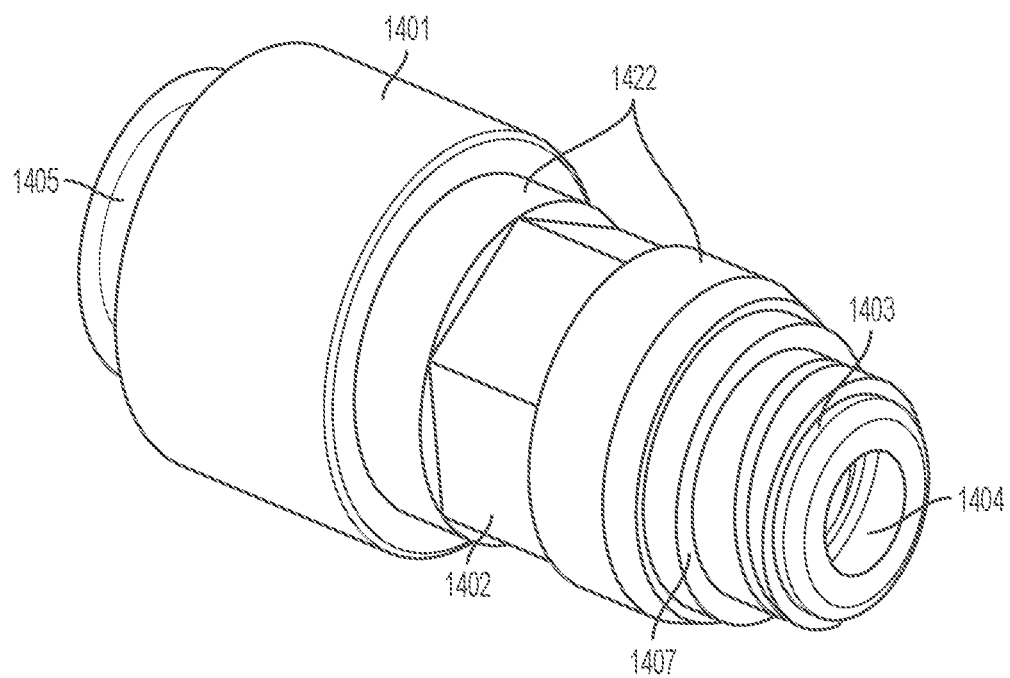
FIG. 44 is a perspective view of the hub according to another embodiment.
Figure 45B:
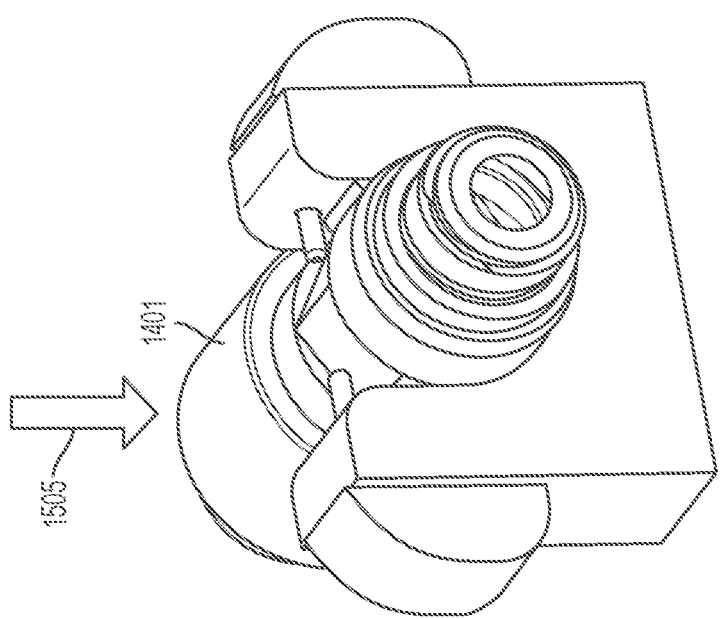
FIG. 45B is a perspective view of the hub of FIG. 44 held in the clamp of FIG. 45A.
Figure 45A:
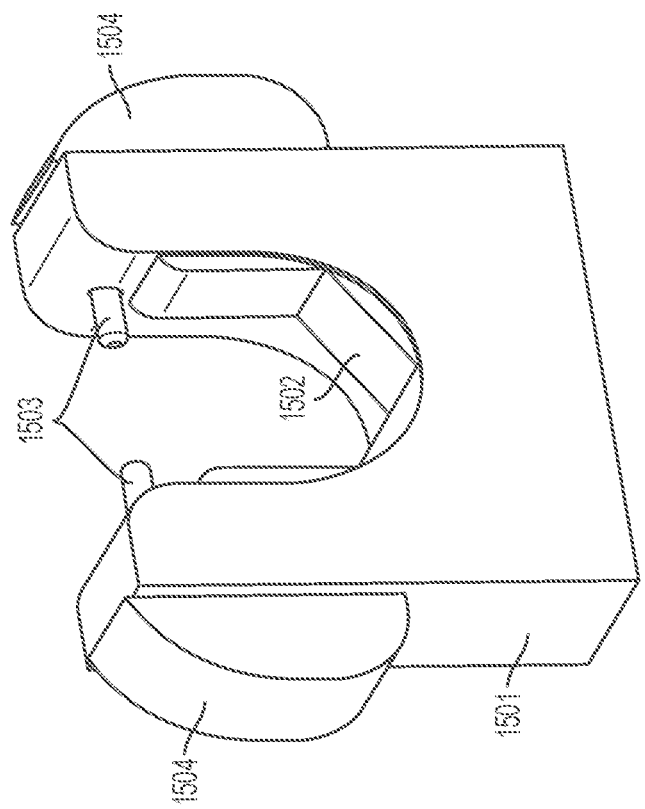
FIG. 45A is a perspective view of a clamp according to another embodiment.

As shown in FIGS. 44, 45A and 45B, for example, in one embodiment, the hub 1401 includes a hexagonal locking geometry 1402, to snap or plug the hub into a clamp 1501 which includes a corresponding hexagonal locking receiver 1502 to prevent the hub from being twisted. As will be appreciated, other suitably-shaped hub locking geometries, and corresponding locking receivers, may be used. As is shown in FIG. 44, the hexagonal locking geometry 1402 of the hub is sandwiched between two hub holding geometries 1422, which, in some embodiments, are cylindrical structures. Accordingly, as the hub is inserted into the clamp (see, e.g., along arrow 1505 of FIG. 45B) the holding geometries 1422 automatically block axial movement and/or translation of the hub (i.e., forward/backward movement of the hub relative to the clamp. The holding geometries 1422 also may allow in-clamp injection without pushing the hub out of the clamp.

As shown in FIGS. 45A-45B, in some embodiment, the clamp 1501 includes one or more pins 1503 that engage with or otherwise overlie the locking geometry 1402 to lock the hub and prevent the hub from ejecting upward. One or more release levers 1504 cooperate with the one or more pins 1503, respectively, such that when the release levers 1504 are pressed, the pins retract to a non-overlying or non-engaging position so that the hub can be lifted out of the clamp (i.e., along a direction opposite insertion arrow 1505). As will be appreciated, the levers 1505 may be pressed after the hub has been cleaned.

Figure 46:
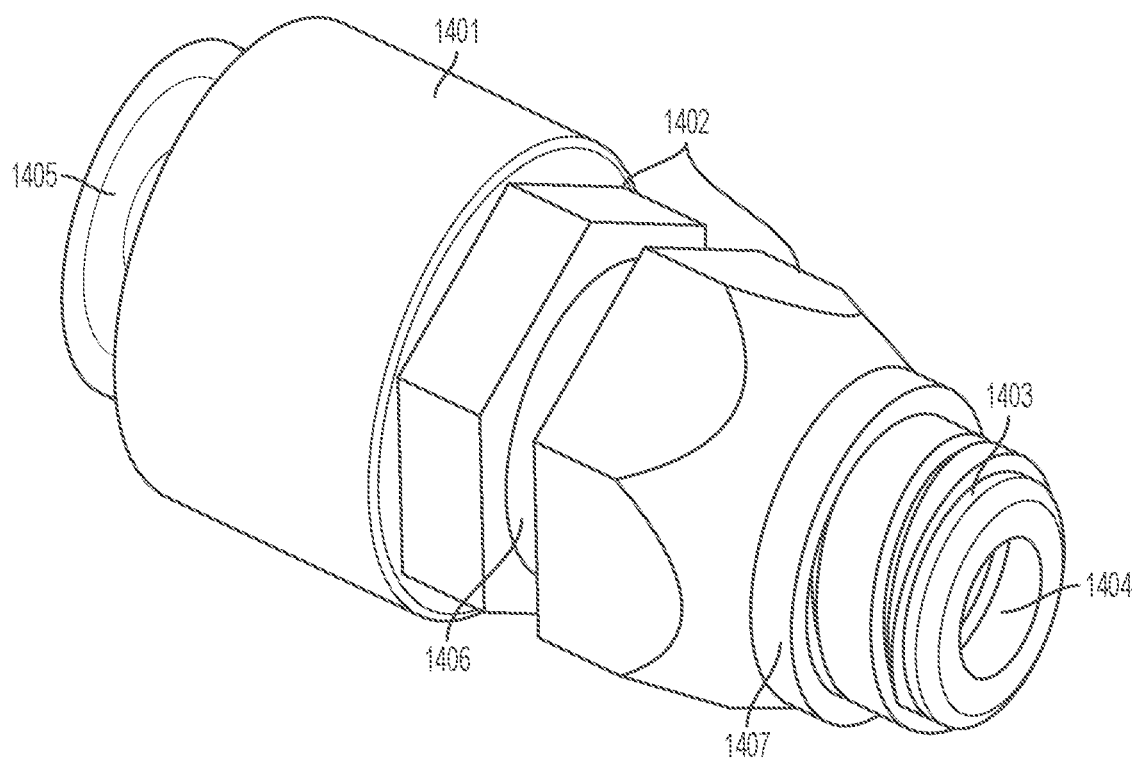
FIG. 46 is a perspective view of the hub according to another embodiment.

As shown in FIG. 46, in another embodiment, the hub may have a hexagonal shaped circumference 1402. As with other embodiments, such a hexagonal shape may be used to lock the hub in a rotational direction. As will be appreciated, other suitable circumferences may be used. The hub also may have a slot or gap 1406 formed in an exterior wall (e.g., in the hexagonal shaped circumference 1402, which may be used to axially lock the hub from axial motion and/or translation, as will be explained below.

Figure 47B:
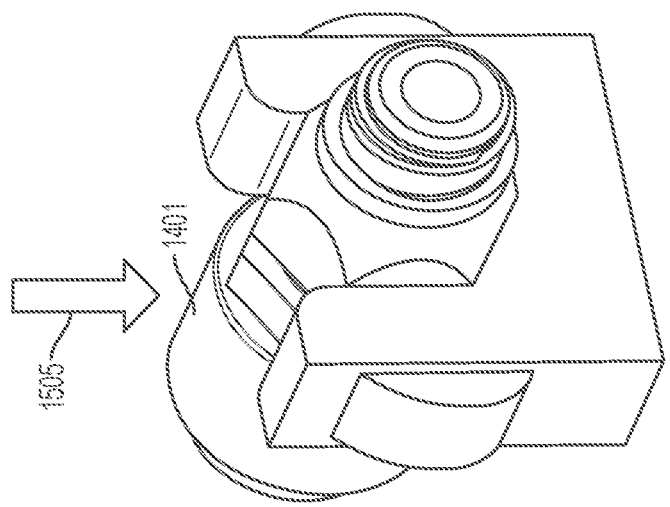
FIG. 47B is a perspective view of the hub of FIG. 46 held in the clamp of FIG. 47A.
Figure 47A:
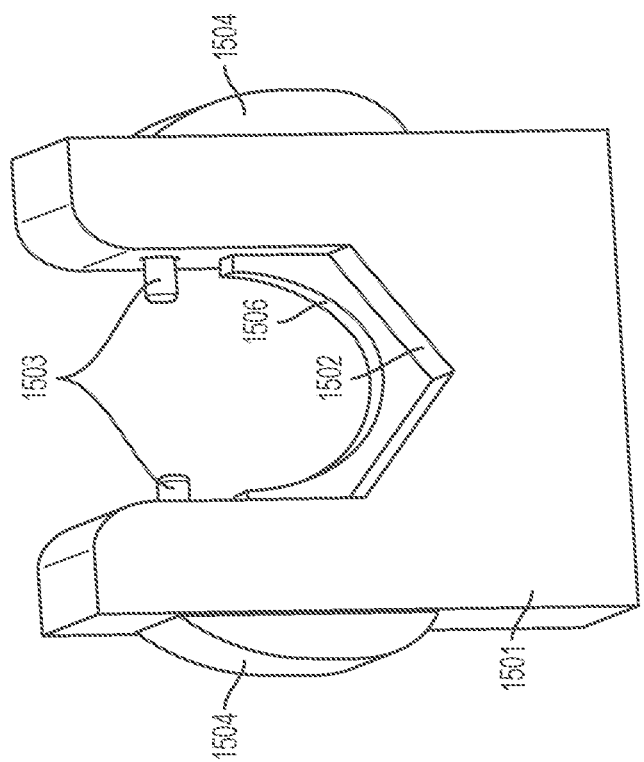
FIG. 47A is a perspective view of a clamp according to another embodiment.

In some embodiments, as shown in FIGS. 47A and 47B, the hub is easily plugged into the clamp by translating the hub 1401 into the clamp 1501 along arrow 1505. This may temporarily lock the hub in both rotational and axial directions without the need for any optional feature to permanently lock the hub such as a locking mechanism. As with the embodiment described above with respect to FIGS. 45A and 45B, one or more pins 1503 that engage with or otherwise overlie the locking geometry 1402 to lock the hub and prevent the hub from ejecting upward. Also, as with the embodiment above, one or more release levers 1504 cooperate with the one or more pins 1503, respectively, such that when the release levers 1504 are pressed, the pins retract to a non-overlying or non-engaging position so that the hub can be lifted out of the clamp (i.e., along a direction opposite insertion arrow 1505). As will be appreciated, the levers 1505 may be pressed after the hub has been cleaned.

Figure 48:
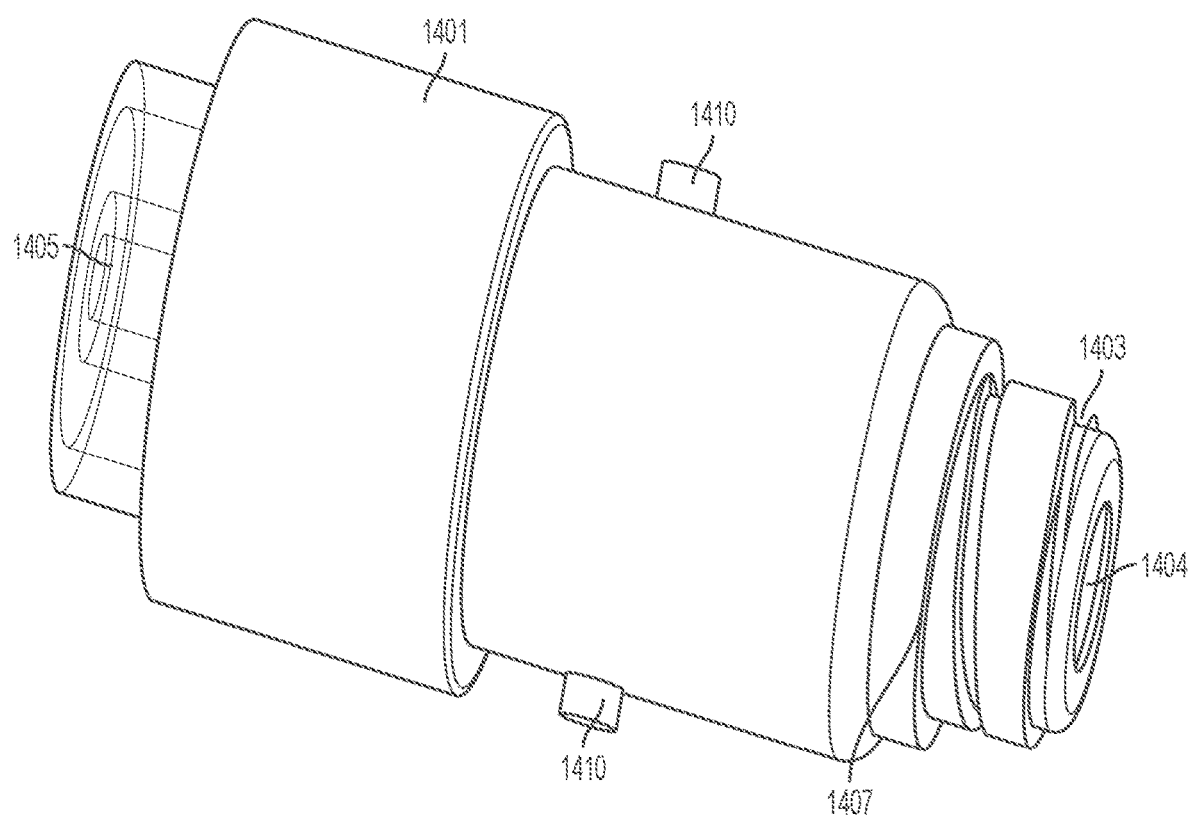
FIG. 48 is a perspective view of the hub according to another embodiment.
Figure 49A:
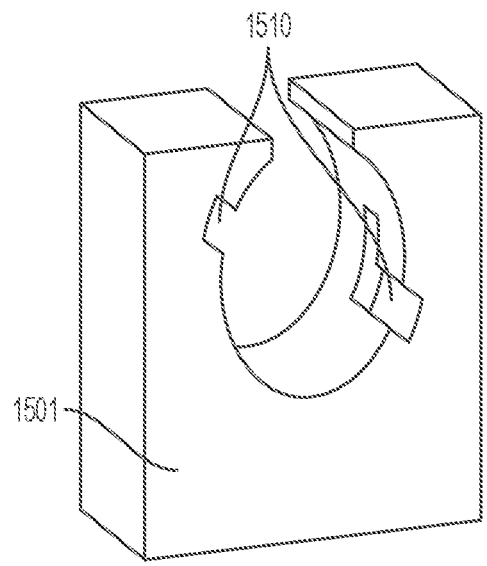
FIG. 49A is a perspective view of a clamp according to another embodiment.
Figure 49B:
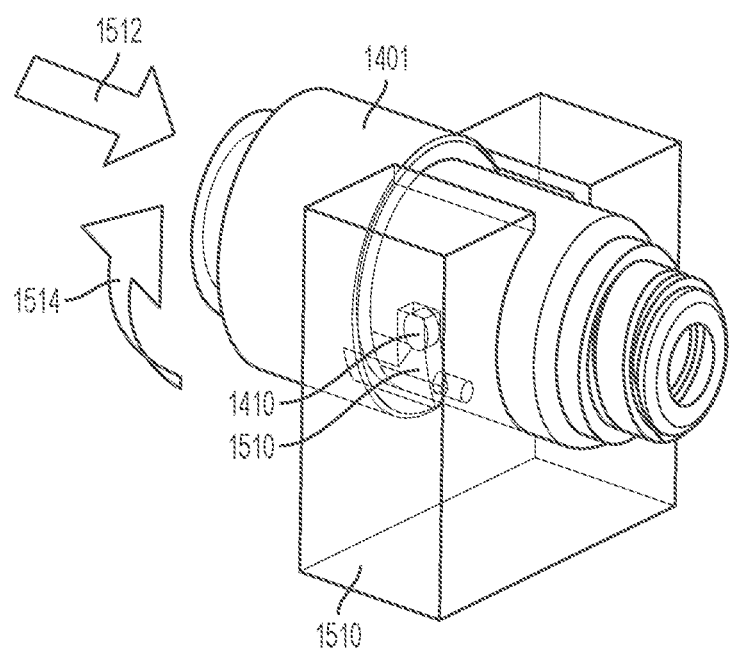
FIG. 49B is a perspective view of the hub of FIG. 48 held in the clamp of FIG. 49A.

In other embodiments, as shown in FIG. 48, the hub 1401 may include one or more pins 1410 on an exterior surface to allow rotational and axial locking. In such embodiments, the clamp (as shown in FIG. 49A) may include a corresponding locking track 1510. The locking track 1510 may be formed in a spiral shape or in another complex curve to allow axial and radial motion to tighten the hub into the clamp. In this respect, as shown in FIG. 49B (which is a rear view of the clamp 1501 (shown in phantom) to FIG. 49A), the hub is inserted along arrow 1512 into the clamp 1501 (where pins 1410 slide in a first portion of the tracks 1510) and rotated along arrow 1514 such that the pins radially move within the second portion of the track 1510. In this way, the hub is substantially held in the clamp. In some embodiments, the hub may be simply axially inserted into the clamp, with a locking mechanism that locks the hub automatically. In other embodiments, the hub is twisted to lock the hub in the clamp. As will be appreciated, in such embodiments, the locking mechanism may be optional.

In some embodiments as shown in FIGS. 44, 46 and 48, the hubs may be needleless (where end 1404 lacks a needle) and instead is formed as a luer lock 1403 mechanism. The hub surface may be chemically or plasma treated. A needleless push action valve in end 1404 also may be treated. An anti-microbial coating may be applied to avoid bacteria formation as well as blood clot formation.

In some embodiments, the hub also may be coated with Slipper Liquid-Infused Porous Surface ("SLIPS"). As will be appreciated SLIPS may transform the surfaces of any solid material into a microscopically thin and ultra-smooth immobilized "sea" of lubricant. This treatment may help to reduce the amount of blood and microbial agents on the hub surface (e.g., threads that are caked with dried blood and contaminated with microbial agents that can lead to infection and prolonged hospitalizations) and may enhance sterilization by the device. SLIPS also may be easily coated onto any central line hub catheter using standard techniques and processes.

In some embodiments, the device also has a motor 1008 that rotates the cap in a clockwise or counterclockwise direction and/or in a vibrational manner. The device also may include a translational actuator that translates the motor 1008, cap holder 1004 and cap 1005 towards the hub 1008 until the device engages with the hub (e.g., via the cap holder and attachment mechanism). Once has device has finished cleaning the hub, the translational actuator may retract the cap, cap holder and motor.

In some embodiments, a single motor may perform different options, which includes: rotating the disinfecting cap for scrubbing, axial vibratory translation of the cap, pivoting mechanism is actuated with the same motor, and the airflow for drying enhancement is created with the same motor.

Figure 12:
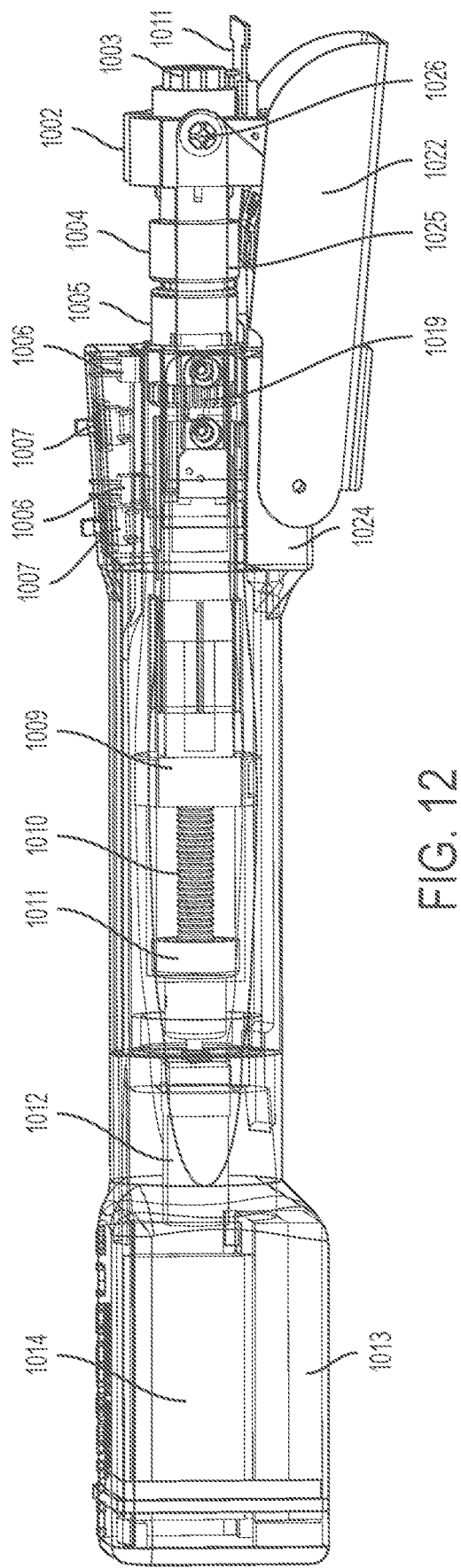

As previously described, the cap may be rotated and/or translated during the cleaning process. In one embodiment, as shown in FIG. 12, along a translational axis of the device 1001 there is a translational actuation system that manually translates the cleaning mechanism. In some embodiments, the translational actuation system is a linear actuation system. The linear actuation system may be motorized and may include a screw 1010 and nut 1015 attached to a geared motor 1012 that transforms rotation to translation. The nut may be attached to a solid body or may be integrated in the solid body which holds the motor (8) in a cabin that is configured to only move axially inside the solid body of the device 1001. The translational actuation system may vibrate or perform translational back and forth motion or apply axial force while the cap 1004 is engaged with the hub 10083 for thorough and effective cleaning. In some embodiments, the translational actuation system may disengage the pivoting actuation system from the cap actuation motor 1008. The translational actuation system may include a rack & pinion mechanism. The translational actuation system also may include a position sensor.

In some embodiments, the translational actuation system is configured to be limited or stopped mechanical or via limit switches. The translational a actuation system also may be used for ejecting the hub. Additionally, the translational actuation system may be used for pivoting actuation.

In some embodiments, the translational speed can be controlled and adjusted. In some embodiments, the translational actuation system and rotational actuation may work simultaneously to move the cap holder and/or cap during the cleaning process.

In some embodiments, control of the device may be performed via a programmable control board (14). The cleaning parameters may be adjustable based on different applications.

In some embodiments, during and after the cleaning process, a color varying LED may indicate the status. In some embodiments, a buzzer or speaker may create sound to indicate the start of the process, the end of the process or may send important messages such as battery low or cleaning failure.

In some embodiment, one or more batteries may be integrated into the device for cordless application. The device could be charged through wireless induction as well as electrical contact. The charging station is designed to allow charging of the device while it is not being used, as well as in some embodiments, loading the new disposable caps or disposing the used caps. In one embodiment, the device (1) may include a rail or fitting structure (222) to allow easy attachment to the charging station and precise positioning on the station. The fitting structure may be locked into the charging station as soon as the handheld device is returned to the station and sensed.

In some embodiments, the device includes one or more sensors. In some embodiments, the device has a number of sensors to control the cleaning and other processes, such as, for example, sensors to feedback the rotational speed, count the number of rotations, limit switches, position sensor, etc. In some embodiments, a limit switch may be employed to indicate the pivoting limit. A limit switch may be used to indicate the pivoting-to-origin limit. In other embodiments, a limit switch is employed to indicate the cap/cap holder/translational axis extension limit. A limit switch also may be used to indicate the retraction of cap/cap holder/translational axis. As will be appreciated, the limit switch can be optical, mechanical, inductive, or capacitive. Other suitable limited switches also may be used. In some embodiments, the translational position is measured via a distance and/or position sensor. The rotational speed of the cap actuation system may be measured by an encoder, optical sensor, induction sensor, mechanical sensor, or another suitable sensor. In other embodiments, two or more optical sensors are used in the device to allow counting the number of turns, measuring the speed, or positioning the cap holder prior to the automatic loading.

In some embodiments, the cap engages with the cap holder 1005, which locks the cap 1004 in rotational directions and free axial translation. In one embodiment, the cap may include a cavity, such as a hexagonal shaped cavity, to lock the cap to the cap holder.

The cap holder may have a holding mechanism with an opening to allow side load as well as axial loading. The cap holding mechanism may lock the disposable cap on rotational directions. The cap holding mechanism also may include complaint mechanism/s to hold the cap safely in place. In one embodiment, the cap holding mechanism is designed to allow easy manual loading of the disposable caps. The cap holding mechanism may allow automatic loading of caps. The cap holding mechanism also may include a reference structures, a body, and/or components that trigger sensors, such as a rotational speed, counting or positioning sensor.

The cap-holding mechanism may include a locking mechanism to automatically lock the cap. The cap holding mechanism may include a compliant mechanism or a spring loaded or pushed mechanism to enhance the process. As will be appreciated, the cap holding mechanism may vary based on the cap design and can be disposed or replaced in the certain time period.

FIGS. 33-39 illustrate various embodiments of a manual cap. As illustrated in these figures, the plastic or polymer version includes a sealed scrubbing chamber 1202 which is attached to a handling/holding surface 1201. Two threaded compliant member 1203 are located inside the sealed chamber. A single/multi pieces of foams 1204 are inserted into the sealed chamber and are soaked in disinfection solution. In one embodiment, the threaded compliant members 1203 are covered with a thin layer of cloth/foam into which a disinfection solution is impregnated. As shown in FIG. 35B, the cap may include is a track 1206 to allow the cap to be sorted or guided in a cartridge package.

Figure 36:
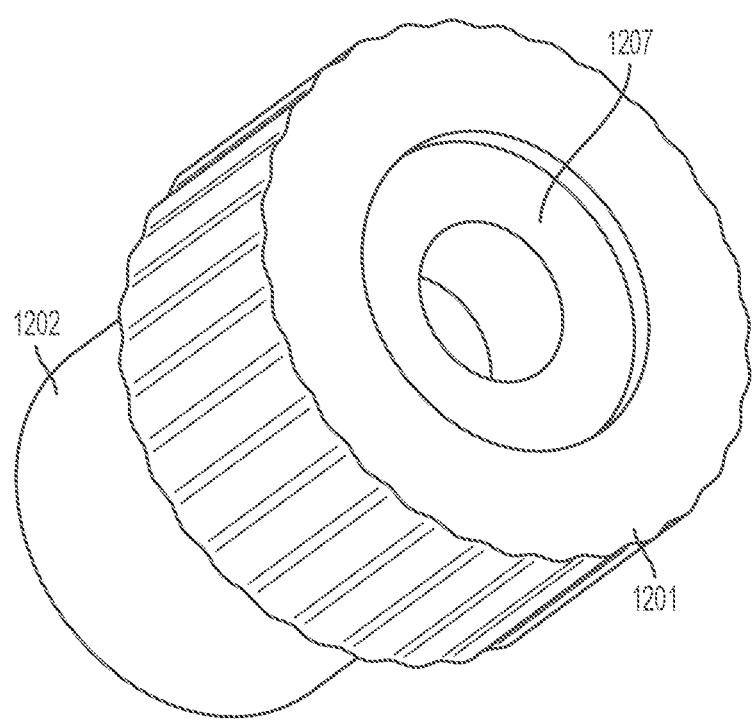
FIG. 36 is a rear perspective view of the cleaning cap of FIG. 33.

As shown in FIG. 36, in one embodiment, the end of the cap adjacent to the holding surface 1201 includes an extra sealed cavity with a foam 1207. This sealed cavity 1207 may be impregnated with a disinfection solution or an anti-microbial, non-stick coating such as SLIP for after access blood splash cleaning and/or have an anti-microbial, non-stick coating to reduce the surface energy and kill the infectious factors as well as reduce the risk of blood clot formation for easy cleaning for the next access. The same feature might be used as a standalone coating cap for infection reduction, anti-microbial, clot resistant hub coating purposes.

Figure 37:
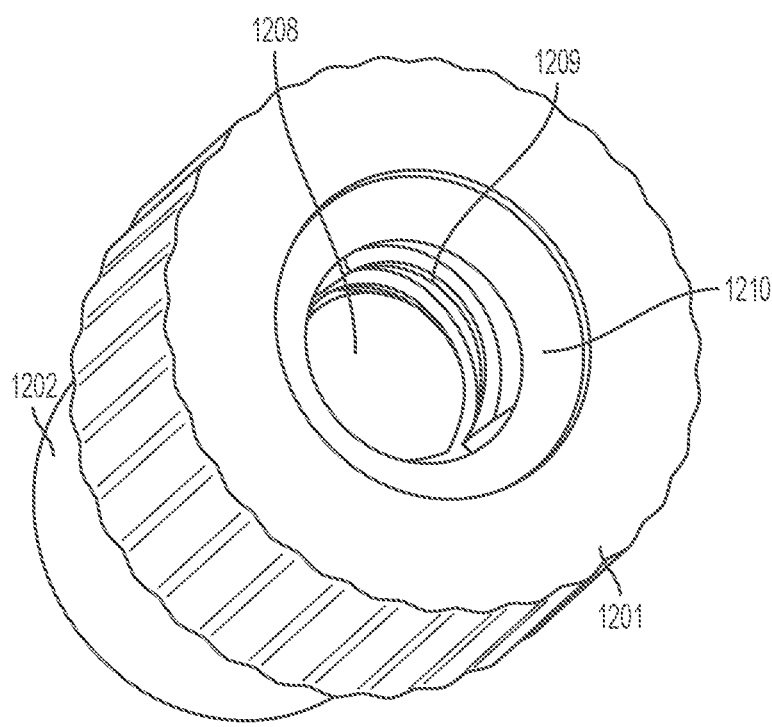
FIG. 37 is a rear perspective view of the cleaning cap according to another embodiment.

In another embodiment, as shown in FIG. 37, the other side of the cap might be used as a permanent covering/disinfecting cap for after access use. As shown in FIG. 37, there is an extra sealed cavity which is Luer threaded 1209 to be tightened on the hub thread and may include a sealing ring 1210, which protects the cap from getting dried in long time. Both side cavities are sealed in packaging process using removable sealing film.

In still another embodiment, a rubbery or elastic sealant (similar to the sealing ring 1210) may be employed at the distal end of the sealed scrubbing cavity 1202 (see FIG. 36) to seal the cap cavity while fully locked at the hub prior to the threshold of snapping action and use the same cavity for permanent sealing.

In some embodiments, the cap is a manual cap that may include all the features available in the motor actuated disposable caps or the exact same cap being used for manual application. The specially designed manual cap is designed based on a snapping threaded features, which allows locking into the Hub threads and then jumping or snapping over the threads when the cap is twisted, thus, thoroughly cleaning the hub tip as well as the grooves with high friction. Using the threaded design, the cap is hooked to the device such that the cap will not fall off while being twisted in clock-wise (or thread locking) direction, which may make it easier to reposition the hands or rest fingers while scrubbing/twisting is being performed.

After finishing the cleaning process, the cap may be left on the hub to cover the hub and maintain a sterile environment. For example, the cap may be left on the bed or bedside without the risk of recontamination while the medication is being prepared, in emergency situations, or prior to access the hub.

In some embodiments, the threaded compliant member 1203 may be covered with a thin layer of foam/cloth which may be impregnated with alcohol. Such embodiments may allow certain/high axial force due to the pressure applied by the thread tightening. This also may standardize the amount of friction performed by care providers.

In some embodiments, a snapping mechanism reduces the pressure periodically to allow the tip cleaning foam to absorb the infectious objects from the surface of the hub's tip. In some embodiments, the snapping mechanism creates periodical axial motion.

In some embodiments, when the cap is rotated with respect to the hub and the threads of the cap jump or snap over the threads of the hub, the cap creates an audible or tactile alert. That is, the cap may make a snapping sound or the clinic may feel the cap jumping from over the thread. In such embodiments, the care provider may simply count the number of turns that he felt or heard snapping over the thread (e.g., the sound or vibration precisely) without needing to checking the time, as is currently done. In some embodiments, the care provider may count 5 turns, 10 turns, 15 turns, or another suitable number of turns sufficient to clean the hub. In some embodiments, counting the number of turns encourages consistency in the hub cleaning process. That is, in such embodiments, it may be easier to count the number of turns than to watch a period of time elapse on a clock.

Figure 38:
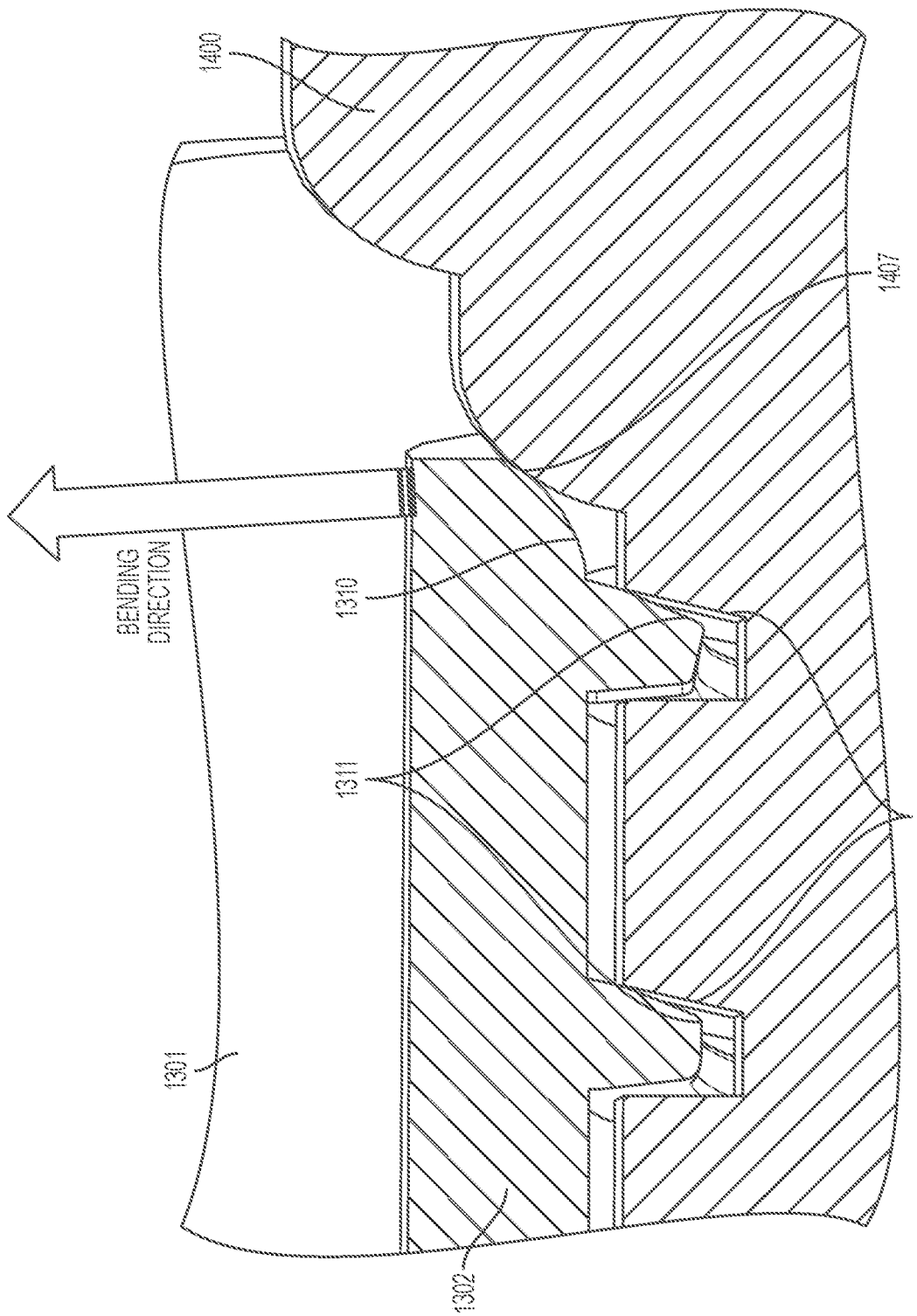
FIG. 38 is a cross-section view of the hub and cap engagement according to one embodiment.
Figure 39:
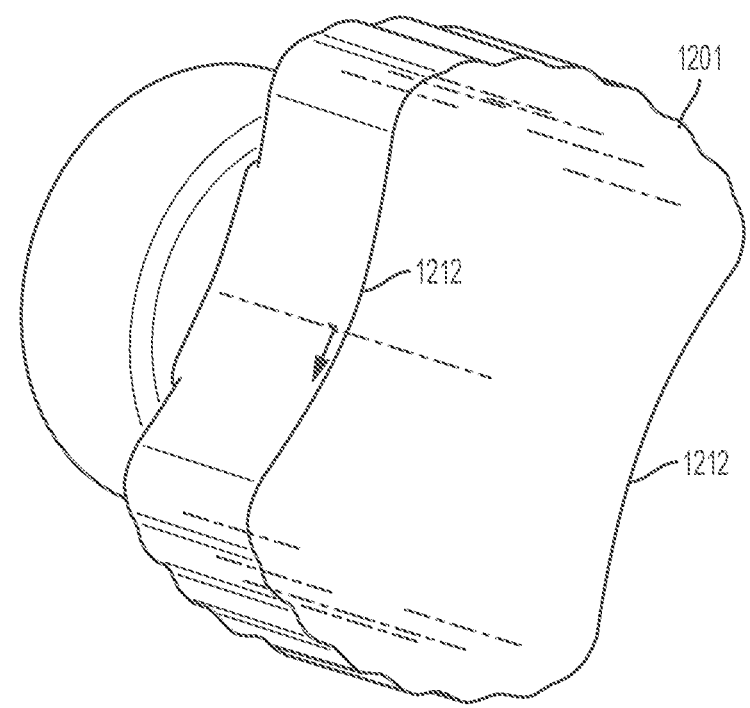
FIG. 39 is a geometric feature of a holding element.
Figure 40A:
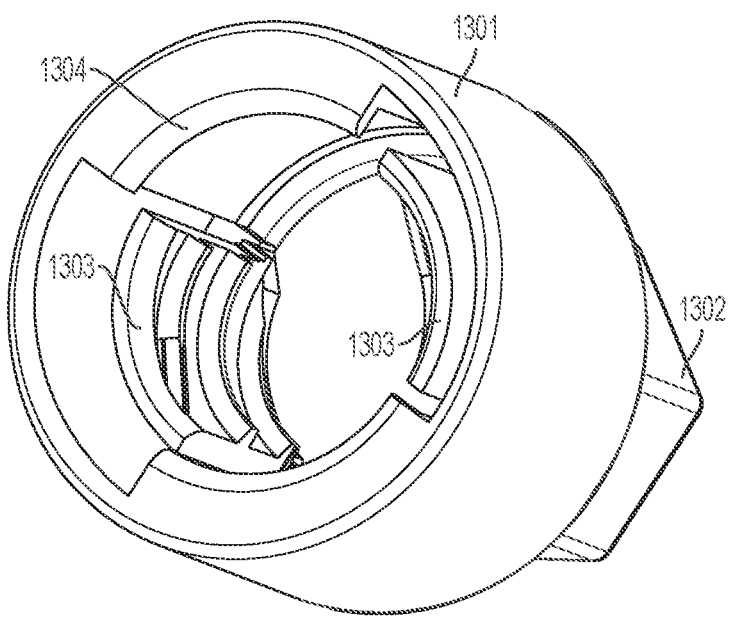
FIGS. 40A-40C are views of the cap according to another embodiment.
Figure 40C:
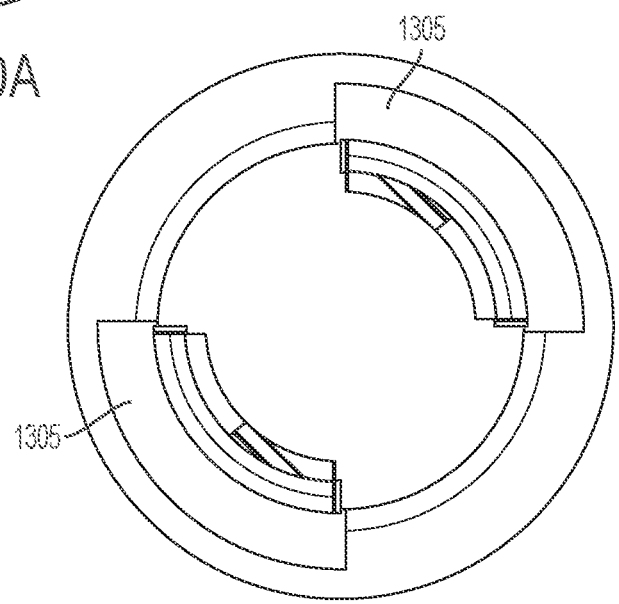
Figure 40B:
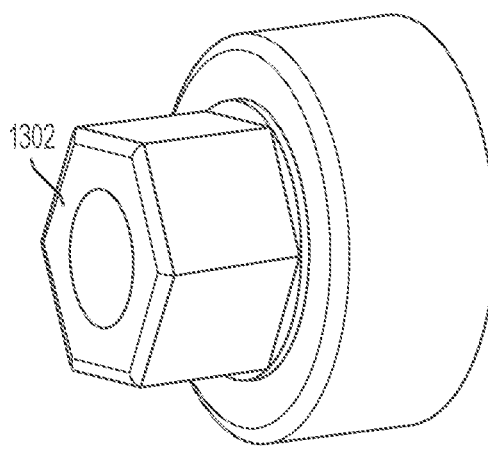
Figure 41:
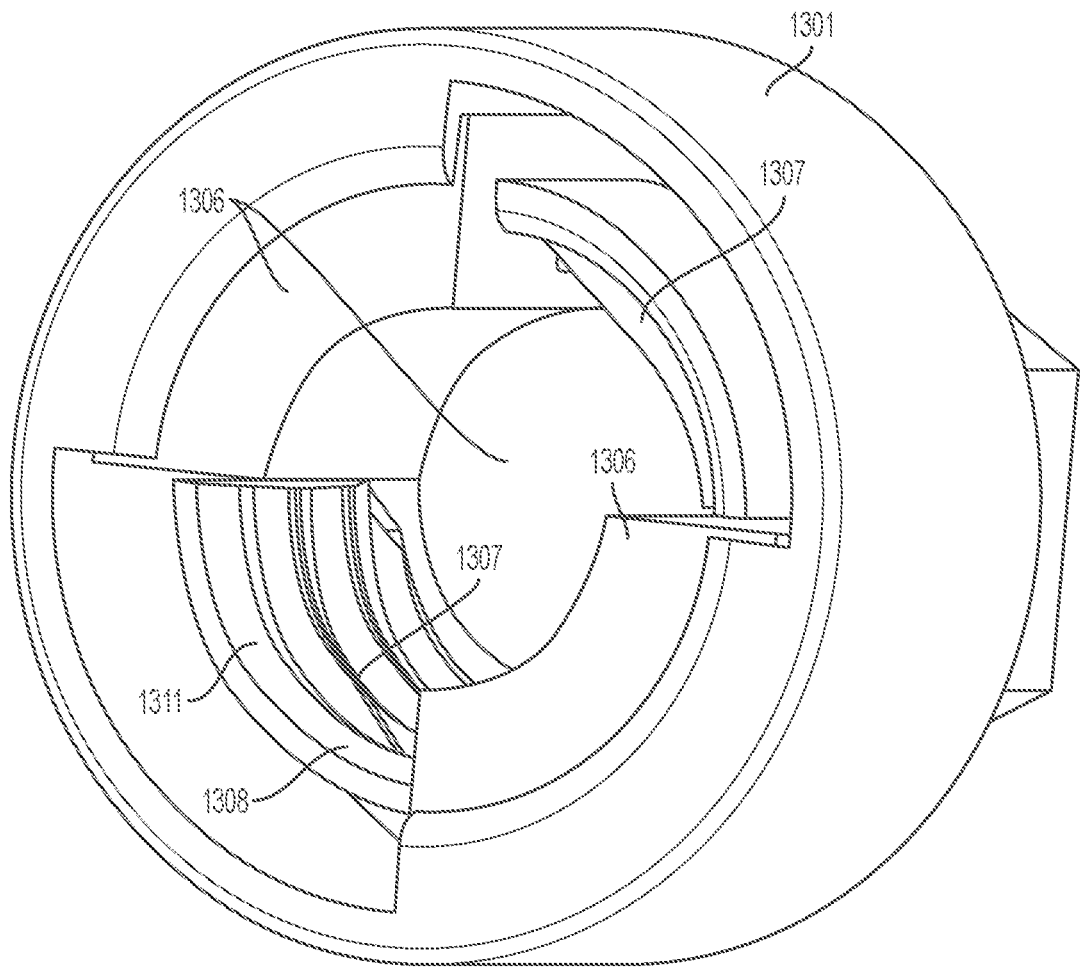
FIG. 41 is a perspective view of the cap of FIG. 40A including the foam.

In some embodiments, the threaded compliant member allows the mechanical snapping action to avoid locking and is enhanced for low torque actuation (see FIG. 38). This is performed by the curved, beveled, or angled thread edge 1311 as well as angled/curved periphery of the compliant threaded member 1310, which can push against the hub's end of thread geometry 1407 and push the compliant member aside. This may allow the threads to release and snap over the hub's luer thread and the cap to automatically move back to match the threads with the hub again. This happens every in each rotation of the cap around the hub.

In some embodiments, the cap includes a safe chemical compound or an indicator, such as a color indicator, is included to indicate the wetness or dryness of the cap prior to the use. For example, the indicator may alert a user when the cleaning solution in the cleaning cap has dried up and, thus, the cleaning cap is not suitable for use.

In some embodiments, the manual cap may include an opening on the side to allow fast drying.

In some embodiments, a SLIP coating may be applied for anti-microbial coating, to reduce the surface energy and to avoid clot formation to make the next cleaning process easier and reduce the amount of bacteria on the hub surface.

In some embodiments, the handling/holding element 1201 may include some geometrical features 1212 to enhance actuation and reduce the slipping.

Figure 10:
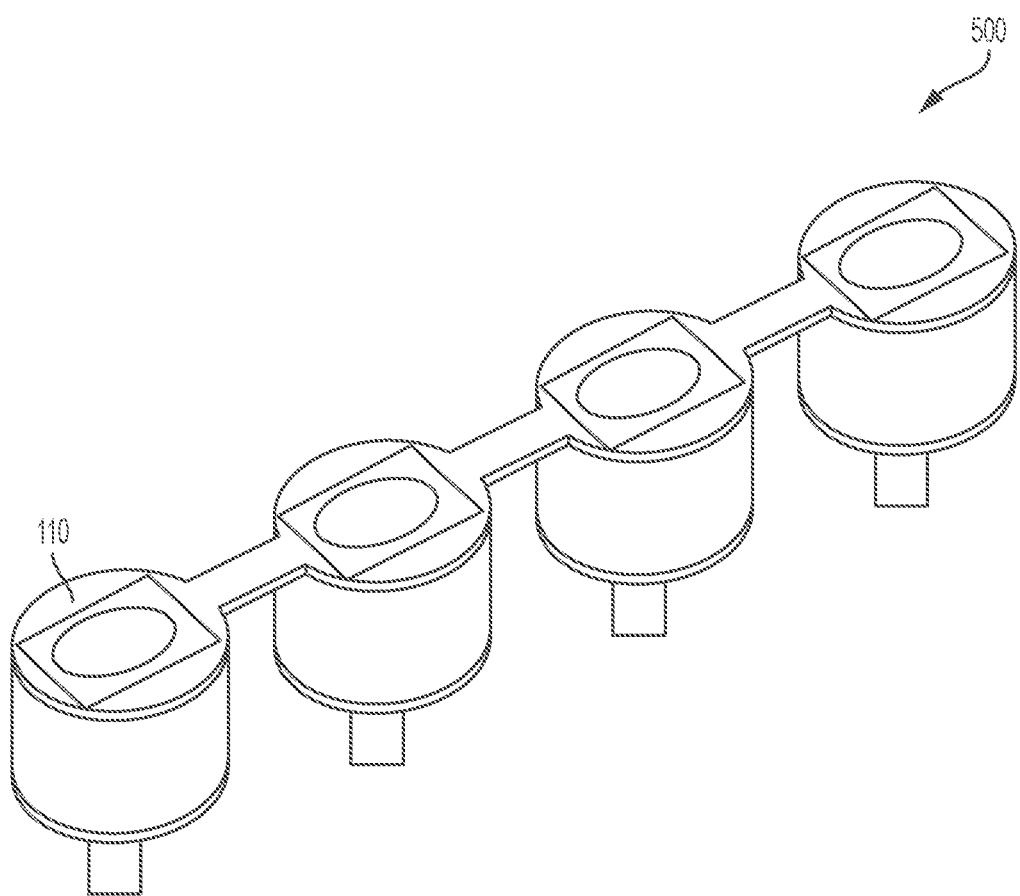
FIG. 10 is a perspective view of a multi-pack cartridge of cleaning caps according to one embodiment.
Figure 53:
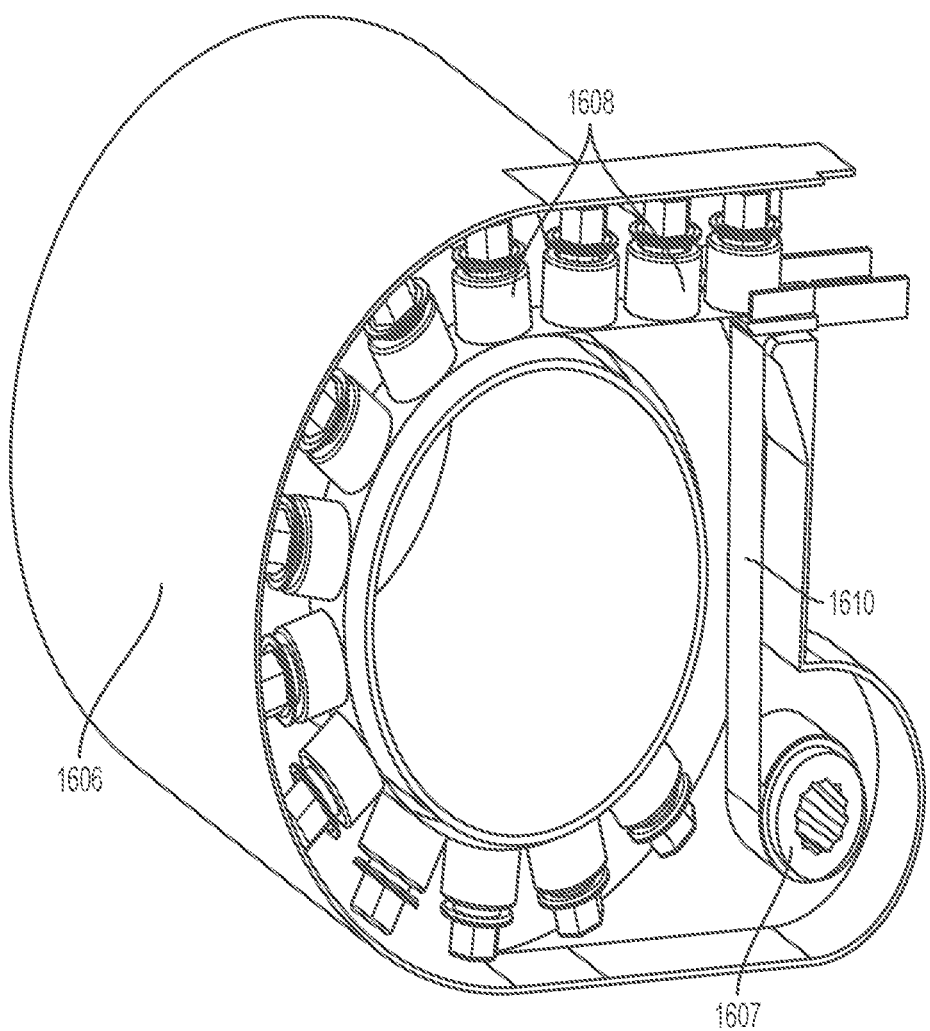
FIG. 53 is a perspective view of a portion of the charging station of FIG. 51.
Figure 54A:
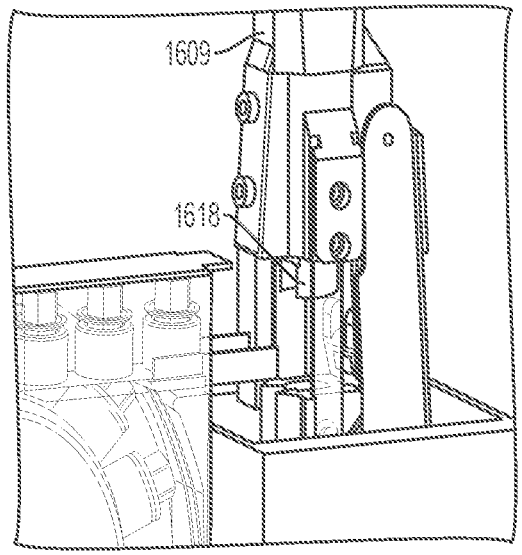
FIGS. 54A-54D are perspective views of portions of the charging station with an attached cleaning device.
Figure 54B:
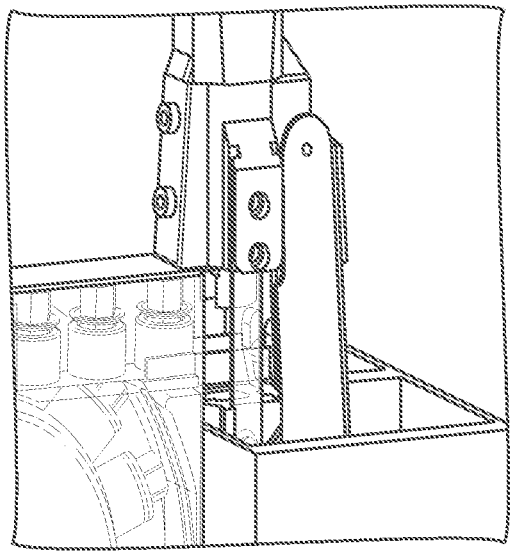
Figure 54C:
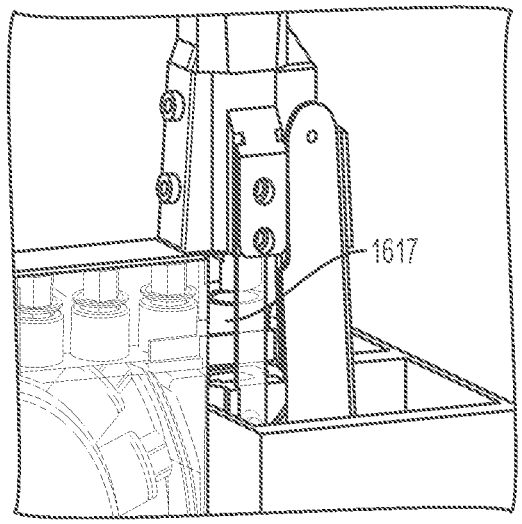
Figure 54D:
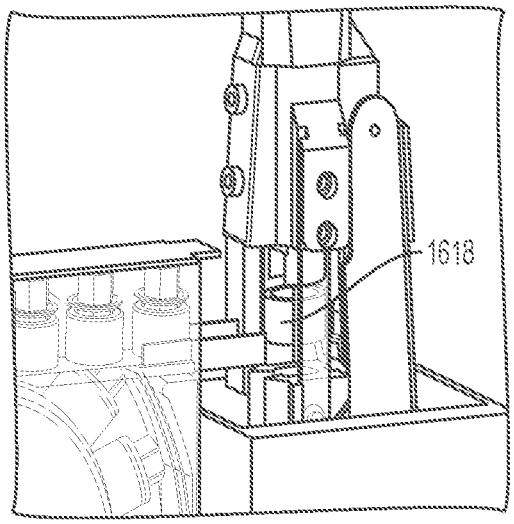

In some embodiments, the cap is designed to be inserted into a multi-pack cartridge (see, e.g., FIGS. 10 and 53). The caps may be stacked together in numbers and in a self-sealing manner, with each cap sealing the next cap in the stack/cartridge.

Figure 42:
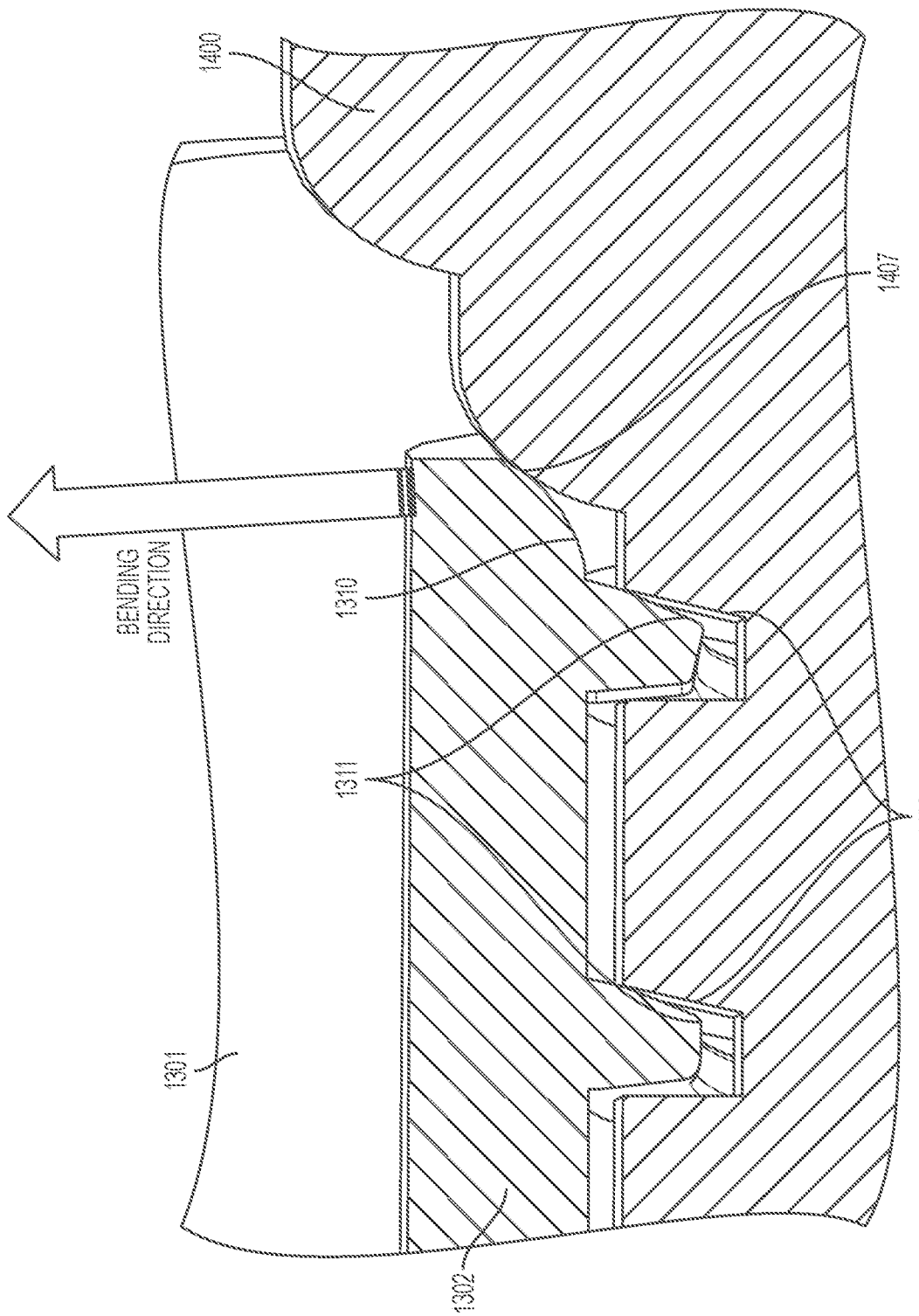
FIG. 42 is a cross-section view of the hub and cap engagement according to one embodiment.
Figure 43:
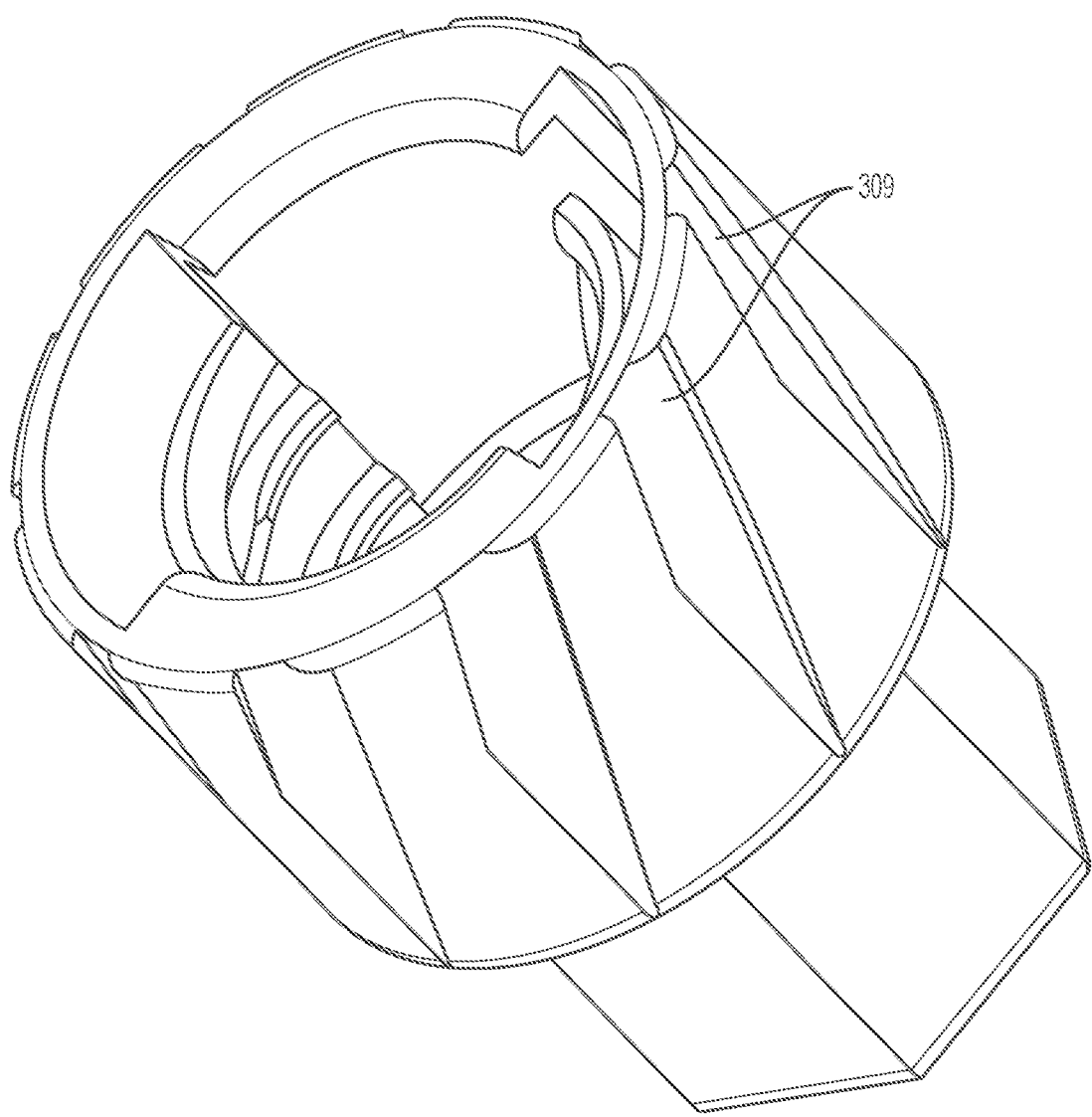
FIG. 43 is a perspective view of the cap according to another embodiment.

As shown in FIG. 42, in some embodiments, the threads of the cap may be designed with a curved, beveled or angled edge to avoid locking and assist a thread snapping mechanism to work with lower torque As will be appreciated, this enhancement is performed by the curved, beveled, or angled thread edge 1311 as well as angled/curved periphery of the compliant threaded mechanism 1310 which can push against the hub's end of thread geometry 1407 and push the compliant mechanism aside and allows threads to release and snap over the hub's luer thread and the cap automatically moves back to match the threads with the hub again. This happens in each rotation of the cap around the hub. This feature assists it to flex away of the threaded hub and help low torque snapping action. This can be adjusted and modified for different hub design to make use of their specific geometrical embodiments. On the other hand reduces the battery consumption of the handheld device.

In some embodiments, the cap creates fast axial translation (axial periodic back and forth motion/vibration) while being rotated by only a rotary actuation which eliminates the need for an axial actuator. This is the result of its compliant threaded feature that causes thread snapping action and pushing the cap one thread back to match the threads together.

In some embodiments, two or more threaded or partially threaded compliant cover members 1303 are used in a 180 degree position configuration with two (or more) gaps 1305. An accommodating sponge or foam 1306 may be positioned in between the two or more gaps for reserving the disinfection chemical solution and absorption of the dirt or blood clot. In some embodiments, the foam and threaded compliant member are integrated in an embodiment which covers the foam and ensures encapsulation or an originally sealed cavity 1301. The cap is sealed to avoid dryness and can be unsealed prior to the use. The sealed cavity 1301 may be designed to be sealed with a film attached to the cavity. The film does not touching any of the foams or compliant threaded mechanism.

In some embodiments, the cap has a structure 1302 which enables actuation. For example, the body of the cap may have a hexagonal shape 1302, which enables loading and/or unloading actions to be performed both manual or automatically. Color chemical indicators may be used to sense the wetness of the cap prior to unsealing. A broad range of chemicals may be used. The cap embodiment may be made of transparent material to allow visual inspection of the cap state. In some embodiments, the cap color may change in the absence of disinfecting agent.

In some embodiments, a thick foam/sponge 1306 is used in the gap for cleaning the surface of the thread and the tip as well as partially penetrating into the threaded grooves of the hub. A thinner layer of foam or cloth (307) or similar material may be placed over the threaded structure 1303 and may be soaked in disinfection solution. It is meant to penetrate the grooves and deep cleaning. While the thread snaps over the thread it also ensures thorough side cleaning with high friction.

In some embodiments, the cap design may include a structure, for example a turbine 309, in the outer/inner body which creates air flow while being rotated. This may decrease the time of drying. The airflow might be blowing or preferably here creating vacuum around the hub.

The cap may be designed with a compliant structure to perform cleaning in two stages: In a first stage, the cap squeezes the foam between the cap structure and the hub to release as much disinfecting solution as possible. In the second stage, the pressure on the cap is released and the cap's foam is expanded to absorb maximum dirt and particles from the hub surface and enhance the drying time by absorbing most of the released disinfection solution.

In some embodiments, the cap may include a capsule membrane which holds (encapsulates) the whole or part of the disinfection solution and releases them under pressure after being tightened to the hub. The encapsulated solution can be SLIP for anti-bacterial coating and non-sticky surface coating. The cap may integrate a pin/needle shape structure to perforate the capsule and release the chemicals. SLIP surface treatment material might be included in the disinfection solution or being sprayed automatically after drying process is complete.

According to one embodiment, the cap may be designed to be inserted inside a cartridge system. The caps also may stacked together in numbers in a self-sealing manner and each cap seals the next cap in the stack/cartridge.

Figure 52:
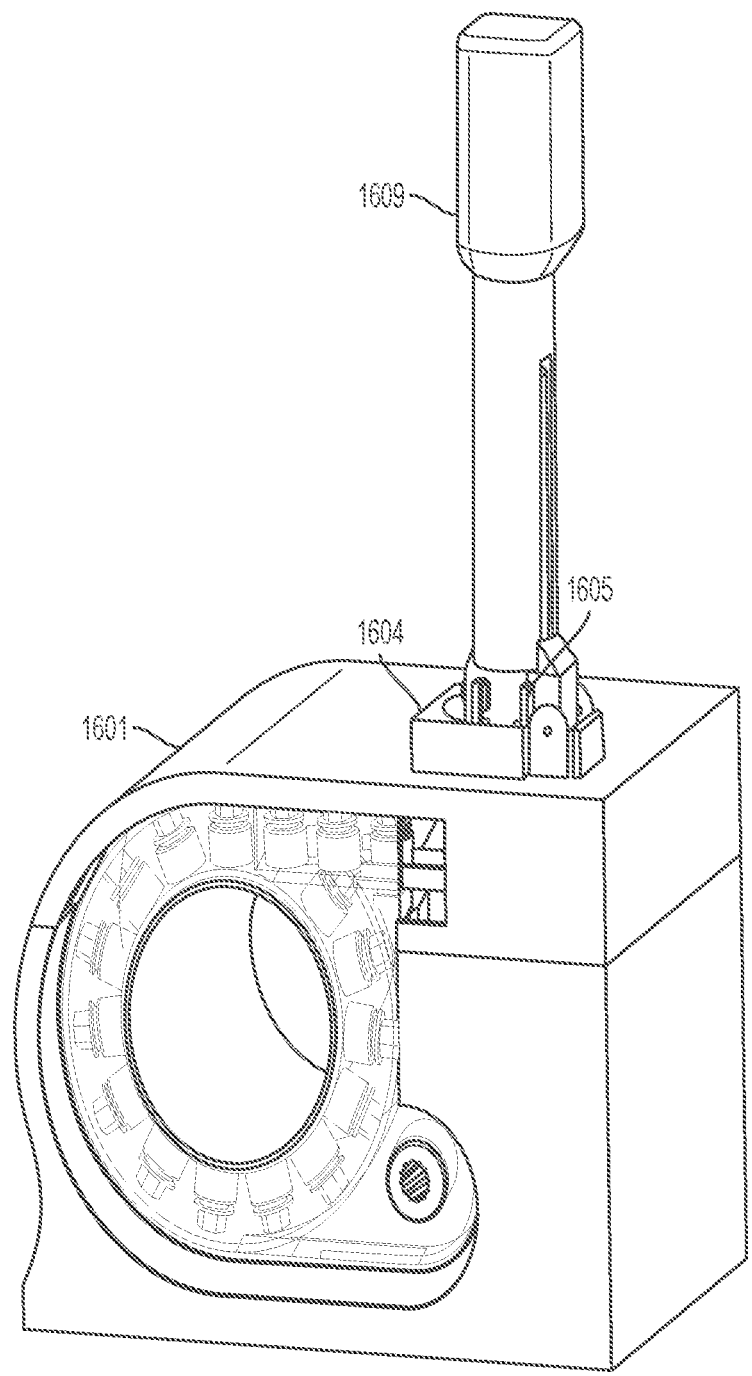
FIG. 52 is a perspective view of the charging station of FIG. 51 with an attached cleaning device.

As previously described, and as shown in FIG. 52, in some embodiments, the device may be coupled to a base, such as charging station. As will be appreciated, the charging station may be configured to charge the device. In some embodiments, the charging station may wirelessly charge the device, although the device also may be charged via a wired connection (e.g., via a cord). For example, the charging station 1601 may include conducting contact 1605 for contact charging of the device. The charging station also may include a wireless charging coil for contactless charging. As will be appreciated, the charging station may be installed on the bed or at a variety of bedside locations.

Figure 51:
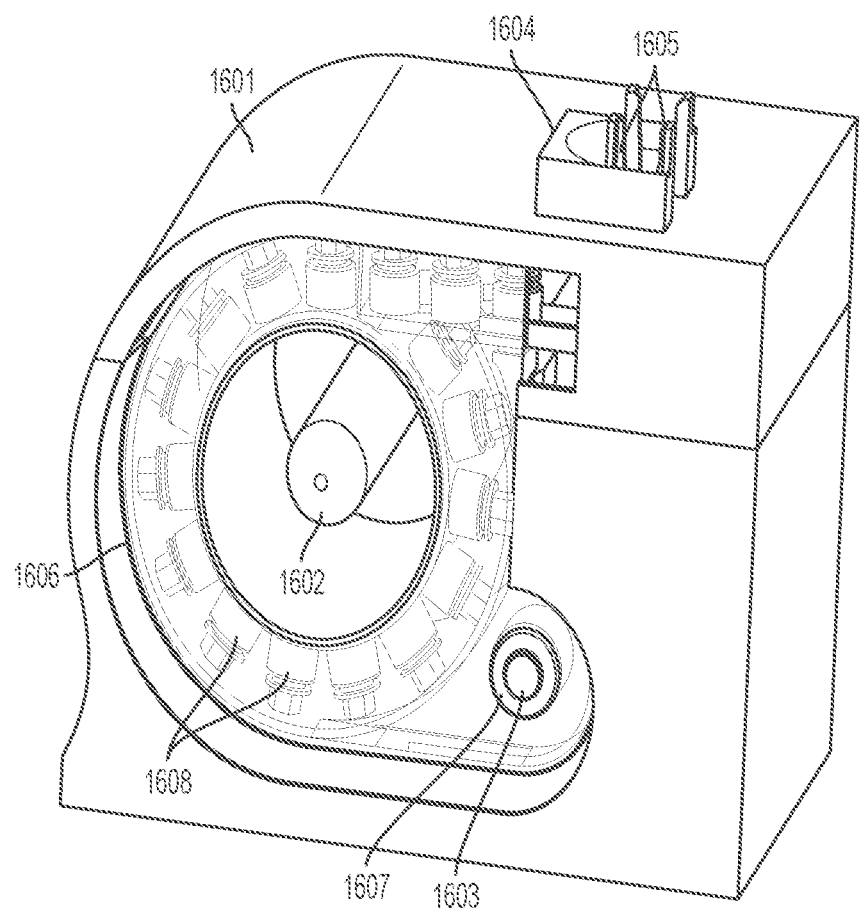
FIG. 51 is a perspective view of the charging station of FIG. 50 shown in partial phantom.

As shown in FIG. 51, the charging station 1601 includes a port 1604, into which a device 1609 may be plugged. As will be appreciated, the port 1604 may lock the device 1609 to the charging station 1601 mechanically, by an actuator, or by magnetic force. In some embodiments, the port 1604 also may include guiding members to encourage easy and precise coupling and decoupling of the device and charging station. For example, the port 1604 may include tracks that are inserted into corresponding openings in the device 1609 when the device is coupled to the charging station 1601.

In addition to charging the device, the charging station also may be configured to sterilize the device (e.g., via UV light for disinfection purposes), download and/or transmit data, and/or dispense a cleaning cap.

FIG. 51 shows a charging station 1601 into which disposable caps 1608 have been loaded. In some embodiments, the charging station may be loaded with between 1 cap and 200 caps. In other embodiments, the charging station may be loaded with between about 25 caps and 200 capsAs with other embodiments, in this embodiment, the caps 1608 are stored in a multipack cartridge 1606 (see FIG. 53), that is loaded into the charging station 1601. In one embodiment, the charging station may include a pin 1602, or other suitable mechanism) for precise insertion and loading of the cartridge into the charging station 1601. In such an embodiment, the cartridge may include a corresponding opening into which the pin 1602 is inserted.

In one example, the cartridge may have a spiral or circular configuration to accommodate large numbers of caps in the cartridge. In another example, the cartridge may have a number of caps in a stacked form for automatic loading. As will be appreciated, the caps may be disposable.

The caps may be sealed using a ribbon (e.g., a roll or film) of an aluminum or polymer film 1610. In one embodiment, the caps may are positioned in a specific arrangement on the ribbon with a desired distance between adjacent caps. The ribbon 1610 is wound around a winding roller 1607 inside the cartridge. As will be described, an actuated spool, actuated by a motor, may be used to unwind and move the ribbon 1610 and, thus, move and position the caps inside the cartridge. As will be appreciated, with this sealing and unsealing mechanism, the caps 1608 may be kept within the cartridge (e.g., unsealed and sanitary) until only moments before the cap is positioned in the cap holder for use.

In some embodiments, the charging station 1601 may automatically load a new (e.g., fresh or unused) cap into the device 1609 (e.g., into the cap holder). As will be appreciated, the caps also may be manually loaded onto the device. For example, a clinician may remove a cap from the charging station and manually insert the cap into the cap holder of the device. In some embodiments, the charging station 1601 also may be allow automatic unloading and/or disposing of the used (e.g., expired or dirty) caps from the device 1609. For example, in one embodiment, the charging station includes an opening into which the dirty caps may be inserted.

An example of the loading process is illustrated in FIGS. 54A-D. As is shown, the loading process involves moving the device towards the cartridge until the cap holder 1618 is positioned adjacent to an opening in the cartridge. In some embodiments, the cap holder 1618 may be positioned adjacent to the opening when the device is inserted into the port 1604. As is shown in FIG. 52B, after the device 1609 is inserted into the port, the cap holder is positioned adjacent the opening by laterally translating the port device. In some embodiments, the port may translate via an actuator, while in other embodiments, the port may be manually translated by pushing the device. Next, a cap is laterally loaded into the cap holder (see FIG. 54C). Finally, as shown in FIG. MD, once the cap has been loaded and locked in the cap holder, the port and device translate back to the original position. The device may now be picked up by a user and used to disinfect a hub. As will be appreciated, in embodiments in which the device and port were not translated (e.g., the device was simply inserted into the port for cap loading), once the cap has been loaded and locked in the holder, the device is ready for use. In some embodiments, the device is locked into the charging station while the cap is being loaded into the cap holder.

Although the cap is described as being laterally loaded into the cap holder, it will be appreciated that other suitable arrangements may be used. For example, in one embodiment, the cap 1609 may be axially loaded into the cap holder. In such an embodiment, the device may be moved to perform the axial loading of the cap. In still another embodiment, the cap may be picked up and inserted into the cap holder via a separate actuation system. In yet another embodiment, another feature, such as a track 1619 on the cap (see FIG. 55A), may be used for cap handling.

Figure 55C:
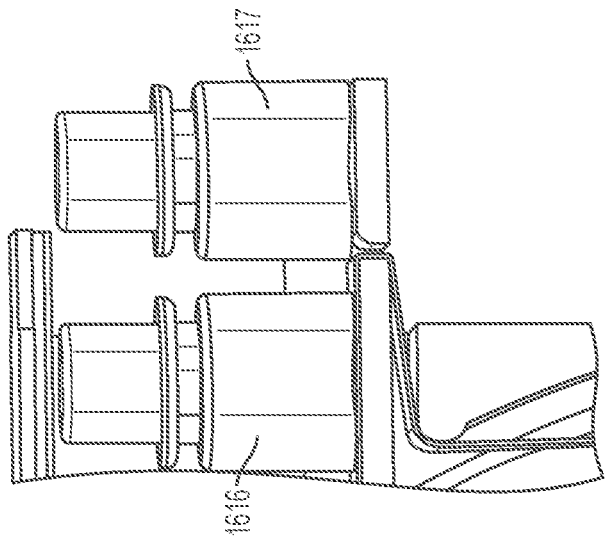
FIG. 55A-55C are perspective views of a portion of the charging station.
Figure 55B:
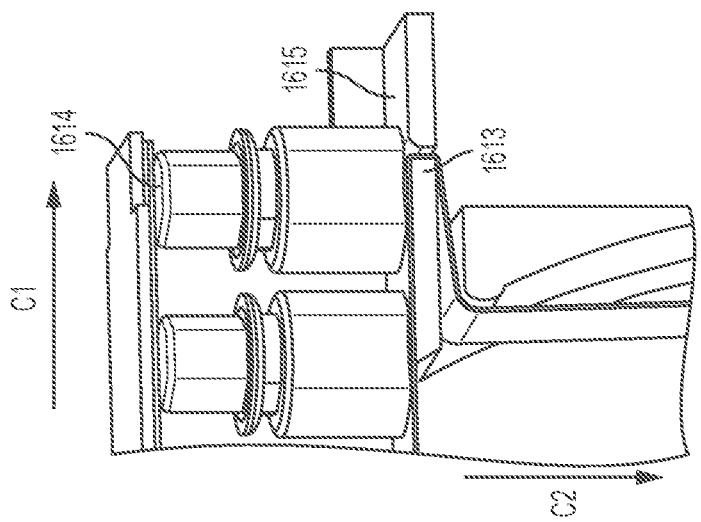
Figure 55A:
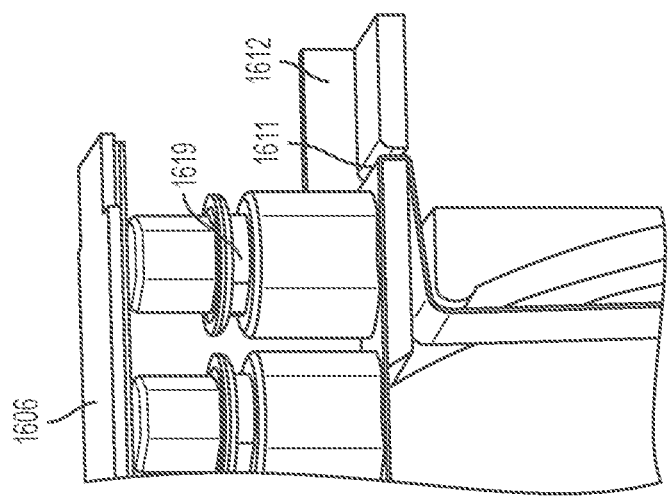

An example of the lateral loading of the cap into the cap holder is illustrated in FIGS. 55A-55C. In this embodiment, as shown in FIG. 55A, the next sealed cap is kept sealed and inside the cartridge until just before being used (e.g., until the device is inserted into the port). Next, as shown in FIG. 55B, as the sealing ribbon 1610 is wound via the actuated spool 1603, the ribbon 1610 and cap 1608 are moved towards the opening (see arrow labeled C1). As the ribbon 1610 is moved around ledge 1613 and towards the roller (see the arrow labeled C2), the cap 1608 is separated or peeled from the ribbon 1610 and moved, onto the platform 1615, for insertion into the cap holder in an unsealed form. In some embodiments, the cleaning caps may be peeled and inserted into the cap holder in between about 1 and 10 seconds. In some embodiments, the unsealed cap must be used within about 2 to 5 minutes. A will be appreciated, the caps must be used before the necessary amount of cleaning solution is dried up. As described, the cleaning cap may have an indicator to alert a clinician when an unused cleaning cap is no longer suitable for use.

Although the caps are shown as being unsealed by peeling the caps from the ribbon in a lateral movement, the caps may be unsealed in other manners. For example, the caps (608) may be unsealed by twisting or another suitable motion that peels off the sealing. In another embodiment, the sealing on the cap may be a breakable membrane, which is ruptured before use. In still another embodiment, the sealing is cut off by the system prior to the loading. In yet another embodiment, the complete spiral ribbon of caps is actuated by a motor or mechanical actuator.

In some embodiments, the cartridge includes sensors for position sensing and/or limit switches. For example, the cartridge may have an integrated sensor to check the position of the cap. In some embodiments, the cartridge is transparent or has a transparent window or an opening to allow for a user to view that the cap is in the required position for precise loading of the cap into the cap holder.

In some embodiments, the cartridge is disposed. In other embodiments, the cartridge may be reused. That is, disposable (or reusable) caps may be loaded into a reusable cartridge.

In some embodiments, the charging station communicates with a control board through digital, serial or wireless communication techniques.

The charging station may include various sensors for position sensing, loading sensing, plugging sensing, alcohol sensing, cartridge sensing, and/or cartridge status. Other suitable sensors may be used in other embodiments.

In one embodiment, the charging station includes a wet detection sensor to ensure that the loaded caps are not dried because of sealing problem, production and packaging issues. For example, the sensor may sense for the presence of alcohol on the caps. In some embodiments, the wet sensor may include a vacuum pump that sucks the air through an optical, chemical, or capacitance sensor to detect for the presence of moisture (e.g., the presence of alcohol). The wet sensor also may include a color sensor that detects the presence of moisture by checking for a change in the color of the cap, foam and/or sealing.

The charging station also may include some optical and vocal indicators and alarms to inform the system status, failure, and/or cap dry-out, although other events may trigger the alarm. In some embodiments, the charging station includes a log file to record the system status and use. The charging station also may include an RFID tag (or other tag) reader/writer to read the type of caps, cartridge, and/or programming.

In some embodiments, the charging station may include a programmable timing process to dismiss the cap that is loaded and has not been used for certain period of time. In such embodiments, the cartridge may include a code or other type of indicia (e.g., RFID, color, serial, barcode, or security tag) that communicates with the charging station to change the program for specific model of cap, check the expiry date, or indicate the number of tag being used and the remains.

In some embodiments, the charging station may be arranged to disinfect the device, caps, and/or charring station. For example, the charging station may include a UV light for disinfection purposes.

As will be appreciated, the charging station may be installed on the bed or at another suitable bedside location. The charging station also may be installed outside of the patient's room (e.g., at a nurses station). The charging station may include a cable attached to the handheld device in embodiments in which the device is not meant to be cordless. The charging station also may include a wireless charging coil for contact less charging. The charging may be performed through conducting contact.

As will be appreciated, preventing adhesion of bodily fluids and infectious materials (i.e. bacteria) can facilitate efficient cleaning of catheter hubs. All commercially available catheter hubs are fabricated from thermoplastics that have smooth surfaces and no chemical functionality. The adhesion of bodily fluids and bacteria to their surfaces is a function of the hubs surface chemistry. In some embodiments, the hub surface is rendered superhydrophobic to minimize unwanted adhesion. For example, surface modified hubs are fabricated by exposure to oxygen plasma followed by treatment with functionalized perfluorocarbon-based silanes, which renders the surface hydrophobic. Further treatment with liquid based perfluorocarbons permeantly immobilizes a thin film on the hub surface that renders the hub superhydrophobic and facilities self-cleaning (i.e. prevents adhesion of blood and bacteria). In other embodiments, the microstructure of the hub surface can be physically altered to render the surface superhydrophobic. For example, lasers can be used to create etched groves with controlled spacings and depths on the hub surface, which allows one to control the wettability and hence the hydrophobicity of the surface.

As will be appreciated, the cleaning cap may have various different designs. For example, the cap may be fitted with a variety foam, it may protect the hubs by encapsulating them with an alcoholic gel, it may include a precast foam infused with various monomer solutions, it may include multiple modes of antimicrobial activity, and/or it may be an antimicrobial cap, or may be a free radical generating cap.

In some embodiments, the cap may be fitted with a variety commercially available foams using standard techniques. Foams may be composed of a variety of different polymers including, but not limited to, polyurethanes, polyesters, polyanhydrides, polyethers, polyethylenes (linear or cross-liked), and formaldehyde-melamine-sodium bisulfite copolymers. In some embodiments, the foams are selected based on swelling ratio (Q) and mechanical strength (i.e., shear moduli, G). The foam also may have a medium density (1-5 g/cm 3) open-cell reticulated structure with pore sizes ranging from 100-1000 μm, a Q value of >400 for solutions containing 70% isopropyl alcohol (IPA) and shear moduliG>1 GPa. FIG. 56 provides a list of commercially available foams that were soaked in 70% IPA for 24 hours and that had their swelling ratios determined.

In such embodiments, cleaning of the hub may be accomplished by suturing the foam with an alcoholic solution (e.g., 70% isoprophy alcohol ("IPA") containing chlorohexidine (1-2 wt/vol %) before the cap is sealed. Cleaning may be initiated when the practitioner removes the seal and places the cap in the device. That is, the device threads the cap on the hub, which puts the hub into direct contact with the alcohol-containing foam. The cap may be rotated around the hub at high speeds, which simultaneously cleans, disinfects, and dries the hub. Alternately, cleaning of the hub is accomplished by placing a sponge or a capsule containing a chlorohexidine alcoholic solution (70% IPA) in the bottom of the cap. In such embodiments, when the device threads the cap onto the hub, the capsule breaks and releases the cleaning solution.

Figure 57:
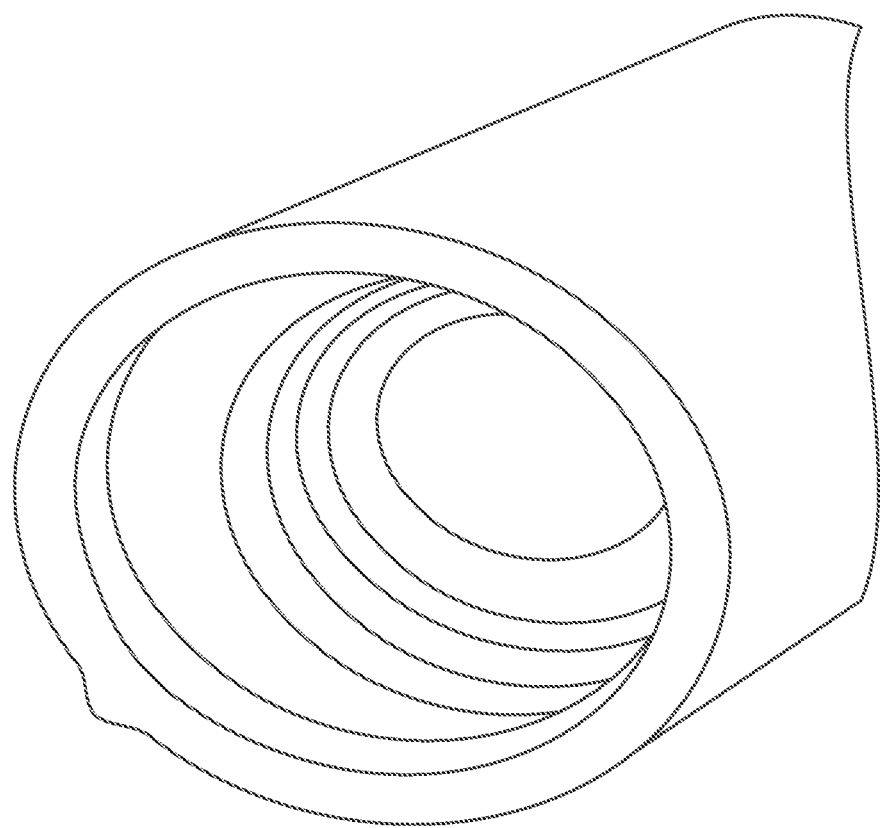
FIG. 57 is a perspective view of one embodiment of a alcolgel foam.

In other embodiments, alcogel caps may be used to protect central line hubs by encapsulating them within an elastic alcoholic gel, also known as alcogels. As will be appreciated, alcogels are hydrophilic materials that contain low mass fractions of cross linked polymers (<10 wt %) that may retain a significant fraction of alcoholic-solutions within their polymer structure. The amount and type of alcoholic solution that can be retained within these materials may be tailored by careful selection of the monomers and cross linking agents as well as their relative mole fractions in the final cross linked polymer. For example, monomers such as acrylic acid, styrene, 2-acrylamido-2-methylpropane sulfuric acid (AMPS), N-isopropylacrylamide ("NIPAM"), and methacryloyloxyethyl phosphorylcholine can be cross linked with $Zn^{2+}$, N,N'-methylenebisacrylamide ("MBA"), ethylene glycol dimethacrylate (EGDMA), triethylen glycol dimethacrylate ("TEGDMA"), and 1,3-di-glycerolate to yield different gels with varying alcohol absorbing abilities. Polymerization may be facilitated via γ-irradiation, x-ray irradiation, or chemical cross linking, which may enable one to use fabricate caps with matching threads to the most commonly used hubs. In one embodiment, the alcogel is comprised of materials Generally Regarded as Safe by the FDA and absorbs between of 50-90 vol % ethanol or isopropyl alcohol. A representative alcogel polymerized from 2-acrylamido-2-methylpropane sulfuric acid with PEGDMA as a crosslinker is shown in FIG. 57.

Cleaning with the alcogel cap may be achieved by removing the seal and threading the device onto the desired hub. In one example, disinfection occurs through the direct surface contact between the alcogel and the Hub, which provides constant exposure to a 70% IPA solution. As will be appreciated, the threading mechanism enables disinfection of the threads, an area that is notoriously difficult to clean with the current standard of care.

In other embodiments, a hydrogel-foam hybrid caps may be use. In some embodiments, precast foams with desired mechanical properties can be infused with various monomer solutions and subsequently cross linked to yield an interpenetrating network with improved mechanical and chemical properties. For example, malemine foams have a large swelling ratio (Q=724) but very poor mechanical properties. To enhance the mechanical properties, these foams can be infused with elastic monomers such as acrylic acid and PEGDMA. By tailoring the monomer weight percents and the degree of crosslinking, these foams may be transformed into highly elastic hybrids materials.

In another embodiment, an antimicrobial cap may be used. As will be appreciated, antimicrobial caps may be hydrogel-based caps that contain antimicrobial agents and nanoparticles embedded within their structure. Hydrogels may be fabricated using water-soluble monomers that are cross linked using either γ-irradiation, x-ray irradiation, UV or chemical reagents. Monomers may be selected from a broad array of materials (i.e. polyethylene glycol, polyacrylic acid, polyacrylamide, polyvinyl alcohol, N-(2-Hydroxypropyl) methacrylamide (HPMA), Xanthin Gum, pectins, chitosan, dextran, carrageenan, guar gum, cellulose ethers, hyaluronic acid, albumin, starch and starch based derivatives, among others). Antimicrobial agents may include chlorohexidine, peptides (chosen from the Antimicrobial Peptide Database, APD; contains 2600 peptides), or nanoparticles. These reagents may be easily modified to contain a cross-linkable group using standard techniques and incorporated into the hydrogel using the before-mentioned conjugation techniques. The material properties of the gels (i.e. elasticity, rigidity, compressibility, etc.) may be tailored by careful selection of the monomers and cross linking agents as well as their relative mole fractions for a given formulation. Similar to alcogels, these systems may enable fabrication of caps with matching threads to the most commonly sold hub devices.

Cleaning with the antimicrobial cap may be achieved by removing the seal and threading the device onto the desired hub. In some embodiments, disinfection occurs through the direct surface contact between the antimicrobial peptides and nanoparticles and the hub, which provides constant exposure to a antimicrobial agents. In some embodiments, the unique threading mechanism enables disinfection of the threads, an area that is notoriously difficult to clean with the current standard of care.

In still another embodiment, an hybrid cleaning cap may be used. As will be appreciated, alcohol based disinfectants work by denaturation of proteins, osmolarity works by rupturing/collapsing the cell membrane, antimicrobial agents disrupt the cell membrane, and peroxides generate free radicals which rupture the cell membrane and damage the bacteria's cellular machinery. In some embodiment, a hybrid cap combines multiple modes of antimicrobial activity into a single device to provide enhanced microbial activity. These Possible configurations may include: (1) an alcogel containing chlorohexidine (1-5 wt %) (Hypotonic solution+antimicrobial agent); (2): a hydrogel containing a hypertonic hydrogen peroxide solution (359 g/L NaCl, 3% $H_2O_2$). (Hypertonic solution+Radicals); (3) a hydrogel containing hydrogen peroxide solution (3% $H_2O_2$) (Hypotonic solution+Radicals); (4) a hydrogel containing hydrogen peroxide solution and poly-L-lysine (Hypotonic solution+Radicals+Antimicrobial Agents); and (5) an alcogel containing Hydrogen Peroxide and chlorohexidene (Alcohol+Radicals+Antimicrobial Agents). In some embodiments, a cleaning solution may include a combination of between about 0.5-5% chlorhexidine gluconate by volume, 70-90% isopropyl alcohol by volume, and between about 5 and 20% hydrogen peroxide by volume.

In yet another embodiment, a free radical generating cap may be used. As will be appreciated, UV radiation is one of the most effective antimicrobial therapies because it can generate larger concentrations of free radicals, which rupture the cell membrane and damage the bacteria's cellular machinery. In some embodiment, a radical cap aims to imitate the radical generating capabilities of UV light with chemical reagents. Such radical caps may require two (or more) reagents to generate the free radicals, an initiator and an accelerant. In some embodiments, to enable the prolonged generation of radical species one reagent is dispersed within the foam/hydrogel (Reagent A) while the other reagent is encapsulated within a microbead (Reagent B). The microbead may be fabricated using the same water-soluble polymer described above and using a variety of techniques, such as reverse emulsion polymerization. The material properties of the beads also may be tailored such that the pressure applied during the cleaning process releases Reagent B from the microbead and triggers radical generation. There are several combinations of chemicals that may be used to generate free radicals. Possible combinations may include (1) APS/TEMED; and (2) NOS/L-arginine.

As will be appreciated, although embodiments have been shown and described for modifying cleaning caps (e.g., applying various coatings to the exterior surface of the cleaning cap), it should be appreciated that the hubs also may be modified. For example, in some embodiments, the cleaning of surface modified hubs maybe accomplished using any of the methods described above (e.g., applying a coating of a self-cleaning solution). In addition, the super lubricating layer may be continually replenished in these systems by encapsulation of the oil within said foam, hydrogel, or alcogel. In some embodiments, the advantage of this approach may be that the hub is cleaned and simultaneously coated with the lubricant, which aids in preventing adhesion of blood and bacteria. In some embodiments, the combination of the super lubricating film and the unique cleaning mechanisms may greatly reduce the risk of infection during long term use. As will be appreciated, manufacturing processes that enable production of caps or hubs including blow molding, injection molding, screw extrusion, die extrusion, calendaring, compression molding, rotational molding, thermoforming, and power injection molding.

While the present teachings have been described in conjunction with various embodiments and examples, it is not intended that the present teachings be limited to such embodiments or examples. On the contrary, the present teachings encompass various alternatives, modifications, and equivalents, as will be appreciated by those of skill in the art. Accordingly, the foregoing description and drawings are by way of example only.

What is claimed is:

1. A method of cleaning a hub of a catheter, the method comprising:
engaging external threads of the hub with a cleaning cap having a cleaning member, wherein the cleaning cap includes two or more threaded members spaced from at least a portion of a cap body and a radial gap positioned between the threaded members and the portion of the cap body, wherein the two or more threaded members oppose one another and are at least partially surrounded by the cap body, and wherein engaging the external threads of the hub with the cleaning cap includes engaging the external threads with helical threads of each of the two or more threaded members;
contacting at least a portion of the hub with the cleaning member disposed within a cavity of the cleaning cap between a first threaded member and a second threaded member of the two or more threaded members,
wherein the two or more threaded members are adapted to flex radially away from the external threads so that the helical threads are at least one of slidable, snappable, or jumpable over the external threads of the hub.

2. The method of claim 1, wherein the cleaning member comprises a foam material configured to contact the portion of the hub.

3. The method of claim 1, wherein the cleaning member comprises a fabric material.

4. The method of claim 1, wherein the cleaning member includes at least one of a disinfecting substance and an antiseptic fluid.

5. The method of claim 1, wherein the cap body includes one or more gaps disposed about a circumference of the cap body, the one or more gaps extending axially from a first end portion of the cap body.

6. The method of claim 5, wherein the one or more gaps are configured to allow outward radial flexing of the cleaning member.

7. The method of claim 1, wherein the cleaning cap includes actuation pins that extend from a bottom surface of the cap body, the actuating pins configured to engage with a cleaning apparatus.

8. The method of claim 1, wherein the cleaning member includes a cleaning pin configured for intra-valvular cleaning of a valve of a tip of the hub.

9. The method of claim 8, wherein the cleaning pin has a cylindrical shape.

10. The method of claim 1, wherein the cleaning member comprises a foam, a hydrogel, and/or an alcogel.

11. The method of claim 10, wherein the foam, the hydrogel, and/or the alcogel encapsulates an alcoholic solution, a radical generating solution, antimicrobial peptides, antimicrobial nanoparticles, and/or disinfectants.

12. The method of claim 10, wherein the foam, the hydrogel, and/or the alcogel encapsulates a self-cleaning solution, the self-cleaning solution having oils.

13. The method of claim 12, wherein after the hub is cleaned, the self-cleaning solution is arranged to coat the hub to render it superhydrophobic.

14. The method of claim 1, further comprising making an audible or tactile alert when the cleaning member engages with the external threads of the hub.

15. The method of claim 1, further comprising locking the hub relative to the cleaning cap when the cleaning cap is engaged with the hub.

16. The method of claim 1, wherein the cap includes an indicator to indicate at least one of a wetness or dryness of a cleaning solution in the cap prior to use.

17. The method of claim 16, wherein the indicator is a color indicator arranged to display a color when the cleaning solution in the cap is dry.

18. The method of claim 1, wherein the step of engaging includes rotating the cleaning cap relative to the hub.

19. The method of claim 18, further comprising applying a constant axial force to the hub when the cleaning cap is rotated relative to the hub.

20. The method of claim 1, wherein the helical threads include at least one of a curved, angled or beveled shape.

21. The method of claim 1, wherein the two or more threaded members include a cloth disposed over the helical threads.

22. The method of claim 10, wherein the foam contains at least one of a cleaning solution and a membrane capsule.

23. The method of claim 10, wherein the foam is disposed along at least a portion of the cavity.

24. The method of claim 1, wherein an exterior surface of the cap body includes a handle and/or a holding feature for manual use.

25. The method of claim 1, further comprising leaving the cleaning cap on the hub to cover the hub and maintain a sterile environment.

26. The method of claim 25, wherein the step of engaging is performed before the step of leaving.

27. The method of claim 1, wherein the two or more threaded members are integrally formed with the cap body.

* * * * *